US008871223B2

(12) United States Patent  (10) Patent No.: US 8,871,223 B2
Friedman et al.  (45) Date of Patent: *Oct. 28, 2014

(54) HSV-1 AND HSV-2 VACCINES AND METHODS OF USE THEREOF

(75) Inventors: Harvey Friedman, Merion, PA (US); Elizabeth E. Zumbrun, Middletown, MD (US); Fushan Wang, Broomall, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1172 days.

This patent is subject to a terminal disclaimer.

(21) Appl. No.: 12/440,223

(22) PCT Filed: Sep. 7, 2007

(86) PCT No.: PCT/US2007/019537
§ 371 (c)(1),
(2), (4) Date: Jan. 25, 2011

(87) PCT Pub. No.: WO2008/030560
PCT Pub. Date: Mar. 13, 2008

(65) Prior Publication Data
US 2011/0177125 A1    Jul. 21, 2011

Related U.S. Application Data

(60) Provisional application No. 60/842,947, filed on Sep. 8, 2006, provisional application No. 60/929,050, filed on Jun. 11, 2007.

(51) Int. Cl.
*A61K 39/245* (2006.01)
*A61P 31/22* (2006.01)
*C12N 15/38* (2006.01)
*C07K 14/03* (2006.01)
*C07K 14/035* (2006.01)
*C07K 14/005* (2006.01)
*C12N 7/00* (2006.01)
*A61K 39/00* (2006.01)

(52) U.S. Cl.
CPC .......... *A61K 39/245* (2013.01); *C07K 14/005* (2013.01); *C12N 2710/16661* (2013.01); *A61K 2039/5254* (2013.01); *C12N 2710/16634* (2013.01); *C12N 2710/16622* (2013.01); *C12N 7/00* (2013.01)
USPC .................. 424/231.1; 424/184.1; 424/229.1; 435/5

(58) Field of Classification Search
CPC ................ C12N 2710/00; C12N 2710/16011; C12N 2710/16034; C12N 2710/16061; C12N 2710/16611; C12N 2710/16661
See application file for complete search history.

(56) References Cited

U.S. PATENT DOCUMENTS

| 4,709,011 A | 11/1987 | Cohen et al. |
| 4,762,708 A | 8/1988 | Cohen et al. |
| 5,149,529 A | 9/1992 | Ho et al. |
| 5,612,041 A | 3/1997 | Burke et al. |
| 5,837,532 A | 11/1998 | Preston et al. |
| 5,955,088 A | 9/1999 | Ghiasi et al. |
| 6,193,984 B1 | 2/2001 | Ghiasi et al. |
| 6,406,705 B1 | 6/2002 | Davis et al. |
| 6,613,892 B2 | 9/2003 | Preston et al. |
| 7,264,814 B2 | 9/2007 | Nishiyama |
| 8,057,804 B2 | 11/2011 | Friedman et al. |
| 2003/0129199 A1 | 7/2003 | Stephenne et al. |
| 2003/0152583 A1 | 8/2003 | Cohen et al. |
| 2003/0215463 A1 | 11/2003 | Knipe et al. |
| 2004/0197347 A1 | 10/2004 | Sykes et al. |
| 2004/0228876 A1 | 11/2004 | Nishiyama |
| 2005/0112142 A1 | 5/2005 | Spaete et al. |
| 2005/0118192 A1 | 6/2005 | Boursnell et al. |
| 2009/0246227 A1* | 10/2009 | Friedman et al. .......... 424/231.1 |
| 2011/0177125 A1 | 7/2011 | Friedman et al. |
| 2012/0114695 A1* | 5/2012 | Friedman et al. .......... 424/231.1 |

FOREIGN PATENT DOCUMENTS

| EP | 0139417 A1 | 5/1985 |
| WO | WO 83/02897 | 9/1983 |
| WO | WO01/08701 | 2/2001 |
| WO | WO01/09361 | 2/2001 |
| WO | WO02/087614 | 11/2002 |
| WO | WO02/092826 | 11/2002 |
| WO | WO 02092826 A2 * | 11/2002 |

(Continued)

OTHER PUBLICATIONS

Nagashunmugam T, Lubinski J, Wang L, Goldstein LT, Weeks BS, Sundaresan P, Kang EH, Dubin G, Friedman HM. In vivo immune evasion mediated by the herpes simplex virus type 1 immunoglobulin G Fc receptor. J Virol. Jul. 1998;72(7):5351-9.*

(Continued)

*Primary Examiner* — Benjamin P Blumel
*Assistant Examiner* — Rachel Gill
(74) *Attorney, Agent, or Firm* — Mark S. Cohen; Pearl Cohen Zedek Latzer Baratz LLP

(57) ABSTRACT

This invention provides methods of vaccinating a subject against a Herpes Simplex Virus (HSV) infection and disorders and symptoms associated with same, and impeding, inhibiting, reducing the incidence of, and suppressing HSV infection, neuronal viral spread, formation of zosteriform lesions, herpetic ocular disease, herpes-mediated encephalitis, and genital ulcer disease in a subject, comprising the step of contacting the subject with a mutant strain of the HSV, containing an inactivating mutation in a gene encoding a gE, gI, Us9, or other proteins.

12 Claims, 27 Drawing Sheets

(56) References Cited

FOREIGN PATENT DOCUMENTS

Figure 1:
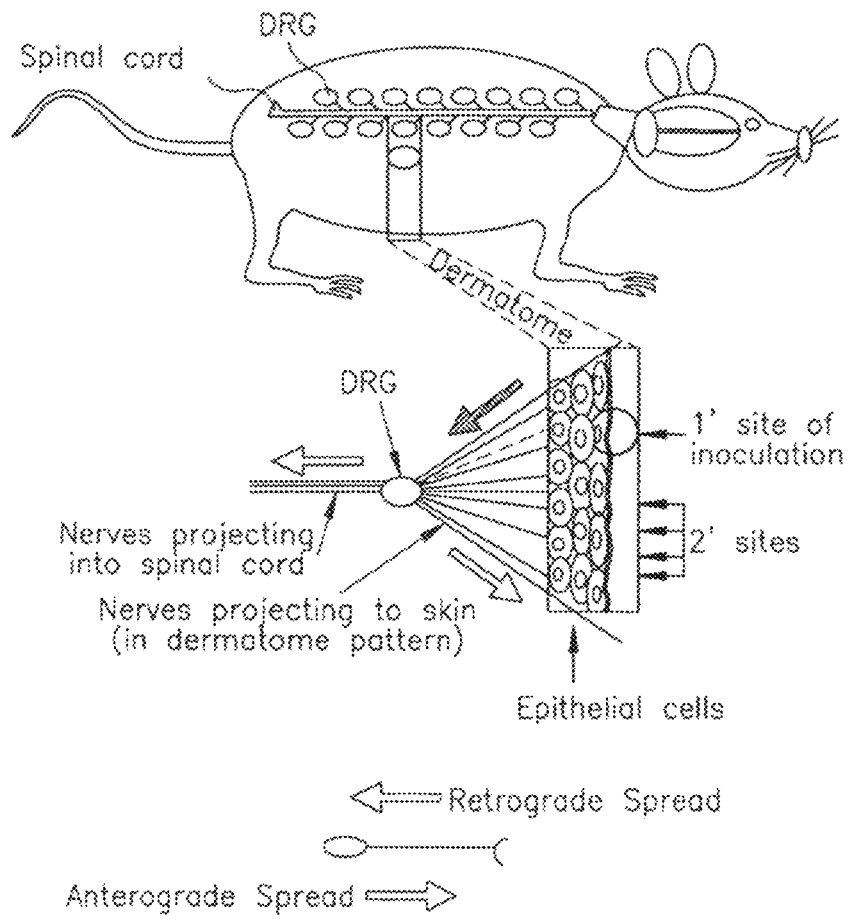
Figure 2:
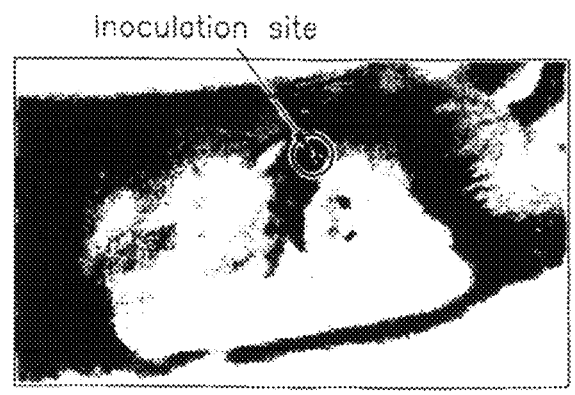
Figure 3:
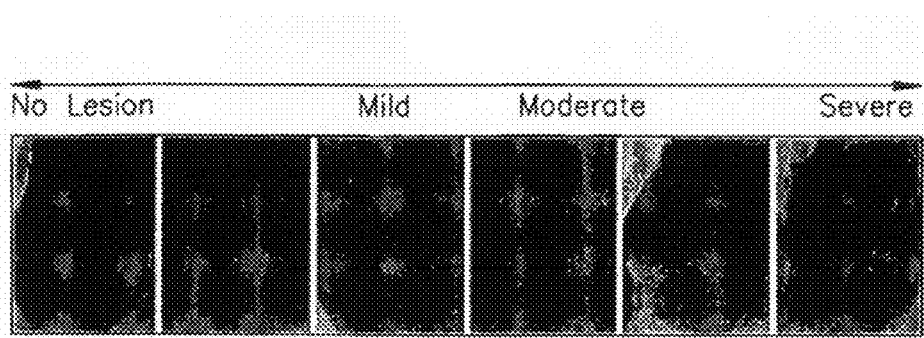
Figure 4:
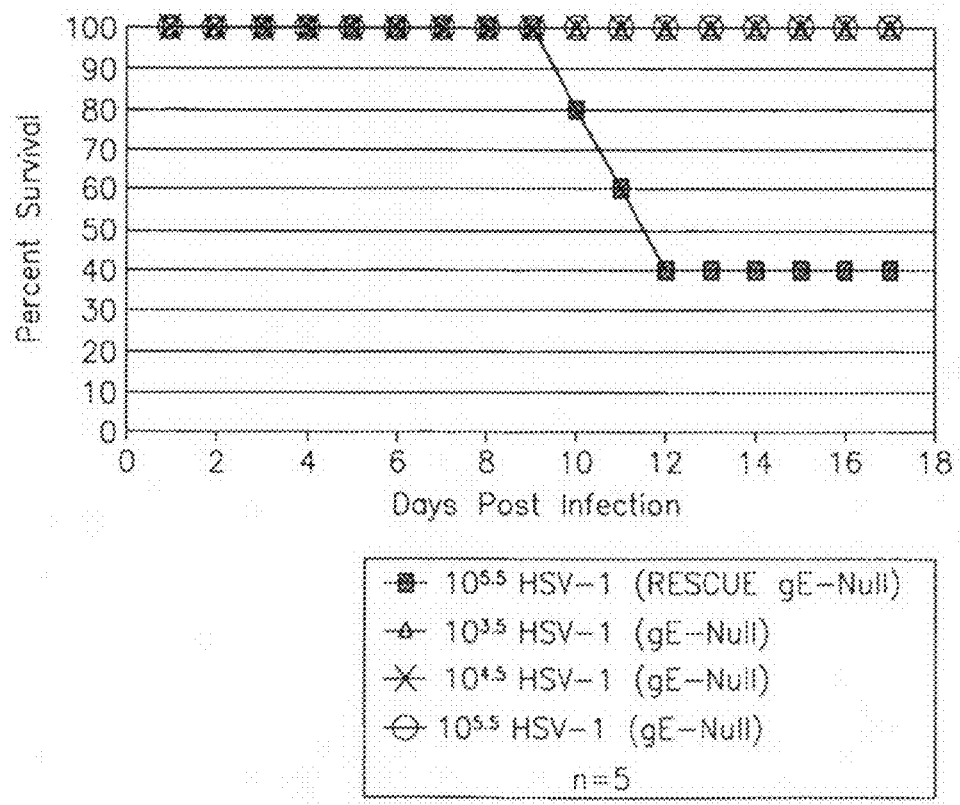

| WO | WO 2003/086308 A3 | 3/2004 |
|---|---|---|
| WO | WO-2004/039400 | 5/2004 |
| WO | WO-2008/030560 | 3/2008 |
| WO | WO 2008/085486 A1 | 7/2008 |
| WO | WO 2010/114930 A1 | 10/2010 |

OTHER PUBLICATIONS

Oxman MN, et. al. A vaccine to prevent herpes zoster and postherpetic neuralgia in older adults. N Engl J Med. Jun. 2, 2005;352(22):2271-84.*
Stanberry LR, Spruance SL, Cunningham AL, Bernstein DI, Mindel A, Sacks S, Tyring S, Aoki FY, Slaoui M, Denis M, Vandepapeliere P, Dubin G; GlaxoSmithKline Herpes Vaccine Efficacy Study Group. Glycoprotein-D-adjuvant vaccine to prevent genital herpes. N Engl J Med. Nov. 21, 2002;347(21):1652-61.*
Aurelian "Herpes simplex virus type 2 vaccines: new ground for optimism?" Clin Diagn Lab Immunol. May 2004;11(3):437-45.
Bernstein (2005) "Glycoprotein D adjuvant herpes simplex virus vaccine" Expert Review of Vaccines 4:615-627.
Bonkowsky et al. "Herpes simplex virus central nervous system relapse during treatment of infantile spasms with corticotrophin". Pediatrics. May 2006;117(5):e1045-8.
Buchwald et al., 1980, "Long-term, continuous intravenous heparin administration by an implantable infusion pump in ambulatory patients with recurrent venous thrombosis", Surgery 88:507.
Caudy et al., 2002, "Fragile X-related protein and VIG associate with the RNA interference machinery", Genes & Devel 16:2491-96.
Cheon et al., 1994, "High-affinity binding sites for related fibroblast growth factor ligands reside within different receptor immunoglobulin-like domains", PNAS USA 91(3):989-93.
Dubin et al., 1991, "Herpes simplex virus type 1 Fc receptor protects infected cells from antibody-dependent cellular cytotoxicity", J. Virol 65:7046-50.
Eisenberg RJ et al., 1985, "Localization of epitopes of herpes simplex virus type 1 glycoprotein D", J. Virol 53:634-644.
Evan et al., 1985, "Isolation of Monoclonal Antibodies Specific for Human c-myc Proto-Oncogene Product", Molecular and Cellular Biology 5:3610-3616.
Field et al., 1988, "Purification of a RAS-responsive adenylyl cyclase complex from *Saccharomyces cerevisiae* by use of an epitope addition method", Mol. Cell. Biol. 8:2159-2165.
Frank et al., 1989. "A novel function of the herpes simplex virus type 1 Fc receptor: participation in bipolar bridging of antiviral immunoglobulin G". J Virol 63:4479-88.
Friedman et al., 1996, "Immune evasion properties of herpes simplex virus type 1 glycoprotein gC", J. Virol. 70:4253-4260.
Ghiasi et al., "Expression of seven herpes simplex virus type 1 glycoproteins (gB, gC, gD, gE, gG, gH, and gI): Comparative protection against lethal challenge in mice", J. Virol., Apr. 1994, 68(4):2118-26.
Ghiasi et al., "Protection against herpes simplex virus-induced eye disease after vaccination with seven individually expressed herpes simplex virus 1 glycoproteins, Invest. Ophthalmol", Vis. Sci., Jun. 1995, 36(7):1352-1360.
Goldstein and Weller, 1988, "An ICP6::lacZ insertional mutagen is used to demonstrate that the UL52 gene of herpes simplex virus type 1 is required for virus growth and DNA synthesis", J. Virol. 62:2970-2977.
Heidaran et al., 1995, "Beta PDGFR-IgG chimera demonstrates that human beta PDGFR Ig-like domains 1 to 3 are sufficient for high affinity PDGFR BB binding", FASEB J. 9(1):140-5.
Hook et al., 2006, "Herpes simplex virus type 1 and 2 glycoprotein C prevents complement-mediated neutralization induced by natural immunoglobulin m antibody", J. Virol. 80:4038-4046.
International Preliminary Report on Patentability (IPRP; Chaper I) for PCT/US07/19537 dated Mar. 19, 2009.
International Search Report of Application No. PCT/US07/19537 issued on Jun. 3, 2008.

Jiang C et al., "Mutations that decrease DNA binding of the processivity factor of the herpes simplex virus DNA polymerase reduce viral yield, alter the kinetics of viral DNA replication, and decrease the fidelity of DNA replication", J. Virol., Apr. 2007, 81(7):3495-502.
Jones and Cunningham (2003) "Development of prophylactic vaccines for genital and neonatal herpes" Expert Review of Vaccines 2:541-549.
Jones et al., "Vaccination strategies to prevent genital herpes and neonatal herpes simplex virus (HSV) disease", Herpes, Apr. 2004, 11(1):12-17.
Judson et al., "Blocking immune evasion as a novel approach for prevention and treatment of herpes simplex virus infection", J. Virol. 77:12639-45, 2003.
Khan et al., "Herpes encephalitis presenting as mild aphasia: case report". BMC Fam Pract. Mar. 24, 2006;7:22.
Koelle and Ghiasi (2005) "Prospects for developing an effective vaccine against ocular herpes simplex virus infection" Current Eye Res 30:929-942.
Labetoulle M et al., "Neuronal propagation of HSV1 from the Oral mucosa to the eye", Invest Ophthalmol Vis Sci. Aug. 2000; 41(9):2600-6.
Larochelle et al., 1995, "Specific receptor detection by a functional keratinocyte growth factor—immunoglobulin chimera", J. Cell Biol. 129(2):357-66.
Lubinski et al, 1998, "Herpes simplex virus type 1 glycoprotein gC mediates immune evasion in vivo", J. Virol 72:8257-63.
Lubinski et al, 1999, "In vivo role of complement-interacting domains of herpes simplex virus type 1 glycoprotein gC", J. Exper Med 190:1637-46.
Lubinski et al, 2002, "Herpes simplex virus type 1 evades the effects of antibody and complement in vivo", J. Virol 76:9232-41.
Lutz-Freyermuth et al., 1990, "Quantitative Determination That One of Two Potential RNA-binding Domains of the A Protein Component of the UI Small Nuclear Ribonucleoprotein Complex Binds with High Affinity to Stem-loop II of U1 RNA", Proc. Natl. Acad. Sci. USA, 87:6393-6397.
Manoj et al., "Mutations in herpes simplex virus glycoprotein D that prevent cell entry via nectins and alter cell tropism". Proc Natl Acad Sci U S A. Aug. 24, 2004;101(34):12414-21. Epub Jul. 23, 2004.
Nagashunmugam et al., "In vivo immune evasion mediated by the herpes simplex virus type 1 immunoglobulin G Fc Receptor", J. Virol. 72:5351-9, 1998.
Nagot et al., "Reduction of HIV-1 RNA levels with therapy to suppress herpes simplex virus", N. Engl. J. Med., Feb. 22, 2007, 356(8):790-9.
Nass et al. (1998) "Antibody response and protective capacity of plasmid vaccines expressing three different herpes simplex virus glycoproteins." J. Infect. Dis. 178:611-617.
Natuk et al., "Recombinant vesicular stomatitis virus vectors expressing herpes simplex virus type 2 gD elicit robust CD4+ Th1 immune responses and are protective in mouse and guinea pig models of vaginal challenge".J Virol. May 2006;80(9):4447-57.
Nesburn et al., "Vaccine therapy for ocular herpes simplex virus (HSV) Infection: perlocular vaccination reduces spontaneous ocular HSV type 1 shedding in latently infected rabbits", J. Virol., Aug. 1994, 68(8):5084-5092.
Osorio et al., "Improved protection from primary ocular HSV-1 infection and establishment of latency using multigenic DNA vaccines" Invest Ophthalmol Vis Sci. Feb. 2004;45(2):506-14.
Pepose et al. (2006) "Ocular herpes simplex: changing epidemiology, emerging disease patterns, and the potential of vaccine prevention and therapy" American Journal of Ophthamology 141: 547-557.
Pyles et al. "Use of immunostimulatory sequence-containing oligonucleotides as topical therapy for genital herpes simplex virus type 2 infection".J Virol. Nov. 2002;76(22):11387-96.
Saldanha et al., 2000. "Herpes simplex virus type 1 glycoprotein E domains involved in virus spread and disease". J Virol 74:6712-9.
Schang et al., "Roscovitine, a specific inhibitor of cellular cyclin-dependent kinases, inhibits herpes simplex virus DNA synthesis in the presence of viral early proteins". J Virol. Mar. 2000;74(5):2107-20.

(56) References Cited

OTHER PUBLICATIONS

Skinner et al., 1991, "Use of the Glu-Glu-Phe C-terminal Epitope for Rapid Purification of the Catalytic Domain of Normal and Mutant ras GTPase-activating Proteins", J. Biol. Chem. 266:15163-15166.
Stanberry et al. (2002) "Glycoprotein-D-adjuvant vaccine to prevent genital herpes" New England Journal of Medicine 347:1652-1661.
Wang et al., 2005. "Herpes simplex virus type 1 glycoprotein e is required for axonal localization of capsid, tegument, and membrane glycoproteins". J Virol 79:13362-72.
Caruthers "Gene synthesis machines. DNA chemistry and its uses". 1985; Science 230:281-285.
Chang et al., "Implications for herpes simplex virus vaccine strategies based on antibodies produced to herpes simplex virus type 1 glycoprotein gC immune evasion domains" Vaccine. Sep. 7, 2005;23(38):4658-65.
Friedman et al., 1984, "Glycoprotein C of herpes simplex virus 1 acts as a receptor for the C3b complement component on infected cells", Nature 309:633-5.
Kennedy et al. "Replication of the herpes simplex virus type 1 RL1 mutant 1716 in primary neuronal cell cultures—possible relevance to use as a viral vector". J Neurol Sci. Oct. 1, 2000;179(S 1-2):108-14.
Klepeis et al., 2003, "Integrated computational and experimental approach for lead optimization and design of compstatin variants with improved activity", J. Am. Chem. Soc. 125:8422-8423.
Kostavasili I., Sahu A., Freidman H. M., Eisenberg R. J., Cohen G. H. and Lambris J. D., 1997, "Mechanism of complement inactivation by glycoprotein C of herpes simplex virus", J. Immunol. 158:1763-71.
Lambiase A et al. "Topical treatment with nerve growth factor in an animal model of herpetic keratitis", Grafes Arch Clin. Exp. Ophthalmol., May 4, 2007.
Lubinski et al., 1998, "Viral interference with antibody and complement", Seminars in Cell & Developmental Biology 9:329-37.
Majumdar S et al., "Dipeptide monoester ganciclovir prodrugs for treating HSV-1-induced corneal epithelial and stromal keratitis: in vitro and in vivo evaluations", J. Ocul. Pharmacol Ther. Dec. 2005; 21(6):463-74.
Manservigi et al., "Immunotherapeutic activity of a recombinant combined gB-gD-gE vaccine against recurrent HSV-2 infections in a guinea pig model." Vaccine. Jan. 4, 2005;23(7):865-72.
Martin et al., 1992, "GAP Domains Responsible for Ras p21-Dependent Inhibition of Muscarinic Atrial K+ Channel Currents", Science 255:192-194.
McLean et al., "Protective vaccination against primary and recurrent disease caused by herpes simplex virus (HSV) type 2 using a genetically disabled HSV-1". J Infect Dis. Nov. 1994;170(5):1100-9.
Mukhlis et al., "Characterization and immunogenicity of HSV-1 antigens obtained following zwitterionic detergent treatment." Vaccine. Sep. 1986;4(3):191-6.
Nagashunmugam et al. 1998. "Human submandibular saliva inhibits human immunodeficiency virus type 1 infection by displacing envelope glycoprotein gp120 from the virus". J Infect Dis 178:1635-41.
Nielsen "Peptide nucleic acids as therapeutic agents". Curr Opin Struct Biol 9:353-57, 1999.
Ouedraogo et al., "Impact of suppressive herpes therapy on genital HIV-1 RNA among women taking antiretroviral therapy: a randomized controlled trial", AIDS, Nov. 28, 2006; 20(18):2305-13.
Rijsewijk et al. "Spontaneous BHV1 recombinants in which the gI/gE/US9 region is replaced by a duplication/inversion of the US1.5/US2 region" Arch Virol. 1999;144(8):1527-37.
Sahu et al., 1996, "Inhibition of human complement by a C3-binding peptide isolated from a phage-displayed random peptide library", J. Immunol. 157:884-891.
Shiau et al. "A simple selection system for construction of recombinant gD-negative pseudorabies virus as a vaccine vector". Vaccine. Jan. 15, 2002;20(7-8):1186-95.
Thi et al., "Rapid determination of antiviral drug susceptibility of herpes simplex virus types 1 and 2 by real-time PCR". Antiviral Res. Mar. 2006;69(3):152-7.
Thompson et al., "Herpes simplex replication and dissemination is not increased by corticosteroid treatment in a rat model of focal Herpes encephalitis". J Neurovirol. Feb. 2000;6(1):25-32.
Dingwell et al. "Glycoproteins E and I facilitate neuron-to-neuron spread of herpes simplex virus." J Virol. Nov. 1995; 69(11): 7087-7098.
Snyder et al. "Herpes Simplex Virus gE/gI and US9 Proteins Promote Transport of both Capsids and Virion Glycoproteins in Neuronal Axons" J. Virol., Nov. 2008; 82:10613-10624.
International Search Report for Application No. PCT/US10/29493 dated May 17, 2010.
European Search Report for Application No. 07837889.0 dated Jul. 29, 2011.
Ashkenazi et al., 1993, "Immunoadhesins", Int. Rev. Immunol. 10(2-3): 219-27.
Sefton, 1987, "Implantable Pumps", CRC Crit. Ref. Biomed. Eng. 14:201.
Zhou "Expression of multiple granzymes by cytotoxic T lymphocyte implies that they activate diverse apoptotic pathways in target cells" Int Rev Immunol. 2010;29(1):38-55.
Aurelian, "Herpes Simplex Virus Type 2: Unique Biological Properties Include Neoplastic Potential Mediated by The Pk Domain of the Large Subunit of Ribonucleotide Reductase", Frontiers in Bioscience, Feb. 15, 1998, 3:d237-249.
Aguilar et al., "Quantitative comparison of the HSV-1 and HSV-2 transcriptomes using DNA microarray analysis", Virology, 2006, 348:233-241.
Basu et al. "Mapping regions of herpes simplex virus type 1 glycoprotein I required for formation of the viral Fc receptor for monomeric IgG.".J Immunol. Jan. 1, 1997 ;158(1):209-15.
Basu et al, "Characterization of Regions of Herpes Simplex Virus Type I Glycoprotein E Involved in Binding the Fc Domain of Monomeric IgC and in Forming a Complex with Glycoprotein I", The journal of Immunology, 1995, 154: 260-267.
Bhuyan et al. "Short interfering RNA-mediated inhibition of herpes simplex virus type 1 gene expression and function during infection of human keratinocytes." J Virol. Oct. 2004;78(19):10276-81.
Dingwell et al, "Herpes simplex virus glycoproteins E and I facilitate cell-to-cell spread in vivo and across junctions of cultured cells", Journal of Virology, Feb. 1994, 68(2):834-845.
Dingwell et al., "The Herpes Simplex Virus gE-gI Complex Facilitates Cell-to-Cell Spread and Binds to Components of Cell Junctions", Journal of Virology, Nov. 1998, 72(11):8933-8942.
Eisenberg et al. "Complement component C3b binds directly to purified glycoprotein C of herpes simplex virus types 1 and 2." Microb Pathog. Dec. 1987;3(6):423-35.
Farnsworth et al., "Herpes Simplex Virus Glycoproteins gD and gE/gI Serve Essential but Redundant Functions during Acquisition of the Virion Envelope in the Cytoplasm", J Virol., Aug. 2003 77(15):8481-8494.
Friedman "Immune evasion by herpes simplex virus type 1, strategies for virus survival." Trans Am Clin Climatol Assoc. 2003;114:103-12.
Friedman et al. "Binding of complement component C3b to glycoprotein gC of herpes simplex virus type 1: mapping of gC-binding sites and demonstration of conserved C3b binding in low-passage clinical isolates." J Virol. Nov. 1986;60(2):470-5.
Friedman et al. "Novel mechanism of antibody-independent complement neutralization of herpes simplex virus type 1." J Immunol. Oct. 15, 2000;165(8):4528-36.
Friedman et al. "Immune evasion properties of herpes simplex virus type 1 glycoprotein gC." J Virol. Jul. 1996;70(7):4253-60.
Fries et al. "Glycoprotein C of herpes simplex virus 1 is an inhibitor of the complement cascade." J Immunol. Sep. 1, 1986;137(5):1636-41.
Gerson et al. "Viral infection of vascular endothelial cells alters production of colony-stimulating activity." J Clin Invest. Oct. 1985;76(4):1382-90.
Harris et al. "Glycoprotein C of herpes simplex virus type 1 prevents complement-mediated cell lysis and virus neutralization." J Infect Dis. Aug. 1990;162(2):331-7.
Hung et al. "Structural basis of C3b binding by glycoprotein C of herpes simplex virus." J Virol. Jul. 1992;66(7):4013-27.

(56) References Cited

OTHER PUBLICATIONS

Hung et al. "The interaction of glycoprotein C of herpes simplex virus types 1 and 2 with the alternative complement pathway." Virology. Sep. 1994;203(2):299-312.
Kostavasili et al. "Mechanism of complement inactivation by glycoprotein C of herpes simplex virus." J Immunol. Feb. 15, 1997;158(4):1763-71.
Lin et al. "Immunization strategies to block the herpes simplex virus type 1 immunoglobulin G Fc receptor." J Virol. Mar. 2004;78(5):2562-71.
Lubinski et al. "Herpes simplex virus type 1 evades the effects of antibody and complement in vivo." J Virol. Sep. 2002;76(18):9232-41.
Neidhardt et al. "Herpes Simplex Virus Type 1 Glycoprotein E is Not Indispensable for Viral Infectivity" J Virol., Feb. 1987, 61(2):600-603.
Polcicova et al., "Herpes keratitis in the absence of anterograde transport of virus from sensory ganglia to the cornea", PNAS Aug. 9, 2005 102(32):11462-11467.
Polcicova et al., "The Extracellular Domain of Herpes Simplex Virus gE is Indispensable for Efficient Cell-to-Cell Spread: Evidence for gE/gI Receptors", Journal of Virology, Sep. 2005, 79(18):11990-12001.
Rux et al. "Kinetic analysis of glycoprotein C of herpes simplex virus types 1 and 2 binding to heparin, heparan sulfate, and complement component C3b." Virology. Mar. 15, 2002;294(2):324-32.
Seidel-Dugan et al. "C3b receptor activity on transfected cells expressing glycoprotein C of herpes simplex virus types 1 and 2." J Virol. Nov. 1988;62(11):4027-36.
Smiley & Friedman "Binding of complement component C3b to glycoprotein C is modulated by sialic acid on herpes simplex virus type 1-infected cells." J Virol. Sep. 1985;55(3):857-61.
Smiley et al. "Herpes simplex virus type 1 infection of endothelial, epithelial, and fibroblast cells induces a receptor for C3b." J Immunol. Apr. 1985;134(4):2673-8.
Sutherland et al. "Herpes simplex virus type 1-encoded glycoprotein C enhances coagulation factor VIIa activity on the virus." Thromb Haemost. Nov. 2004;92(5):947-55.
Tal-Singer et al. "Herpes simplex virus glycoprotein C is a receptor for complement component iC3b." J Infect Dis. Oct. 1991;164(4):750-3.
Weeks & Friedman. "Laminin reduces HSV-1 spread from cell to cell in human keratinocyte cultures." Biochem Biophys Res Commun. Jan. 13, 1997;230(2):466-9.
Weeks et al. "The herpes simplex virus-1 glycoprotein E (gE) mediates IgG binding and cell-to-cell spread through distinct gE domains." Biochem Biophys Res Commun. Jun. 9, 1997;235(1):31-5.
Wisner et al. "The Extracellular Domain of Herpes Simplex Virus gE is Sufficient for Accumulation at Cell Junctions but Not for Cell-to-Cell Spread", Journal of Virology, Mar. 2000,. 74(5):2278-2287.
Witmer et al. "Cytotoxic T lymphocytes specific for herpes simplex virus (HSV) studied using adenovirus vectors expressing HSV glycoproteins." J Gen Virol. Feb. 1990;71 (Pt 2):387-96.
Zajac et al. "Increased adherence of human granulocytes to herpes simplex virus type 1 infected endothelial cells." In Vitro Cell Dev Biol. Apr. 1988;24(4):321-5.
Ziaie et al. "Suppression of matrix protein synthesis by herpes simplex virus type 1 in human endothelial cells." Coll Relat Res. Oct. 1986;6(4):333-49.
Biery et al., "A simple In Vitro Tn7-Based Transposition System With Low Target Site Selectivity for Genome and Gene Analysis." Nucleic Acids Res. 2000 28:1067-1077.
Geerligs et al. "Virus neutralizing activity induced by synthetic peptides of glycoprotein D of herpes simplex virus type 1, selected by their reactivity with hyperimmune sera from mice" Journal of General Virology, 1990, 71:1767-1774.
Ghiasi et al. (1996) "Vaccination with a cocktail of seven recombinantly expressed HSV-1 glycoproteins protects against ocular HSV-1 challenge more efficiently than vaccination with any individual glycoprotein" Vaccine 14:107-112.
Haapa et al., "An efficient and accurate integration of mini-Mu transposons in vitro: a general methodology for functional genetic analysis and molecular biology applications" Nucl. Acids Res. 1999 27: 2777-2784.
Hopp et al., 1988, "A Short Polypeptide Marker Sequence Useful for Recombinant Protein Identification and Purification", Nat. BioTechnology 6:1204-1210.
Hook LM "Herpes simplex virus immune evasion from antibody and complement" (Jan. 1, 2006). Dissertation available from ProQuest, Paper AAI3246168 http://repository.upenn.edu/dissertations/AAI3246168.
Inoue et al. "Preventive effect of local plasmid DNA vaccine encoding gD or gD-IL-2 on herpetic keratitis" Investigative Opthalmology and Visual Science, 2000, 41(13):4209-4215.
Kase et al., 1999, "Human mannan-binding lectin inhibits the infection of influenza A virus without complement", Immunology 97:385-392.
McLean et al., "Induction of a protective immune response by mucosal vaccination with a DISC HSV-1 vaccine", Vaccine 1996, 14(10), 987-92.
Morrison et al., "Influence of mucosal and parenteral immunization with a replication-defective mutant of HSV-2 on immune responses and protection from genital challenge", Virology, 1998, 243(1), 178-87.
NCBI reference sequence NP_044538.1. Dolan, A. Direct Submission, NCBI, Submitted (Feb. 25, 1997) MRC Virology Unit, Church Street, Glasgow; G11 5JR, UK
Para et al., "Similarities and differences in the Fc-binding glycoprotein (gE) of herpes simplex virus types 1 and 2 and tentative mapping of the viral gene for this glycoprotein", J. Virol. 1981, 41(1), 137-44.
Ramaswamy et al., "Interactions and management issues in HSV and HIV coinfection", Expert Rev. Anti Infect Ther. Apr. 2007, 5(2):231-43.
Wagner et al., 1996, "Potent and selective inhibition of gene expression by an antisense heptanucleotide", Nat. Biotechnol. 14:840-844.
European Search Report for Application No. 13151069.5 dated Apr. 15, 2013.
Koelle DM "Vaccines for Herpes Simplex Virus Infections" Curr Opin Investig Drugs. Feb. 2006;7(2):136-41.
Miriagou et al "Expression of the Herpes Simplex Virus Type 1 Glycoprotein E in Human Cells and in *Escherichia coli*: Protection Studies Against Lethal Viral Infection in Mice" J Gen Virol. Dec. 1995;76 ( Pt 12):3137-43.
Stanberry LR "Herpes. Vaccines for HSV" Dermatol Clin. Oct. 1998;16(4):811-6, xiv.
Vogel F R: "Improving Vaccine Performance With Adjuvants" Clin Infect Dis. Jun. 2000;30 Suppl 3:S266-70.
Huemer, H.P., et al., "Cloning and expression of the complement receptor glycoprotein C from *Herpesvirus sirniae* (herpes B virus): protection from complement-mediated cell lysis." Journal of general virology 84.5: 1091-1100.
Lin, Xiaoqing, et al., "Immunization strategies to block the herpes simplex virus type 1 immunoglobulin G Fc receptor," Journal of virology 78.5: 2562-2571 (2004).
Dolan, Aidan, et al. "The genome sequence of herpes simplex virus type 2."Journal of virology 72.3: 2010-2021 (1998).
Tal-Singer, Ruth, et al. "Interaction of herpes simplex virus glycoprotein gC with mammalian cell surface molecules." Journal of virology 69.7: 4471-4483 (1995).
Frink, R. J., et al. "Detailed analysis of the portion of the herpes simplex virus type 1 genome encoding glycoprotein C." *Journal of Virology* 45.2: 634-647 (1983).
Swain, Margaret A., et al. "Characterization of the gene encoding herpes simplex virus type 2 glycoprotein C and comparison with the type 1 counterpart." *Journal of virology* 53.2: 561-569 (1985).
Toh, Y., et al, "Molecular characterization of naturally occurring glycoprotein C-negative herpes simplex virus type 1." *Archives of virology* 129.1-4: 119-130 (1993).

(56) References Cited

OTHER PUBLICATIONS

Dowbenko, Donald J., et al. "Extensive homology between the herpes simplex virus type 2 glycoprotein F gene and the herpes simplex virus type 1 glycoprotein C gene." *Journal of virology* 52.1: 154-163 (1984).

Stanberry, Lawrence R., et al. "Vaccination with recombinant herpes simplex virus glycoproteins: protection against initial and recurrent genital herpes." *Journal of Infectious Diseases* 155.5: 914-920 (1987).

Ashley et al. "Humoral immune response to herpes simplex virus type 2 glycoproteins in patients receiving a glycoprotein subunit vaccine" J Virol. Nov. 1985; 56(2): 475-481.

Awasthi et al. "Immunization with HSV-1 glycoprotein C prevents immune evasion from complement and enhances the efficacy of an HSV-1 glycoprotein D subunit vaccine" Vaccine. Nov. 16, 2009;27(49):6845-53. Epub Sep. 15, 2009.

Bernstein et al. "Safety and Immunogenicity of Glycoprotein D-Adjuvant Genital Herpes Vaccine: Evaluation of HSV-2 gD Vaccine" Clin Infect Dis. May 1, 2005;40(9):1271-81. Epub Mar. 24, 2005.

Bourne et al. "Herpes Simplex Virus (HSV) type 2 glycoprotein D subunit vaccines and protection against genital HSV-1 and HSV-2 disease in guinea pigs", The Journal of Infectious Diseases, 2003,187:542-549.

Brittle et al. "A Replication-Competent, Neuronal Spread-Defective, Live Attenuated Herpes Simplex Virus Type 1 Vaccine" J Virol. Sep. 2008;82(17):8431-41. Epub Jun. 18, 2008.

Carson et al. "Oligonucleotide Adjuvants for T Helper 1 (Th1)-specific Vaccination" J Exp Med. Nov. 17, 1997, 186(10):1621-1622.

Chaves et al. "Loss of Vaccine-Induced Immunity to Varicella over Time", N Engl J Med. Mar. 15, 2007;356(11):1121-9.

Chowdhury et al. "Bovine Herpesvirus 5 (BHV-5) Us9 is Essential for BHV-5 Neuropathogenesis", J Virol. Apr. 2002;76(8):3839-51.

Chowdhury et al. "Bovine Herpesvirus 5 Glycoprotein E is Important for Neuroinvasiveness and Neurovirulence in the Olfactory Pathway of the Rabbit", J Virol. Mar. 2000;74(5):2094-106.

Chowdhury et al. "Neurovirulence of glycoprotein C(gC)-deleted bovine herpesvirus type-5 (BHV-5) and BHV-5 expressing BHV-1 gC in a rabbit seizure model", J Neurovirol. Aug. 2000;6(4):284-95.

Corey et al. "Recombinant Glycoprotein Vaccine for the Prevention of Genital HSV-2 Infection: Two Randomized Controlled Trials" JAMA. 1999;282(4):331-340.

Dolan et al. "The Genome Sequence of Herpes Simplex Virus Type 2", J Virol. Mar. 1998;72(3):2010-21.

Dowler et al. "In vitro neutralization of HSV-2: Inhibition by binding of normal IgG and purified Fc to virion Fc receptor (FcR)" Journal of Medical Virology, 1984 13(3):251-259.

Grabenstein "Drug interactions involving immunologic agents. Part I. Vaccine-vaccine, vaccine-immunoglobulin, and vaccine-drug interactions" DICP. Jan. 1990;24(1):67-81.

Hoshino et al. "Protection from Herpes Simplex Virus (HSV)-2 Infection with Replication-Defective HSV-2 or Glycoprotein D2 Vaccines in HSV-1-Seropositive and HSV-1-Seronegative Guinea Pigs", The Journal of Infectious Diseases 2009 200:1088-95.

Hoshino et al. "Comparative Efficacy and Immunogenicity of Replication-Defective, Recombinant Glycoprotein, and DNA Vaccines for Herpes Simplex Virus 2 Infections in Mice and Guinea Pigs", J Virol. Jan. 2005;79(1):410-8.

Hosken et al. "Diversity of the CD81 T-Cell Response to Herpes Simplex Virus Type 2 Proteins among Persons with Genital Herpes", J Virol. Jun. 2006;80(11):5509-15.

International Preliminary Report on Patentability of Application No. PCT/US2010/029493, dated Oct. 13, 2011.

Johansen et al. "Antagonism between penicillin and erythromycin against *Streptococcus pneumoniae* in vitro and in vivo" J. Antimicrob. Chemother. 2000 46 (6): 973-980.

Kasprowicz et al. "Defining the directionality and quality of influenza virus-specific CD8+ T cell cross-reactivity in individuals infected with hepatitis C virus", J Clin Invest. Mar. 2008;118(3):1143-53.

Koelle et al. "Recent Progress in Herpes Simplex Virus Immunobiology and Vaccine Research", Clin Microbiol Rev. Jan. 2003;16(1):96-113.

McGraw et al. "Anterograde Spread of Herpes Simplex Virus Type 1 Requires Glycoprotein E and Glycoprotein I but Not Us9", J Virol. Sep. 2009;83(17):8315-26. Epub Jul. 1, 2009.

McGraw et al. "Herpes Simplex Virus Type 1 Glycoprotein E Mediates Retrograde Spread from Epithelial Cells to Neurites", J Virol. May 2009;83(10):4791-9.

Meignier et al. "Immunization of experimental animals with reconstituted glycoprotein mixtures of herpes simplex virus 1 and 2: protection against challenge with virulent virus" Infect Dis. May 1987;155(5):pp. 921-930.

Meignier et al. "Virulence of and Establishment of Latency by Genetically Engineered Deletion Mutants of Herpes Simplex Virus I", Virology. Jan. 1988;162(1):251-4.

Mohamedi et al. "A comparison of oral and parenteral routes for therapeutic vaccination with HSV-2 ISCOMs in mice; cytokine profiles, antibody responses and protection" Antiviral Res. Feb. 2001;49(2):83-99.

Nicola et al. "Structure-Function Analysis of Soluble Forms of Herpes Simplex Virus Glycoprotein D", J Virol. Jun. 1996;70(6):3815-22.

Nishiyama et al. "Construction of a US3 lacZ Insertion Mutant of Herpes Simplex Virus Type 2 and Characterization of Its Phenotype in Vitro and in Vivo", Virology. Sep. 1992;190(1):256-68.

Paborsky et al. "Mammalian cell transient expression of tissue factor for the production of antigen", Protein Engineering, 1990 3(6):547-553.

Petrovsky et al. "Vaccine adjuvants: Current state and future trends", Immunol Cell Biol. Oct. 2004;82(5):488-96.

Posavad et al. "Detailed Characterization of T Cell Responses to Herpes Simplex Virus-2 in Immune Seronegative Persons", J Immunol. Mar. 15, 2010;184(6):3250-9. Epub Feb. 17, 2010.

Ramachandran et al. "Potential Prophylactic and Therapeutic Vaccines for HSV Infections", Curr Pharm Des. 2007;13(19):1965-73.

Saiki et al. "Primer-Directed Enzymatic Amplification of DNA with a Thermostable DNA Polymerase", Science. Jan. 29, 1988;239(4839):487-91.

Saudek et al. "A Preliminary Trial of the Programmable Implantable Medication System for Insulin Delivery", N. Engl. J. Med. 1989 321:574.

Simms et al. "Use of herpes simplex virus (HSV) type 1 ISCOMS 703 vaccine for prophylactic and therapeutic treatment of primary and recurrent HSV-2 infection in guinea pigs" Sheffield Institute for Vaccine Studies, Division of Molecular and Genetic Medicine, Section of Infection and Immunity, University of Sheffield Medical School, Sheffield, United Kingdom, J Infect Dis. Apr. 2000;181(4):1240-8. Epub; Apr. 13, 2000.

Stanberry: "Clinical Trials of Prophylactic and Therapeutic Herpes Simplex Virus Vaccines" Herpes 2004 11 Supplement 3: 161A-169A.

Tan et al. "Advances in the Development of Vaccines against *Neisseria meningitides*" N Engl J Med Apr. 22, 2010; 362:1511-1520.

Xu et al. "The orthopoxvirus type I IFN binding protein is essential for virulence and an effective target for vaccination" J Exp Med. Apr. 14, 2008; 205(4): 981-992.

Zoller et al. "Oligonucleotide-directed mutagenesis using M13-derived vectors: an efficient and general procedure for the production of point mutations in any fragment of DNA", Nucleic Acids Res. Oct. 25, 1982;10(20):6487-500.

\* cited by examiner

| Vaccine Dose | Right Ganglia (Side Vaccination Given) | Left Ganglia (Side Challenge Given) |
|---|---|---|
| 5 X 10⁵ pfu | 0 OF 5 | 1 OF 5 |
| 5 X 10⁴ pfu | 0 OF 5 | 0 OF 5 |
| 5 X 10³ pfu | 0 OF 5 | 0 OF 5 |

ALIGNMENT OF HSV-1(NS) gE (SEQ ID NO: 2) with HSV-2 (HG52) gE (SEQ ID NO: 6)

72.6% IDENTITY IN 552 RESIDUES OVERLAP; SCORE: 2048.0; GAP FREQUENCY: 1.3%

```
HSV-1(NS)gE       1  MDRGAVVGFLLGVCVVSCLAGTPKTSWRRVSVGEDVSLLPAPGPTGRGPTQKLLWAVEPL
HSV-2(HG52)gE     1  MARGAGLVFFVGVWVVSCLAAAPRTSWKRVTSGEDVVLLPAPAERTRA--HKLLWAAEPL
                     * ***   *  ** ******  * *** **  **** *****    *    ***** ***

HSV-1(NS)gE      61  DGCGPLHPSWVSLMPPKQVPETVVDAACMRAPVPLAMAYAPPAPSATGGLRTDFVWQERA
HSV2(HG52)gE     59  DACGPLRPSWVALWPPRRVLETVVDAACMRAPEPLAIAYSPPFPAGDEGLYSELAWRDRV
                     * **** **** * **  * ************ *** ** ** *    **     *  *

HSV-1(NS)gE     121  AVVNRSLVIYGVRETDSGLYTLSVGDIKDPARQVASVVLVVQPAPVPTPPPTPADYDEDD
HSV-2(HG52)gE   119  AVVNESLVIYGALETDSGLYTLSVVGLSDEARQVASVVLVVEPAPVPTP--TPDDYDEED
                     **** ******  ***********    * *********** *******  ** **** *

HSV-1(NS)gE     181  NDEGEGEDESLAGTPASGTPRLPPSPAPPRSWPSAPEVSHVRGVTVRMETPEAILFSPGE
HSV-2(HG52)gE   177  --DAGVTNARRSAFPPQPPPRRPPV-APPTHPRVIPEVSHVRGVTVHMETLEAILFAPGE
                                   *    ** **  ***      *********** *** ***** ***
```

FIG.24A

```
HSV-1(NS)gE   241  AFSTNVSIHAIAHDDQTYTMDVVWLRFDVPTSCAEMRIYESCLYHPQLPECLSPADAPCA
HSV-2(HG52)gE 234  TFGTNVSIHAIAHDDGPYAMDVVWMRFDVPSSCADMRIYEACLYHPQLPECLSPADAPCA
                   ************************ ***** **** ****** **************

HSV-1(NS)gE   301  ASTWTSRLAVRSYAGCSRTNPPPRCSAEAHMEPFPGLAWQAASVNLEFRDASPQHSGLYL
HSV2(HG52)gE  294  VSSWAYRLAVRSYAGCSRTTPPPRCFAEARMEPVPGLAWLASTVNLEFQHASPQHAGLYL
                    * *  ************ ***** *** *** ***** **  *** *  ***** ***

HSV-1(NS)gE   361  CVVYVNDHIHAWGHITINTAAQYRNAVVEQPLPQRGADLAEPTHPHVGAPPHAPPTHGAL
HSV-2(HG52)gE 354  CVVYVDDHIHAWGHMTISTAAQYRNAVVEQHLPQRQPEPVEPTRPHVRAPHPAPSARGPL
                   ***** ******** ** ************ ***     *** *** **  ** ** *

HSV-1(NS)gE   421  RLGAVMGAALLLSALGLSVWACMTCWRRRAWRAVKSRASGKGPTYIRVADSELYADWSSD
HSV-2(HG52)gE 414  RLGAVLGAALLLAALGLSAWACMTCWRRRSWRAVKSRASATGPTYIRVADSELYADWSSD
                   ***** ****** ***** ********* *********  *******************

HSV-1(NS)gE   481  SEGERDQVPWLAPPERPDSPSTNGSGFEILSPTAPSVYPRSDGHQSRRQLTTFGSGRPDR
HSV-2(HG52)gE 474  SEGERDGSLWQDPPERPDSPSTNGSGFEILSPTAPSVYPHSEGRKSRRPLTTFGSGSPGR
                   ******   *  ************************** *  * *** ******  *

HSV-1(NS)gE   541  RYSQASDSSVFW
HSV-2(HG52)gE 534  RHSQASYPSVLW
                   * ****   ** *
```

FIG. 24A (cont)

| DNA Identity | Length | Region Within Published HSV-2 (HG52) Genome |
|---|---|---|
| HSV-2 (2.12) IGR58 | 300 | 143551-143842 |
| HSV-2 (2.12) Us8 (gE-5'end) | 369 | 143843-144209 |
| pBluescript SK+Mult.Clon.Site | 19 | N/A |
| HSV-2 (2.12) Us8 (gE-3'end) | 156 | 145325-145480 |
| HSV-2 (2.12) Us8A | 288 | 145481-145769 |
| HSV-2 (2.12) IGR59 | 97 | 145770-145866 |

Days post-inoculation

KOS  rKOS-gDA3C  KOS-gDA3C

HSV-1 AND HSV-2 VACCINES AND METHODS OF USE THEREOF

CROSS-REFERENCE TO RELATED APPLICATIONS

This application is a National Phase Application of PCT International Application No. PCT/US07/19537, International Filing Date Sep. 7, 2007, claiming priority of U.S. Provisional Patent Applications, 60/842,947, filed Sep. 7, 2006, and 60/929,050, filed Jun. 11, 2007, all of which are incorporated herein by reference in their entirety.

STATEMENT REGARDING FEDERALLY SPONSORED RESEARCH OR DEVELOPMENT

The invention described herein was supported in whole or in part by grants from the National Institutes of Health (Grant No. R01AI33063). The government has certain rights in the invention.

FIELD OF INVENTION

This invention provides methods of vaccinating a subject against Herpes Simplex Virus (HSV) infection and disorders and symptoms associated with same, and impeding, inhibiting, reducing the incidence of, and suppressing HSV infection, neuronal viral spread, formation of zosteriform lesions, herpetic ocular disease, herpes-mediated encephalitis, and genital ulcer disease in a subject, comprising the step of contacting the subject with a mutant strain of the HSV, containing an inactivating mutation in a gene encoding a gE, gI, Us9, or other protein, optionally containing an inactivating mutation in a gene encoding a gD.

BACKGROUND OF THE INVENTION

Human infection with herpes simplex virus (HSV) type 1 or 2 is typically acquired through intimate contact and causes oral and genital lesions. HSV-1 usually causes oral ulcers and HSV-2 normally causes genital ulcers, but the reverse can also occur. A person infected with HSV-1 or HSV-2 will always be a carrier of the virus. After initial infection, lesions heal and HSV exists in a dormant, latent state in sensory neurons. Periodically, HSV reactivates from latently infected neurons and causes new ulcers to form at the skin surface. Newborn infants and immunosuppressed individuals are particularly vulnerable to HSV infection, often having a disseminated infection with fatal results. Ocular HSV infection, a leading cause of blindness, is another serious consequence of the virus. Furthermore, genital HSV infection results in a two-fold increase in HIV transmission rate. Therefore, a vaccine to prevent transmission of HSV is urgently needed.

SUMMARY OF THE INVENTION

This invention provides methods of vaccinating a subject against a Herpes Simplex Virus (HSV) infection and disorders and symptoms associated with same, and impeding, inhibiting, reducing the incidence of, and suppressing HSV infection, neuronal viral spread, formation of zosteriform lesions, herpetic ocular disease, herpes-mediated encephalitis, and genital ulcer disease in a subject, comprising the step of contacting the subject with a mutant strain of the HSV, containing an inactivating mutation in a gene encoding a gE, gI, Us9, or other protein.

In another embodiment, the present invention provides method of treating, reducing the pathogenesis of, ameliorating the symptoms of, ameliorating the secondary symptoms of, reducing the incidence of, prolonging the latency to a relapse of a Herpes Simplex Virus (HSV) infection in a subject, comprising the step of contacting said subject with a composition comprising a mutant Herpes Simplex Virus vaccine strain, wherein said mutant HSV vaccine strain comprises an inactivating mutation in a Us8 gene. In one embodiment, the mutant HSV vaccine strain is an HSV-1 strain, while in another embodiment, the mutant HSV vaccine strain is an HSV-2 strain. In one embodiment, the HSV infection is an HSV-1 infection, while in another embodiment, the HSV infection is an HSV-2 infection.

In one embodiment, the mutant strain is replication-competent in the skin tissue of said subject. In one embodiment, the neuronal viral spread of said mutant strain is impeded.

In one embodiment, the mutant HSV vaccine strain further comprises an additional inactivating mutation in a Us7 gene, or, in another embodiment, in a Us9 gene, or, in another embodiment, in both Us7 and Us9 genes. In one embodiment, the mutant HSV vaccine strain further comprises an additional inactivating mutation in a gene encoding a membrane protein not required for virus entry, which in one embodiment, is Us5, in another embodiment, Us4, in another embodiment, UL53, in another embodiment, UL10, or in another embodiment, any combination of Us5, Us4, UL53, and UL10. In one embodiment, the mutant HSV vaccine strain further comprises an additional inactivating mutation in a gene encoding a membrane protein required for virus entry, which in one embodiment, is Us6.

In one embodiment, the HSV infection is a genital HSV infection, while in another embodiment, the HSV infection is HSV encephalitis, while in another embodiment, the HSV infection is an ocular disease, while in another embodiment, the HSV infection is HSV labialis, while in another embodiment, the HSV infection is any combination of the above.

In one embodiment, the subject is infected by HSV, while in another embodiment, the subject is at risk for infection by HSV, which in one embodiment, is a subject who is a neonate, in another embodiment, immunocompromised, in another embodiment, elderly, and in another embodiment, an immunocompromised neonate or an immunocompromised elderly subject.

In one embodiment, the method induces an anti-HSV immune response in a subject, which in one embodiment, is an anti-HSV neutralizing antibody response.

In one embodiment, the step of contacting comprises epidermal injection, in another embodiment, intramuscular injection, in another embodiment, subcutaneous injection, and in another embodiment, intra-respiratory mucosal injection.

In one embodiment, the present invention provides an isolated mutant HSV-1 strain comprising a first inactivating mutation in a gene encoding a gE protein and a second inactivating mutation. In another embodiment, the gene encoding a gE protein is a Us8 gene. In another embodiment, the second inactivating mutation is in a Us7 gene. In another embodiment, the second inactivating mutation is in a Us9 gene. In another embodiment, the second inactivating mutation is in any other HSV-1 gene known in the art. In another embodiment, the isolated mutant HSV-1 strain contains inactivating mutations in genes encoding a gE protein, a gI protein, and a Us9 protein.

In another embodiment, the present invention provides an isolated mutant HSV-2 strain comprising a first inactivating mutation in a gene encoding a gE protein and one or more additional inactivating mutations. In one embodiment, the gene encoding a gE protein is a Us8 gene. In one embodiment, the additional inactivating mutation is in a membrane protein not required for virus entry. In another embodiment, the additional inactivating mutation is in a Us7 gene. In another embodiment, the additional inactivating mutation is in a Us9 gene. In another embodiment, the additional inactivating mutation is in Us5, Us4, UL53, UL10, or a combination thereof. In one embodiment, the additional inactivating mutation is in a membrane protein required for virus entry. In another embodiment, the additional inactivating mutation is in Us6. In another embodiment, the additional inactivating mutation is in any other HSV-2 gene known in the art. In another embodiment, the isolated mutant HSV-2 strain contains inactivating mutations in genes encoding a gE protein, a gI protein, and a Us9 protein.

BRIEF DESCRIPTION OF THE FIGURES

FIG. 1. HSV spread in neurons.

FIG. 2. Typical HSV-1 infection of a mouse flank.

FIG. 3. Spectrum of skin disease in the mouse flank/vaccination model.

FIG. 4. Survival of mice following infection with HSV-$1_{(gE\ null)}$ vaccine or virulent HSV-$1_{(Rescue\ gE\ null)}$.

FIG. 5. Primary skin disease after infection with HSV-$1_{(gE\ null)}$ vaccine or virulent HSV-$1_{(Rescue\ gE\ null)}$.

FIG. 6. Secondary (zosteriform) skin disease after infection with HSV-$1_{(gE\ null)}$ vaccine or virulent HSV-$1_{(Rescue\ gE\ null)}$.

FIG. 7. Viral titers in skin after infection with vaccine or virulent HSV-1.

FIG. 8. HSV detection in skin after infection with vaccine or wild-type HSV-1.

FIG. 9. Viral titers in dorsal root ganglia (DRG) after infection with vaccine or virulent HSV-1.

FIG. 10. Survival of vaccinated or mock-vaccinated mice following challenge with $10^5$ pfu of WT HSV-1 (NS).

FIG. 11. Primary skin disease scores in vaccinated mice challenged with $10^5$ pfu of WT HSV-1 (NS).

FIG. 12. Viral titers in skin in vaccinated mice challenged with $10^5$ pfu of WT HSV-1 (NS).

FIG. 13. HSV detection in skin of mock-vaccinated or vaccinated mice, challenged with $10^5$ pfu of WT HSV-1 (NS).

FIG. 14. Secondary skin disease in vaccinated mice challenged with $10^5$ pfu of WT HSV-1 (NS). N=3.

FIG. 15. Viral titers of ganglia from mock-vaccinated or vaccinated mice, challenged with $10^5$ pfu of WT HSV-1 (NS). N=3.

FIG. 16. Vaccine protects ganglia from latent infection.

FIG. 17. Cross protection of mice vaccinated with $5\times10^5$ pfu HSV-1ΔgE against flank challenge with $10^5$ pfu HSV-2 (2.12). "Mock Vac" denotes mock vaccination; "DgE Vac" denotes vaccination with $5\times10^5$ pfu HSV-1ΔgE. Error bars represent the Standard Error of the Mean ("SEM").

FIG. 18. Protection of mice vaccinated with $5\times10^5$ pfu HSV-1ΔgE against latency following flank challenge with $5\times10^5$ pfu HSV-1(KOS). Error bars represent the SEM.

FIG. 19. Protection of mice vaccinated with $5\times10^5$ pfu HSV-1ΔgE against death, visible Disease and Extensive Viral Replication Following Vaginal Challenge with $10^5$ pfu HSV-1(NS). A. Top panel-survival curves; bottom panel-viral titer as assessed by vaginal swabs. B. Photographs of mice on day 8 post-challenge. Error bars: SEM.

FIG. 20. Protection of mice vaccinated with $5\times10^5$ pfu HSV-1ΔgE by different routes ("Ep. Scar.": epidermal scarification; "SubQ": subcutaneously; IM: intramuscular) against flank challenge with $10^5$ pfu HSV-1(NS). "DgE Vac" denotes HSV-1ΔgE; Error bars represent the SEM.

FIG. 21. Induction of neutralizing antibody response in mice vaccinated with $5\times10^5$ pfu HSV-1ΔgE by different routes. Percentages depicted are compared to serum from mock-vaccinated mice. n=3 (Ep. Scar & Sub Q), n=2 (IM), assays were done in duplicate. Error bars represent the SEM.

FIG. 22. Protection of mice vaccinated with $5\times10^5$ pfu HSV-1 ΔgE against flank challenge with $10^5$ pfu HSV-1(NS, For 17). Error bars represent the SEM.

FIG. 23. Protection of mice vaccinated with $5\times10^5$ pfu HSV-1ΔgE against flank challenge with $10^{5-7}$ pfu HSV-1 (NS). Error bars represent the SEM.

FIG. 24. A. Alignment of HSV-1(NS) gE (SEQ ID NO: 2) with HSV-2(HG52) gE (SEQ ID NO: 6) B. Strategy for generation of gE-2 deletion.

FIG. 25. Additional deletions to the Us region. Schematic diagram of the 4.5 kb region within the Us segment of the HSV-2 genome (155 kb total genome size) is depicted. The region equivalent to that deleted in the HSV-1ΔgE vaccine strain and area of proposed additional deletions are noted.

FIG. 26. A. Western blot to detect gD (Us6) and gI (Us7) in infected cell extracts. B. Stability of the KOS-gDA3C virus in vitro. An Ssp1 digest of a PCR-amplified gD gene fragment of KOS or KOS-gDA3C. C. Stability of the KOS-gDA3C mutant virus in vivo. A PCR-amplified gD fragment obtained from the DRG of KOS-gDA3C-infected mice were cut with Ssp1 or left uncut.

FIG. 27. Entry of KOS, rKOS-gDA3C and KOS-gDA3C virus into (A) Vero, (B) B78-H1, (C) A10 or (D) C10 cells. Results are the mean±SE of three separate infections each done in triplicate.

FIG. 28. Single-step (A, B) and multi-step (C, D) growth curves of KOS, rKOS-gDA3C and KOS-gDA3C performed in A10 (A, C) or C10 (B, D) cells. Results are the mean±SE of three separate infections.

FIG. 29. Disease in the murine flank model. Inoculation (A) and zosteriform (B) site disease scores in mice inoculated with $5\times10^5$ PFU of KOS, rKOS-gDA3C or KOS-gDA3C. Error bars represent SE. C. Photographs of mice flanks taken 10 days post-infection with KOS, rKOS-gDA3C, or KOS-gDA3C.

FIG. 30. Virus titers and genome copy numbers in DRG. DRG were dissected from mice infected with KOS, rKOS-gDA3C or KOS-gDA3C and assayed for virus titers (A) or viral genome copy number (B). Results represent the mean±SE.

FIG. 31. Prior infection with KOS-gDA3C protects against WT HSV-1 challenge. Results represent mean disease scores+SE at the inoculation (A) and zosteriform (B) sites from days 3-7 post-infection. DRG viral titers (C) and genome copy number (D) were measured 5 days post-challenge with NS. Results represent the mean+SE.

FIG. 32. Model for KOS-gDA3C infection in mice. KOS infects epithelial cells (E) and produces disease at the inoculation site. The virus spreads to neurons (N) in the DRG, replicates and spreads to adjacent neurons and then travels back to epithelial cells in the skin to cause zosteriform disease. KOS-gDA3C is impaired in entry and infects fewer epithelial cells, which results in fewer neurons becoming infected in the DRG. The defect in entry also reduces infection of adjacent neurons in the DRG and results in reduced zosteriform disease.

DETAILED DESCRIPTION OF THE INVENTION

This invention provides methods of vaccinating a subject against Herpes Simplex Virus (HSV) infection and disorders and symptoms associated with same, and impeding, inhibiting, reducing the incidence of, and suppressing HSV infection, neuronal viral spread, formation of zosteriform lesions, herpetic ocular disease, herpes-mediated encephalitis, and genital ulcer disease in a subject, comprising the step of contacting the subject with a mutant strain of the HSV, containing an inactivating mutation in a gene encoding a gE, gI, Us9, other protein, or combinations thereof. In another embodiment, the mutant strain of the HSV, comprises an inactivating mutation in a gene encoding gE, which in one embodiment, is a gE null mutation. In another embodiment, the present invention provides pharmaceutical compositions comprising a mutant strain of HSV which comprises an inactivating mutation in a gene encoding gE, which in one embodiment, is a gE null mutation. In another embodiment, this invention provides pharmaceutical compositions comprising a mutant strain of HSV which comprises an inactivating mutation in a gene encoding a gE, gI, Us9, other protein, or combinations thereof.

In one embodiment, the present invention provides a method of vaccinating a subject against an HSV infection, comprising the step of contacting the subject with a mutant HSV strain, wherein the mutant strain contains an inactivating mutation in a Us8 gene encoding a gE protein.

In another embodiment, the present invention provides a method of impeding HSV-1 infection in a subject, comprising the step of contacting the subject with a mutant HSV strain, wherein the mutant strain contains an inactivating mutation in a Us8 gene encoding a gE protein.

In another embodiment, the present invention provides a method of impeding HSV-2 infection in a subject, comprising the step of contacting the subject with a mutant HSV strain, wherein the mutant strain contains an inactivating mutation in a Us8 gene encoding a gE protein.

In another embodiment, the present invention provides a method of impeding primary HSV infection in a subject, comprising the step of contacting the subject with a mutant HSV strain, wherein the mutant strain contains an inactivating mutation in a Us8 gene encoding a gE protein. In another embodiment, the present invention provides a method of impeding primary HSV-1 infection in a subject, comprising the step of contacting the subject with a mutant HSV strain, wherein the mutant strain contains an inactivating mutation in a Us8 gene encoding a gE protein In another embodiment, the present invention provides a method of impeding primary HSV-2 infection in a subject, comprising the step of contacting the subject with a mutant HSV strain, wherein the mutant strain contains an inactivating mutation in a Us8 gene encoding a gE protein The terms "impeding HSV infection" and "impeding primary HSV infection" refer, in one embodiment, to decreasing the titer of infectious virus by 90%. In another embodiment, the titer is decreased by 50%. In another embodiment, the titer is decreased by 55%. In another embodiment, the titer is decreased by 60%. In another embodiment, the titer is decreased by 65%. In another embodiment, the titer is decreased by 70%. In another embodiment, the titer is decreased by 75%. In another embodiment, the titer is decreased by 80%. In another embodiment, the titer is decreased by 85%. In another embodiment, the titer is decreased by 92%. In another embodiment, the titer is decreased by 95%. In another embodiment, the titer is decreased by 96%. In another embodiment, the titer is decreased by 97%. In another embodiment, the titer is decreased by 98%. In another embodiment, the titer is decreased by 99%. In another embodiment, the titer is decreased by over 99%.

In another embodiment, the terms refer to decreasing the extent of viral replication by 90%. In another embodiment, replication is reduced by 50%. In another embodiment, replication is reduced by 55%. In another embodiment, replication is reduced by 60%. In another embodiment, replication is reduced by 65%. In another embodiment, replication is reduced by 70%. In another embodiment, replication is reduced by 75%. In another embodiment, replication is reduced by 80%. In another embodiment, replication is reduced by 85%. In another embodiment, replication is reduced by 92%. In another embodiment, replication is reduced by 95%. In another embodiment, replication is reduced by 96%. In another embodiment, replication is reduced by 97%. In another embodiment, replication is reduced by 98%. In another embodiment, replication is reduced by 99%. In another embodiment, replication is reduced by over 99%.

Methods for measuring HSV infection are well known in the art, and include, in one embodiment, determination of appearance and severity of skin lesions and viral-mediated illness (Examples 1 and 4). Other embodiments of methods for measuring viral infection are described, for example, in Burgos J S et al. (Herpes simplex virus type 1 infection via the bloodstream with apolipoprotein E dependence in the gonads is influenced by gender. J Virol. 2005 February; 79(3): 1605-12) and Parr M B et al. (intravaginal administration of herpes simplex virus type 2 to mice leads to infection of several neural and extraneural sites. J. Neurovirol. 2003 December; 9(6):594-602). Other methods of determining the extent of HSV replication and HSV infection are well are described, for example, in Lambiase A et al. (Topical treatment with nerve growth factor in an animal model of herpetic keratitis. Graefes Arch Clin Exp Ophthalmol. 2007 May 4), Ramaswamy M et al. (Interactions and management issues in HSV and HIV coinfection. Expert Rev Anti Infect Ther. 2007 April; 5(2):231-43), and Jiang C et al. (Mutations that decrease DNA binding of the processivity factor of the herpes simplex virus DNA polymerase reduce viral yield, alter the kinetics of viral DNA replication, and decrease the fidelity of DNA replication. J. Virol. 2007 April; 81(7):3495-502).

As provided herein, vaccination with gE-null HSV strains of the present invention protects against subsequent infection with virulent HSV. In another embodiment, the vaccination protects against disease caused by virulent HSV. In another embodiment, the vaccine strain does not itself cause significant disease, which in one embodiment is herpes (Examples 1 and 4), or, in another embodiment, result in significant symptomology.

“Inactivating mutation” in gE refers, in one embodiment, to a mutation that abrogates HSV neuronal spread. In another embodiment, the terms refer to a mutation that abrogates cell-to-cell spread of HSV. In another embodiment, the terms refer to abrogation of spread along axons. In another embodiment, the spread is retrograde (defined herein below). In another embodiment, the spread is anterograde (defined herein below). In another embodiment, spread in both anterograde and retrograde directions is abrogated.

In one embodiment, neuronal spread is decreased by 90%. In another embodiment, neuronal spread is decreased by 60%. In another embodiment, the reduction is 65%. In another embodiment, the reduction is 70%. In another embodiment, the reduction is 75%. In another embodiment, the reduction is 80%. In another embodiment, the reduction is 85%. In another embodiment, the reduction is 95%. In another embodiment, the reduction is 96%. In another embodiment, the reduction is 97%. In another embodiment, the reduction is 98%. In another embodiment, the reduction is 99%. In another embodiment, the reduction is over 99%.

In one embodiment, the term refers to abrogating ability of gE protein to sequester host anti-HSV antibodies. In another embodiment, sequestration of anti-HSV antibodies by gE is reduced by 90%. In another embodiment, sequestration is reduced by 50%. In another embodiment, the reduction is 65%. In another embodiment, the reduction is 70%. In another embodiment, the reduction is 75%. In another embodiment, the reduction is 80%. In another embodiment, the reduction is 85%. In another embodiment, the reduction is 95%. In another embodiment, the reduction is 96%. In another embodiment, the reduction is 97%. In another embodiment, the reduction is 98%. In another embodiment, the reduction is 99%. In another embodiment, the reduction is over 99%.

In one embodiment, the term refers to abrogating ability of gE protein to bind IgG monomers. In another embodiment, binding of IgG monomers by gE is reduced by 90%. In another embodiment, binding is reduced by 50%. In another embodiment, the reduction is 65%. In another embodiment, the reduction is 70%. In another embodiment, the reduction is 75%. In another embodiment, the reduction is 80%. In another embodiment, the reduction is 85%. In another embodiment, the reduction is 95%. In another embodiment, the reduction is 96%. In another embodiment, the reduction is 97%. In another embodiment, the reduction is 98%. In another embodiment, the reduction is 99%. In another embodiment, the reduction is over 99%.

In one embodiment, the term refers to abrogating ability of gE protein to bind IgG complexes. In another embodiment, binding of IgG complexes by gE is reduced by 90%. In another embodiment, binding is reduced by 50%. In another embodiment, the reduction is 65%. In another embodiment, the reduction is 70%. In another embodiment, the reduction is 75%. In another embodiment, the reduction is 80%. In another embodiment, the reduction is 85%. In another embodiment, the reduction is 95%. In another embodiment, the reduction is 96%. In another embodiment, the reduction is 97%. In another embodiment, the reduction is 98%. In another embodiment, the reduction is 99%. In another embodiment, the reduction is over 99%.

In one embodiment, an inactivating mutation in gE comprises a deletion of amino acids 124-508. In another embodiment, an inactivating mutation in gE comprises a deletion of amino acids 110-500. In another embodiment, an inactivating mutation in gE comprises a deletion of amino acids 1-552. In another embodiment, an inactivating mutation in gE comprises a deletion of amino acids 1-50. In another embodiment, an inactivating mutation in gE comprises a deletion of amino acids 1-100. In another embodiment, an inactivating mutation in gE comprises a deletion of amino acids 1-250. In another embodiment, an inactivating mutation in gE comprises a deletion of amino acids 100-300. In another embodiment, an inactivating mutation in gE comprises a deletion of amino acids 1-400. In another embodiment, an inactivating mutation in gE comprises a deletion of amino acids 200-500. In another embodiment, an inactivating mutation in gE comprises a deletion of amino acids 24-71. In another embodiment, an inactivating mutation in gE comprises a deletion of amino acids 30-508. In another embodiment, an inactivating mutation in gE comprises a deletion of approximately amino acids 40-70. In another embodiment, an inactivating mutation in gE comprises insertion of a non-native sequence into a portion of the gene encoding gE, wherein said gE is inactivated as a result. In another embodiment, an inactivating mutation in gE comprises substitution of amino acid residues, such as a substitution of polar for non-polar residues, non-polar for polar residues, charged for uncharged residues, positively charged for negatively charged residues, or vice versa, or a combination thereof, as is known to one of skill in the art. In another embodiment, an inactivating mutation in gE consists essentially of any of the mutations listed hereinabove. In another embodiment, an inactivating mutation in gE consists of any of the mutations listed hereinabove. In another embodiment, an inactivating mutation in gE or other protein as described in the instant invention for a first HSV strain may also be mutated in an equivalent location of the corresponding protein in a second HSV strain, wherein the equivalent location of the insertion, deletion or substitution may be inferred by sequence alignment, as is well known in the art, wherein the region that aligns with the sequence of the mutation in the first strain would be mutated in the second strain.

"Inactivating mutation" in gD refers, in one embodiment, to a mutation that inhibits protein/receptor interactions, which in one embodiment is an interaction with a HVEM cell receptor, a nectin-1 cell receptor, or both, and in another embodiment, to a mutation that inhibits viral entry into a cell, inhibits downstream activation of gB, gH, and gL, inhibits fusion of the viral envelope with cell membrane, or a combination thereof. In one embodiment, an inactivating mutation in gD is in the amino terminus of the gD peptide, which in one embodiment is residue 1-15, and in another embodiment, the mutation inhibits formation of a hairpin loop structure when gD is bound to HVEM. In another embodiment, the mutation is at amino acids 3, 38, or both, and in one embodiment, alanine and tyrosine residues at those locations are replaced with cysteine residues (A3C/Y38C) to create a 3-38 disulfide bond and/or a fixed hairpin loop at the amino terminus.

In one embodiment, inactivating mutations of the present invention are accomplished using tools known in the art. In one embodiment, the nucleic acids used in this invention and those encoding proteins of and for use in the methods of the present invention can be produced by any synthetic or recombinant process such as is well known in the art. Nucleic acids can further be modified to alter biophysical or biological properties by means of techniques known in the art. For example, the nucleic acid can be modified to increase its stability against nucleases (e.g., "end-capping"), or to modify its lipophilicity, solubility, or binding affinity to complementary sequences. In another embodiment, transposons may be used to create inactivating mutations of a gene, where in one embodiment, the transposon may be Tn551, Minos, Hermes or piggyback. In another embodiment, the transposon may be AT-2 (tyl based transposon, Perkin Elmer; Devine et al. (1997) Genome Res. 7:551-563), GPS-1 (New England Biolabs), GPS-2 (New England Biolabs), EZ::tn (Tn5 based transposon, Epicenter Technologies), SIP (Tn7 based transposon, Biery et al. (2000) Nucl Acid Res 28:1067-1077), or Mu (Finnzymes, Haapa et al. (1999) Nucl Acid Res 13:2777-2784). In one embodiment, Southern blot analysis of digested DNA from individual transposon mutants may be used to verify transposon insertion. In another embodiment, sequence analysis, PCR and/or hybridization may be utilized to determine transposon insertion. Mutations may also be elicited using ethylmethanesulfonate (EMS) or radiation. In another embodiment, mutagenesis with chemical agents may be used. Such chemical mutagens may comprise, in other embodiments, chemicals that affect nonreplicating DNA such as $HNO_2$ and $NH_2OH$, as well as agents that affect replicating DNA such as acridine dyes, which have been shown to cause frameshift mutations. Methods for creating mutants using radiation or chemical agents are well known in the art, and any method may be utilized for the methods of this invention (see, for example, Thomas D. Brock in Biotechnology: A Textbook of Industrial Microbiology, Second Edition (1989) Sinauer Associates, Inc., Sunderland, Mass., or Deshpande, Mukund V., Appl. Biochem. Biotechnol. 36, 227 (1992).

In one embodiment, DNA can be synthesized chemically from the four nucleotides in whole or in part by methods known in the art. Such methods include those described in Caruthers (1985; Science 230:281-285). DNA can also be synthesized by preparing overlapping double-stranded oligonucleotides, filling in the gaps, and ligating the ends together (see, generally, Sambrook et al. (1989; *Molecular Cloning—A Laboratory Manual, 2nd Edition*. Cold Spring Habour Laboratory Press, New York)). In another embodiment, inactivating mutations may be prepared from wild-type DNA by site-directed mutagenesis (see, for example, Zoller et al. (1982; DNA. 1984 December; 3(6):479-88); Zoller (1983); and Zoller (1984; DNA. 1984 December; 3(6):479-88); McPherson (1991; Directed Mutagenesis: A Practical Approach. Oxford University Press, NY)). The DNA obtained can be amplified by methods known in the art. One suitable method is the polymerase chain reaction (PCR) method described in Saiki et al. (1988; Science. 1988 Jan. 29; 239(4839):487-491), Mullis et al., U.S. Pat. No. 4,683,195, and Sambrook et al. (1989).

In one embodiment, the present invention provides a method of impeding the establishment of a latent HSV infection in a subject, comprising the step of contacting the subject with a mutant HSV strain, wherein the mutant strain contains an inactivating mutation in a Us8 gene encoding a gE protein. In another embodiment, the latent HSV infection that is prevented follows primary HSV infection. In another embodiment, the subject has been infected with HSV before vaccination. In another embodiment, the subject is at risk for HSV infection. In another embodiment, whether or not the subject has been infected with HSV at the time of vaccination, vaccination by a method of the present invention is efficacious in protecting a subject against latent HSV infection, following primary HSV infection.

In one embodiment, the present invention provides a method of inhibiting an HSV flare in a subject, comprising the step of contacting the subject with a mutant HSV strain, wherein the mutant strain contains an inactivating mutation in a Us8 gene encoding a gE protein. In another embodiment, the flare that is prevented follows exposure of the subject to HSV. In another embodiment, the subject has been infected with HSV before vaccination. In another embodiment, the subject is at risk for HSV infection. In another embodiment, whether or not the subject has been infected with HSV at the time of vaccination, vaccination by a method of the present invention is efficacious in protecting a subject against a formation of a flare, following an exposure of the subject to HSV.

In one embodiment, the present invention provides a method of protecting a subject against an HSV flare, comprising the step of contacting the subject with a mutant HSV strain, wherein the mutant strain contains an inactivating mutation in a Us8 gene encoding a gE protein. In another embodiment, the flare that is prevented follows exposure of the subject to HSV. In another embodiment, the subject has been infected with HSV before vaccination. In another embodiment, the subject is at risk for HSV infection. In another embodiment, whether or not the subject has been infected with HSV at the time of vaccination, vaccination by a method of the present invention is efficacious in protecting a subject against a formation of a flare, following exposure of the subject to HSV.

In one embodiment, the present invention provides a method of reducing the incidence of an HSV flare, comprising the step of contacting the subject with a mutant HSV strain, wherein the mutant strain contains an inactivating mutation in a Us8 gene encoding a gE protein. In another embodiment, the flare that is prevented follows exposure of the subject to HSV. In another embodiment, the subject has been infected with HSV before vaccination. In another embodiment, the subject is at risk for HSV infection. In another embodiment, whether or not the subject has been infected with HSV at the time of vaccination, vaccination by a method of the present invention is efficacious in reducing the incidence of a flare, following exposure of the subject to HSV.

In one embodiment, the present invention provides a method of inhibiting HSV recurrence in a subject, comprising the step of contacting the subject with a mutant HSV strain, wherein the mutant strain contains an inactivating mutation in a Us8 gene encoding a gE protein. In another embodiment, the recurrence that is prevented follows exposure of the subject to HSV. In another embodiment, the subject has been infected with HSV before vaccination. In another embodiment, the subject is at risk for HSV infection. In another embodiment, whether or not the subject has been infected with HSV at the time of vaccination, vaccination by a method of the present invention is efficacious in protecting a subject against a recurrence, following an exposure of the subject to an HSV.

In one embodiment, the present invention provides a method of reducing the incidence of HSV recurrence, comprising the step of contacting the subject with a mutant HSV strain, wherein the mutant strain contains an inactivating mutation in a Us8 gene encoding a gE protein. In another embodiment, the recurrence that is prevented follows exposure of the subject to HSV. In another embodiment, the subject has been infected with HSV before vaccination. In another embodiment, the subject is at risk for HSV infection. In another embodiment, whether or not the subject has been infected with HSV at the time of vaccination, vaccination by a method of the present invention is efficacious in reducing the incidence of a recurrence, following exposure of the subject to HSV.

In another embodiment, the present invention provides a method of suppressing HSV-1 infection in a subject, comprising the step of contacting the subject with a mutant HSV strain, wherein the mutant HSV strain contains an inactivating mutation in a Us8 gene encoding a gE protein. In another embodiment, the mutant HSV strain is a mutant HSV-1 strain. In another embodiment, the mutant HSV strain is a mutant HSV-2 strain.

In another embodiment, the present invention provides a method of suppressing HSV-2 infection in a subject, comprising the step of contacting the subject with a mutant HSV strain, wherein the mutant HSV strain contains an inactivating mutation in a Us8 gene encoding a gE protein. In another embodiment, the mutant HSV strain is a mutant HSV-1 strain. In another embodiment, the mutant HSV strain is a mutant HSV-2 strain.

According to any of the methods of the present invention and in one embodiment, the subject is human. In another embodiment, the subject is murine, which in one embodiment is a mouse, and, in another embodiment is a rat. In another embodiment, the subject is canine, feline, bovine, or porcine. In another embodiment, the subject is mammalian. In another embodiment, the subject is any organism susceptible to infection by HSV.

In another embodiment, the present invention provides a method of protecting a subject against formation of a zosteriform lesion or an analogous outbreak in a human subject, comprising the step of contacting the subject with a mutant HSV strain, wherein the mutant strain contains an inactivating mutation in a Us8 gene encoding a gE protein.

In another embodiment, the present invention provides a method of impeding formation of an HSV zosteriform lesion or an analogous outbreak in a human subject, comprising the step of contacting the subject with a mutant HSV strain, wherein the mutant strain contains an inactivating mutation in a Us8 gene encoding a gE protein.

In another embodiment, the zosteriform lesion or analogous outbreak that is impeded follows exposure of the subject to HSV. In another embodiment, the subject has been infected with HSV before vaccination. In another embodiment, the subject is at risk for HSV infection. In another embodiment, whether or not the subject has been infected with HSV at the time of vaccination, vaccination by a method of the present invention is efficacious in impeding formation of a zosteriform lesion or analogous outbreak, following an exposure of the subject to an HSV.

In another embodiment, the present invention provides a method of impeding HSV zosteriform spread or an analogous condition in a human subject, comprising the step of contacting the subject with a mutant HSV strain, wherein the mutant strain contains an inactivating mutation in a Us8 gene encoding a gE protein. In another embodiment, the zosteriform spread or analogous condition that is impeded follows exposure of the subject to HSV. In another embodiment, the subject has been infected with HSV before vaccination. In another embodiment, the subject is at risk for HSV infection. In another embodiment, whether or not the subject has been infected with HSV at the time of vaccination, vaccination by a method of the present invention is efficacious in impeding formation of a zosteriform spread or analogous condition, following exposure of the subject to HSV.

"Zosteriform" refers, in one embodiment, to skin lesions characteristic of an HSV infection, particularly during reactivation infection, which, in one embodiment, begin as a rash and follow a distribution near dermatomes, commonly occurring in a strip or belt-like pattern. In one embodiment, the rash evolves into vesicles or small blisters filled with serous fluid. In one embodiment, zosteriform lesions form in mice as a result of contact with HSV. In another embodiment, zosteriform lesions form in humans as a result of contact with HSV.

"Zosteriform spread" refers, in one embodiment, to an HSV infection that spreads from the ganglia to secondary skin sites within the dermatome. In another embodiment, the term refers to spread within the same dermatome as the initial site of infection. In another embodiment, the term refers to any other definition of "zosteriform spread" known in the art. "Outbreak", in another embodiment, refers to a sudden increase in symptoms of a disease or in the spread or prevalence of a disease, and in one embodiment, refers to a sudden increase in zosteriform lesions, while in another embodiment, "outbreak" refers to a sudden eruption of zosteriform lesions.

In one embodiment, the present invention provides a method of impeding the formation of a dermatome lesion or an analogous condition in a human subject, comprising the step of contacting the subject with a mutant HSV strain, wherein the mutant strain contains an inactivating mutation in a Us8 gene encoding a gE protein. In another embodiment, the dermatome lesion or analogous condition that is impeded follows exposure of the subject to HSV. In one embodiment, dermatome lesions form in humans as a result of contact with HSV. In another embodiment, dermatome lesions in humans most often develop when the virus reactivates from latency in the ganglia and in one embodiment, spreads down nerves, in one embodiment, causing a recurrent infection. In another embodiment, dermatome lesions form in mice as a result of contact with HSV. In another embodiment, the subject has been infected with HSV before vaccination. In another embodiment, the subject is at risk for HSV infection. In another embodiment, whether or not the subject has been infected with HSV at the time of vaccination, vaccination by a method of the present invention is efficacious in impeding the formation of a dermatome lesion or analogous condition, following exposure of the subject to HSV.

As provided herein, vaccination with gE-null HSV strains of the present invention protects against latent HSV infection (Example 5) and formation of zosteriform and dermatome lesions (Example 4) after subsequent infection with virulent HSV. In another embodiment, the vaccination protects against disease caused by or associated with latent HSV infection. In another embodiment, the vaccination does not itself cause significant disease (Example 2).

"Virulent HSV" refers, in one embodiment, to a naturally occurring HSV strain. In another embodiment, the term refers to an HSV strain capable of causing infection. In another embodiment, the term refers to an HSV strain capable of establishing latent infection.

In another embodiment, the present invention provides a method of impeding neuronal spread of an HSV in a subject, comprising the step of contacting the subject with a mutant HSV strain, wherein the mutant strain contains an inactivating mutation in a Us8 gene encoding a gE protein. In another embodiment, the neuronal spread that is impeded follows exposure of the subject to HSV. In another embodiment, the subject has been infected with HSV before vaccination. In another embodiment, the subject is at risk for HSV infection. In another embodiment, whether or not the subject has been infected with HSV at the time of vaccination, vaccination by a method of the present invention is efficacious in impeding neuronal viral spread, following an exposure of the subject to HSV.

Methods of measuring neuronal HSV spread are well known in the art, and include, in one embodiment, determination of the presence and extent of secondary dermatome lesion (Example 2). Other embodiments of methods for measuring viral spread are described, for example, in Labetoulle M et al. (Neuronal propagation of HSV1 from the oral mucosa to the eye. Invest Ophthalmol Vis Sci. 2000 August; 41(9):2600-6) and Thompson K A et al. (Herpes simplex replication and dissemination is not increased by corticosteroid treatment in a rat model of focal Herpes encephalitis. J. Neurovirol. 2000 February; 6(1):25-32).

In one embodiment, the present invention provides a method of reducing the incidence of herpetic ocular disease in a subject, comprising the step of contacting the subject with a mutant strain of HSV, wherein the mutant strain contains an inactivating mutation in a Us8 gene encoding a gE protein. In another embodiment, the subject is infected by HSV. In another embodiment, the subject is at risk of infection by the HSV.

In one embodiment, the present invention provides a method of reducing the severity of herpetic ocular disease in a subject, comprising the step of contacting the subject with a mutant strain of HSV, wherein the mutant strain contains an inactivating mutation in a Us8 gene encoding a gE protein. In another embodiment, the subject is infected by HSV. In another embodiment, the subject is at risk of infection by HSV. In another embodiment, the vaccine strain is from a different species from the challenge strain. In another embodiment, the vaccine strain is of the same species as the challenge strain.

In another embodiment, the present invention provides a method of reducing the incidence of an HSV-1 corneal infection, herpes keratitis or any other herpetic ocular disease in a subject, the method comprising the step of administering to said subject a mutant strain of HSV of the present invention, thereby reducing an incidence of an HSV-1 corneal infection or herpes keratitis in a subject. In another embodiment, administering to said subject a mutant strain of HSV of the present invention elicits an immune response against the HSV-1.

Methods for determining the presence and extent of herpetic ocular disease, corneal infection, and herpes keratitis are well known in the art, and are described, for example, in Labetoulle M et al. (Neuronal propagation of HSV1 from the oral mucosa to the eye. Invest Ophthalmol V is Sci. 2000 August; 41(9):2600-6) and Majumdar S i (Dipeptide monoester ganciclovir prodrugs for treating HSV-1-induced corneal epithelial and stromal keratitis: in vitro and in vivo evaluations. J Ocul Pharmacol Ther. 2005 December; 21(6): 463-74).

In one embodiment, the present invention provides a method of reducing the incidence of a genital ulcer disease in a subject, comprising the step of contacting the subject with a mutant strain of HSV, wherein the mutant strain contains an inactivating mutation in a Us8 gene encoding a gE protein. In another embodiment, the subject is infected by HSV. In another embodiment, the subject is at risk of infection by HSV In one embodiment, the present invention provides a method of reducing the severity of genital ulcer disease in a subject, comprising the step of contacting the subject with a mutant strain of HSV, wherein the mutant strain contains an inactivating mutation in a Us8 gene encoding a gE protein. In another embodiment, the subject is infected by HSV. In another embodiment, the subject is at risk of infection by HSV.

In one embodiment, genital ulcer disease is characterized by ulcerative lesions on the genitals. Methods for determining the presence and extent of genital ulcer disease are well known in the art.

In one embodiment, the present invention provides a method of reducing the incidence of HSV-1-mediated encephalitis in a subject, comprising the step of contacting the subject with a mutant strain of HSV, wherein the mutant strain contains an inactivating mutation in a Us8 gene encoding a gE protein. "HSV-1 encephalitis" refers, in one embodiment, to encephalitis caused by HSV-1. In another embodiment, the term refers to encephalitis associated with HSV-1. In another embodiment, the term refers to any other type of HSV-1-mediated encephalitis known in the art. In another embodiment, the subject is infected by HSV. In another embodiment, the subject is at risk of infection by HSV. In another embodiment, the vaccine strain is from a different species from the challenge strain. In another embodiment, the vaccine strain is of the same species as the challenge strain.

"HSV-1" refers, in one embodiment, to a Herpes Simplex Virus 1. In another embodiment, the term refers to a KOS strain. In another embodiment, the term refers to an F strain. In another embodiment, the term refers to an NS strain. In another embodiment, the term refers to a CL101 strain. In another embodiment, the term refers to a "17" strain. In another embodiment, the term refers to a "17+syn" strain. In another embodiment, the term refers to a MacIntyre strain. In another embodiment, the term refers to an MP strain. In another embodiment, the term refers to an HF strain. In another embodiment, the term refers to any other HSV-1 strain known in the art.

"HSV-2" refers, in one embodiment to a Herpes Simplex Virus 2. In another embodiment, the term refers to an HSV-2 333 strain. In another embodiment, the term refers to a 2.12 strain. In another embodiment, the term refers to an HG52 strain. In another embodiment, the term refers to an MS strain. In another embodiment, the term refers to an 186 strain. In another embodiment, the term refers to a G strain. In another embodiment, the term refers to any other HSV-2 strain known in the art.

In another embodiment, the present invention provides a method of reducing the incidence of HSV-2-mediated encephalitis in a subject, comprising the step of contacting the subject with a mutant strain of HSV, wherein the mutant strain contains an inactivating mutation in a Us8 gene encoding a gE protein. "HSV-2 encephalitis" refers, in one embodiment, to encephalitis caused by HSV-2. In another embodiment, the term refers to encephalitis associated with HSV-2. In another embodiment, the term refers to any other type of HSV-2-mediated encephalitis known in the art. In another embodiment, the subject is infected by HSV. In another embodiment, the subject is at risk of infection by HSV In one embodiment, the present invention provides a method of reducing the severity of herpes-mediated encephalitis in a subject, comprising the step of contacting the subject with a mutant strain of HSV, wherein the mutant strain contains an inactivating mutation in a Us8 gene encoding a gE protein. In one embodiment, the subject is infected by HSV. In another embodiment, the subject is at risk of infection by HSV.

In one embodiment, the herpes-mediated encephalitis treated or prevented by a method of the present invention is a focal herpes encephalitis. In another embodiment, the herpes-mediated encephalitis is a neonatal herpes encephalitis. In another embodiment, the herpes-mediated encephalitis is any other type of herpes-mediated encephalitis known in the art.

In one embodiment, the present invention provides a method of reducing the incidence of disseminated HSV infection in a subject, comprising the step of contacting the subject with a mutant strain of HSV, wherein the mutant strain contains an inactivating mutation in a Us8 gene encoding a gE protein. In another embodiment, the subject is infected by HSV. In another embodiment, the subject is at risk of infection by the HSV.

In one embodiment, the present invention provides a method of reducing the severity of disseminated HSV infection in a subject, comprising the step of contacting the subject with a mutant strain of HSV, wherein the mutant strain contains an inactivating mutation in a Us8 gene encoding a gE protein. In another embodiment, the subject is infected by HSV. In another embodiment, the subject is at risk of infection by HSV.

In one embodiment, the present invention provides a method of reducing the incidence of a neonatal HSV-1 infection in an offspring of a subject, comprising the step of contacting the subject with a mutant HSV strain, wherein the mutant HSV strain contains an inactivating mutation in a Us8 gene encoding a gE protein. In one embodiment, the offspring is contacted the subject with the mutant HSV strain. In another embodiment, the subject is infected by HSV. In another embodiment, the subject is at risk of infection by HSV.

In one embodiment, the present invention provides a method of reducing the incidence of a neonatal HSV-2 infection in an offspring of a subject, comprising the step of contacting the subject with a mutant HSV strain, wherein the mutant HSV strain contains an inactivating mutation in a Us8 gene encoding a gE protein. In one embodiment, the subject is infected by HSV. In another embodiment, the subject is at risk of infection by HSV.

In one embodiment, the present invention provides a method of reducing the transmission of an HSV-1 infection from a subject to an offspring thereof, the method comprising the step of contacting the subject with a mutant HSV strain, wherein the mutant HSV strain contains an inactivating mutation in a Us8 gene encoding a gE protein.

In one embodiment, the present invention provides a method of reducing the transmission of an HSV-2 infection from a subject to an offspring thereof, the method comprising the step of contacting the subject with a mutant HSV strain, wherein the mutant HSV strain contains an inactivating mutation in a Us8 gene encoding a gE protein.

In one embodiment, the present invention provides a method of reducing HIV-1 transmission to an offspring, the method comprising the step of contacting the subject with a mutant HSV strain, wherein the mutant HSV strain contains an inactivating mutation in a Us8 gene encoding a gE protein. As is known in the art, HSV-2 infection increases HIV-1 viral shedding in genital secretions (Nagot N et al. Reduction of HIV-1 RNA levels with therapy to suppress herpes simplex virus. N Engl J Med. 2007 Feb. 22; 356(8):790-9). Thus, methods of the present invention of inhibiting HSV-2 infection are also believed to be efficacious for reducing HIV-1 transmission to an offspring. In another embodiment, the mutant HSV strain is an HSV-1 strain. In another embodiment, the mutant HSV strain is an HSV-2 strain.

In one embodiment, the present invention provides a method of reducing HIV-1 transmission to a sexual partner, the method comprising the step of contacting the subject with a mutant HSV strain, wherein the mutant HSV strain contains an inactivating mutation in a Us8 gene encoding a gE protein. As is known in the art, HSV-2 infection increases HIV-1 viral shedding in genital secretions. Thus, methods of the present invention of inhibiting HSV-2 infection are also believed to be efficacious for reducing HIV-1 transmission to a sexual partner. In another embodiment, the mutant HSV strain is an HSV-1 strain. In another embodiment, the mutant HSV strain is an HSV-2 strain.

In one embodiment, the present invention provides a method of reducing susceptibility to HIV-1, the method comprising the step of contacting the subject with a mutant HSV strain, wherein the mutant HSV strain contains an inactivating mutation in a Us8 gene encoding a gE protein. As is known in the art, HSV-2 infection increases HIV-1 replication (Ouedraogo A et al. Impact of suppressive herpes therapy on genital HIV-1 RNA among women taking anti retroviral therapy: a randomized controlled trial. AIDS. 2006 Nov. 28; 20(18):2305-13). Thus, methods of the present invention of inhibiting HSV-2 infection are also believed to be efficacious for reducing susceptibility to HIV-1. In another embodiment, the mutant HSV strain is an HSV-1 strain. In another embodiment, the mutant HSV strain is an HSV-2 strain.

In one embodiment, the present invention provides a method of reducing the severity of a neonatal HSV infection in an offspring of a subject, comprising the step of contacting the subject with a mutant strain of HSV, wherein the mutant strain contains an inactivating mutation in a Us8 gene encoding a gE protein. In another embodiment, the subject is infected by HSV. In another embodiment, the subject is at risk of infection by HSV.

In one embodiment, the present invention provides a method of reducing the incidence of a disease, disorder, or symptom associated with or secondary to a herpes-mediated encephalitis in a subject, comprising the step of contacting the subject with a mutant HSV strain, wherein the mutant strain contains an inactivating mutation in a Us8 gene encoding a gE protein.

In one embodiment, the present invention provides a method of treating a disease, disorder, or symptom associated with or secondary to a herpes-mediated encephalitis in a subject, comprising the step of contacting the subject with a mutant HSV strain, wherein the mutant strain contains an inactivating mutation in a Us8 gene encoding a gE protein, thereby treating a disease, disorder, or symptom associated with or secondary to a herpes-mediated encephalitis in a subject.

In one embodiment, the disease, disorder, or symptom is fever. In another embodiment, the disease, disorder, or symptom is headache. In another embodiment, the disease, disorder, or symptom is stiff neck. In another embodiment, the disease, disorder, or symptom is seizures. In another embodiment, the disease, disorder, or symptom is partial paralysis. In another embodiment, the disease, disorder, or symptom is stupor. In another embodiment, the disease, disorder, or symptom is coma. In another embodiment, the disease, disorder, or symptom is any other disease, disorder, or symptom known in the art that is associated with or secondary to herpes-mediated encephalitis.

Methods of determining the presence and severity of herpes-mediated encephalitis are well known in the art, and are described, for example, in Bonkowsky J L et al. (Herpes simplex virus central nervous system relapse during treatment of infantile spasms with corticotropin. Pediatrics. 2006 May; 117(5):e1045-8) and Khan O A et al. (Herpes encephalitis presenting as mild aphasia: case report. BMC Fam Pract. 2006 Mar. 24; 7:22).

In one embodiment, the present invention provides a method of treating a disease, disorder, or symptom associated with an HSV infection in a subject, comprising the step of contacting the subject with a mutant HSV strain, wherein the mutant strain contains an inactivating mutation in a Us8 gene encoding a gE protein.

In one embodiment, the present invention provides a method of reducing the incidence of a disease, disorder, or symptom associated with an HSV infection in a subject, comprising the step of contacting the subject with a mutant HSV strain, wherein the mutant strain contains an inactivating mutation in a Us8 gene encoding a gE protein.

In one embodiment, the present invention provides a method of treating a disease, disorder, or symptom secondary to an HSV infection in a subject, comprising the step of contacting the subject with a mutant HSV strain, wherein the mutant strain contains an inactivating mutation in a Us8 gene encoding a gE protein.

In one embodiment, the present invention provides a method of reducing the incidence of a disease, disorder, or symptom secondary to an HSV infection in a subject, comprising the step of contacting the subject with a mutant HSV strain, wherein the mutant strain contains an inactivating mutation in a Us8 gene encoding a gE protein.

In one embodiment, the disease, disorder, or symptom secondary to an HSV infection is oral lesions. In another embodiment, the disease, disorder, or symptom is genital lesions. In another embodiment, the disease, disorder, or symptom is oral ulcers. In another embodiment, the disease, disorder, or symptom is genital ulcers. In another embodiment, the disease, disorder, or symptom is fever. In another embodiment, the disease, disorder, or symptom is headache. In another embodiment, the disease, disorder, or symptom is muscle ache. In another embodiment, the disease, disorder, or symptom is swollen glands in the groin area. In another embodiment, the disease, disorder, or symptom is painful urination. In another embodiment, the disease, disorder, or symptom is vaginal discharge. In another embodiment, the disease, disorder, or symptom is blistering. In another embodiment, the disease, disorder, or symptom is flu-like malaise. In another embodiment, the disease, disorder, or symptom is keratitis. In another embodiment, the disease, disorder, or symptom is herpetic whitlow. In another embodiment, the disease, disorder, or symptom is Bell's palsy. In another embodiment, the disease, disorder, or symptom is herpetic erythema multiforme. In another embodiment, the disease, disorder, or symptom is a lower back symptom (e.g. numbness, tingling of the buttocks or the area around the anus, urinary retention, constipation, and impotence). In another embodiment, the disease, disorder, or symptom is a localized eczema herpeticum. In another embodiment, the disease, disorder, or symptom is a disseminated eczema herpeticum. In another embodiment, the disease, disorder, or symptom is a herpes gladiatorum. In another embodiment, the disease, disorder, or symptom is a herpetic sycosis. In another embodiment, the disease, disorder, or symptom is an esophageal symptom (e.g. difficulty swallowing or burning, squeezing throat pain while swallowing, weight loss, pain in or behind the upper chest while swallowing). In another embodiment, the disease, disorder, or symptom is any other disease, disorder, or symptom is known in the art.

The HSV infection treated or ameliorated by methods and compositions of the present invention is, in one embodiment, a genital HSV infection. In another embodiment, the HSV infection is an oral HSV infection. In another embodiment, the HSV infection is an ocular HSV infection. In another embodiment, the HSV infection is a dermatologic HSV infection.

In one embodiment, the HSV infection is an HSV-2 infection. In another embodiment, the HSV is an HSV-1 infection. In another embodiment, the HSV infection is any other type of HSV infection known in the art.

In one embodiment, the present invention provides a method of inducing rapid clearance of an HSV-1 infection in a subject, comprising the step of contacting the subject with a mutant HSV strain, wherein the mutant strain contains an inactivating mutation in a Us8 gene encoding a gE protein. In another embodiment, the mutant HSV strain is a mutant HSV-1 strain. In another embodiment, the mutant HSV strain is a mutant HSV-2 strain.

In one embodiment, the present invention provides a method of inducing rapid clearance of an HSV-2 infection in a subject, comprising the step of contacting the subject with a mutant HSV strain, wherein the mutant strain contains an inactivating mutation in a Us8 gene encoding a gE protein. In another embodiment, the mutant HSV strain is a mutant HSV-1 strain. In another embodiment, the mutant HSV strain is a mutant HSV-2 strain.

In one embodiment, the present invention provides a method of inducing an anti-HSV immune response in a subject, comprising the step of contacting the subject with a mutant HSV strain, wherein the mutant strain contains an inactivating mutation in a Us8 gene encoding a gE protein, thereby inducing an anti-HSV immune response in a subject. In another embodiment, the mutant HSV strain is a mutant HSV-1 strain. In another embodiment, the mutant HSV strain is a mutant HSV-2 strain.

In one embodiment, the present invention provides a method of inducing an anti-HSV neutralizing antibody response in a subject, comprising the step of contacting the subject with a mutant HSV strain, wherein the mutant strain contains an inactivating mutation in a Us8 gene encoding a gE protein. In another embodiment, the mutant HSV strain is a mutant HSV-1 strain. In another embodiment, the mutant HSV strain is a mutant HSV-2 strain.

In one embodiment, the present invention provides a method of inhibiting HSV labialis in a subject, comprising the step of vaccinating the subject against an HSV by a method of the present invention.

In another embodiment, the present invention provides a method of inhibiting HSV labialis in a subject, comprising the step of impeding an HSV infection in the subject by a method of the present invention.

In one embodiment, the immune response induced by methods and compositions of the present invention is a cellular immune response. In another embodiment, the immune response comprises a CD8$^+$ cytotoxic T lymphocyte (CTL) response. In another embodiment, the immune response comprises a CD4$^+$ helper T cell response. In another embodiment, the immune response comprises a humoral immune response.

The route of administration of the mutant strains in the methods of the present invention is, in one embodiment, epidermal. In another embodiment, the mutant strain is administered by epidermal scarification or scratching. In another embodiment, the mutant strain is administered intramuscularly. In another embodiment, the mutant strain is administered subcutaneously. In another embodiment, the mutant strain is administered intranasally. In another embodiment, the mutant strain is administered transdermally. In another embodiment, the mutant strain is administered intravaginally. In another embodiment, the mutant strain is administered transmucosally, which in one embodiment, is intrarespiratory mucosally. In another embodiment, the mutant strain is administered intranasally. In another embodiment, the mutant strain is administered in an aerosol. In another embodiment, the mutant strain is administered via any other route known in the art.

In one embodiment, the inactivating mutation in the gE-encoding gene of HSV strains as described in the methods and compositions of the present invention is a deletion mutation. In another embodiment, the inactivating mutation is an insertion mutation. In another embodiment, the inactivating mutation is a substitution mutation. In another embodiment, the inactivating mutation is a gE-null mutation. In another embodiment, the inactivating mutation is any other type of mutation known in the art.

In one embodiment, the inactivating mutation in the glycoprotein-encoding gene of HSV strains as described in the methods and compositions of the present invention is a deletion mutation. In another embodiment, the inactivating mutation is an insertion mutation. In another embodiment, the inactivating mutation is a substitution mutation. In another embodiment, the inactivating mutation is a null mutation. In another embodiment, the inactivating mutation is any other type of mutation known in the art. In one embodiment, the insertion, deletion or substitution mutation comprises an insertion, deletion or substitution of a single amino acid, while in another embodiment, it comprises an insertion, deletion or substitution of 1-5 amino acids, 1-10 amino acids, 5-20 amino acids, 10-50 amino acids, 25-100 amino acids, 100-500 amino acids, 300-400 amino acids, 200-1000 amino acids, or 1000 or more amino acids.

In one embodiment, the present invention provides an isolated mutant HSV-1 strain comprising a first inactivating mutation in a gene encoding a gE protein and a second inactivating mutation. In another embodiment, the gene encoding a gE protein is a Us8 gene. In another embodiment, the mutation is a gE-null mutation. In one embodiment, an isolated mutant HSV-1 strain as described in the methods and compositions of the present invention further comprises one or more additional mutations, which in one embodiment are inactivating mutations. In another embodiment, the second or additional inactivating mutation is in a Us7 gene. In another embodiment, the second or additional inactivating mutation is in a Us9 gene. In another embodiment, the second inactivating mutation is in any gene which confers neurovirulence. In another embodiment, the second inactivating mutation is in any gene required for virus entry into a host cell. In another embodiment, the second inactivating mutation is in a host shut-off gene. In another embodiment, the second inactivating mutation is in the thymidine kinase gene. In another embodiment, the second inactivating mutation is in any other HSV-1 gene known in the art. In another embodiment, the isolated mutant HSV-1 strain contains inactivating mutations in a gene encoding a gE protein, a Us7 gene, and a Us9 gene. In another embodiment, an isolated mutant HSV-1 strain as described in the methods and compositions of the present invention further comprises an additional mutation in a gene encoding a gD protein.

In one embodiment, the present invention provides an isolated mutant HSV-2 strain comprising a first inactivating mutation in a gene encoding a gE protein and a second inactivating mutation. In another embodiment, the gene encoding a gE protein is a Us8 gene. In another embodiment, the mutation is a gE-null mutation. In one embodiment, an isolated mutant HSV-2 strain as described in the methods and compositions of the present invention further comprises one or more additional mutations, which in one embodiment are inactivating mutations. In another embodiment, the second or additional inactivating mutation is in a Us7 gene. In another embodiment, the second or additional inactivating mutation is in a Us9 gene. In another embodiment, the second inactivating mutation is in any gene which confers neurovirulence. In another embodiment, the second inactivating mutation is in any gene required for virus entry into a host cell. In another embodiment, the second inactivating mutation is in a host shut-off gene. In another embodiment, the second inactivating mutation is in the thymidine kinase gene. In another embodiment, the second inactivating mutation is in any other HSV-2 gene known in the art. In another embodiment, the isolated mutant HSV-2 strain contains inactivating mutations in a gene encoding a gE protein, a Us7 gene, and a Us9 gene. In another embodiment, an isolated mutant HSV-2 strain as described in the methods and compositions of the present invention further comprises an additional mutation in a gene encoding a gD protein.

In one embodiment, the Us7 gene that is mutated is highly conserved amongst alpha-herpesviruses. In another embodiment, the Us7 gene that is mutated is required for anterograde spread of the virus. In another embodiment, the Us7 gene that is mutated is required for retrograde spread of the virus.

In one embodiment, the Us9 gene that is mutated is highly conserved amongst alpha-herpesviruses. In another embodiment, the Us9 gene that is mutated is required for anterograde spread of the virus. In another embodiment, the Us9 gene that is mutated is required for retrograde spread of the virus.

In one embodiment, the mutation in Us7 and/or Us9 is an inactivating mutation. In another embodiment, the mutation is a deletion mutation. In another embodiment, the mutation is an insertion mutation. In another embodiment, the mutation is a substitution mutation. In another embodiment, the mutation is any other type of mutation known in the art.

In one embodiment, the additional gene that is mutated is highly conserved amongst alpha-herpesviruses. In another embodiment, the additional gene that is mutated is required for anterograde spread of the virus. In another embodiment, the additional gene that is mutated is required for retrograde spread of the virus.

In one embodiment, the additional gene that is mutated is a virion membrane protein. In one embodiment, the additional gene is a virion membrane protein not required, or non-essential, for virus entry. In another embodiment, the membrane protein is a glycoprotein. In another embodiment, the additional gene is glycoprotein J. In another embodiment, the additional gene is glycoprotein G. In another embodiment, the additional gene is glycoprotein K. In another embodiment, the additional gene is glycoprotein M. In another embodiment, the additional gene is selected from glycoproteins J, G, K, and M.

"Anterograde" refers, in one embodiment, to spread from ganglia to skin. In another embodiment, the term refers to spread from the cell body towards the axon. In another embodiment, the term refers to any other definition accepted in the art.

"Retrograde" refers, in one embodiment, to spread from the site of infection to ganglia. In another embodiment, the term refers to spread from the axon towards the cell body. In another embodiment, the term refers to any other definition accepted in the art.

In one embodiment, the additional mutation is introduced to enhance inhibition of anterograde spread of the mutant HSV-1 strain. In another embodiment, the additional mutation is required, in combination with a gE mutation, to confer inhibition of anterograde spread of the mutant HSV-1 strain. In another embodiment, the gE mutation is insufficient to confer inhibition of anterograde spread of the mutant HSV-1 strain. In another embodiment, the additional mutation is sufficient, in the absence of a gE mutation, to confer inhibition of anterograde spread of the mutant HSV-1 strain.

In one embodiment, the additional mutation is introduced to enhance inhibition of anterograde spread of the mutant HSV-2 strain. In another embodiment, the additional mutation is required, in combination with a gE mutation, to confer inhibition of anterograde spread of the mutant HSV-2 strain. In another embodiment, the gE mutation is insufficient to confer inhibition of anterograde spread of the mutant HSV-2 strain. In another embodiment, the additional mutation is sufficient, in the absence of a gE mutation, to confer inhibition of anterograde spread of the mutant HSV-2 strain.

In one embodiment, the additional mutation is introduced to enhance attenuation of virulence in the HSV-1 or HSV-2 strain or both. In another embodiment, the additional mutation is required, in combination with a gE mutation, to attenuate virulence.

In one embodiment, the additional gene that is mutated is a virion membrane protein. In another embodiment, the additional gene is a virion membrane protein required for virus entry. In another embodiment, the additional gene is glycoprotein B. In another embodiment, the additional gene is glycoprotein D. In another embodiment, the additional gene is glycoprotein H. In another embodiment, the additional gene is glycoprotein L.

In one embodiment, the mutant HSV strain as described in the methods and compositions of the present invention is replication-competent in skin tissue of the subject. In another embodiment, the mutant strain is replication-competent in skin cell of the subject. In another embodiment, the mutant strain is replication-competent in skin tissue of the species to which the subject belongs. In another embodiment, the mutant strain is replication-competent in a cell line derived from skin tissue of the subject's species. In another embodiment, the mutant strain is replication-competent in a culture of skin cells of the subject's species. In another embodiment, the mutant strain is replication-competent in a cell line derived from a skin cell of the subject's species.

"Replication competent" refers, in one embodiment, to an ability to replicate. In another embodiment, the term includes strains that exhibit impaired but still detectable levels of replication. In another embodiment, the term refers to a strain that exhibits measurable replication.

In one embodiment, the mutant HSV strain as described in the methods and compositions of the present invention is defective in its ability to spread from the site of inoculation to the dorsal root ganglia (DRG). In one embodiment, the dorsal root ganglia contain the neuron cell bodies of nerve fibres. In another embodiment, the mutant HSV strain is defective in retrograde spread. In another embodiment, the mutant HSV strain is impaired in retrograde spread. In another embodiment, the mutant HSV strain is significantly impaired in retrograde spread. In another embodiment, the mutant HSV strain is impaired in retrograde spread but is replication-competent in skin.

In one embodiment, the mutant HSV strain as described in the methods and compositions of the present invention is defective in spread from DRG to the skin. In another embodiment, the mutant HSV strain is defective in anterograde spread. In another embodiment, the mutant HSV strain is impaired in anterograde spread. In another embodiment, the mutant HSV strain is significantly impaired in anterograde spread. In another embodiment, the mutant HSV strain is impaired in anterograde spread but is replication-competent in skin.

"DRG" refers, in one embodiment, to a neuronal cell body. In another embodiment, the term refers to any other definition of "DRG" used in the art.

"Flare" or "recurrence" refers, in one embodiment, to reinfection of skin tissue following latent neuronal HSV infection. In another embodiment, the terms refer to reactivation of HSV after a latency period. In another embodiment, the terms refer to symptomatic HSV lesions following a non-symptomatic latency period.

In one embodiment, a mutant HSV strain of the present invention is replication-defective, either in a particular tissue or in general (e.g. in neural tissue). Methods for measuring viral replication are well known in the art and include, in one embodiment, titering assays of tissue samples near a site of inoculation (Examples herein). In another embodiment, recovery of infectious virus from tissues near a site of inoculation is utilized (Examples herein). Other embodiments as described in the methods for measuring viral replication are described, for example, in Thi T N et al. (Rapid determination of antiviral drug susceptibility of herpes simplex virus types 1 and 2 by real-time PCR. Antiviral Res. 2006 March; 69(3): 152-7); Schang L M et al. (Roscovitine, a specific inhibitor of cellular cyclin-dependent kinases, inhibits herpes simplex virus DNA synthesis in the presence of viral early proteins. J Virol. 2000 March, 74(5):2107-20); and Kennedy P G et al., (Replication of the herpes simplex virus type 1 RL1 mutant 1716 in primary neuronal cell cultures—possible relevance to use as a viral vector. J. Neurol Sci. 2000 Oct. 1; 179(S 1-2): 108-14).

In one embodiment, a mutant strain as described in the methods and compositions of the present invention is impaired in its spread in neural tissue of the subject. In another embodiment, the mutant strain is impaired in its spread in a culture of neural cells of the subject. In another embodiment, the mutant strain is impaired in its spread in neural tissue of the species to which the subject belongs. In another embodiment, the mutant strain is impaired in its spread in a cell line derived from neural tissue of the subject's species. In another embodiment, the mutant strain is impaired in its spread in a culture of neural cells of the subject's species. In another embodiment, the mutant strain is impaired in its spread in a cell line derived from a neural cell of the subject's species.

In one embodiment, a mutant strain as described in the methods and compositions of the present invention is impaired in its ability to enter neural tissue of the subject. In another embodiment, the mutant strain is impaired in its ability to enter a culture of neural cells of the subject. In another embodiment, the mutant strain is impaired in its ability to enter neural tissue of the species to which the subject belongs. In another embodiment, the mutant strain is impaired in its ability to enter a cell line derived from neural tissue of the subject's species. In another embodiment, the mutant strain is impaired in its ability to enter a culture of neural cells of the subject's species. In another embodiment, the mutant strain is impaired in its ability to enter a cell line derived from a neural cell of the subject's species.

In one embodiment, the mutant HSV strain as described in the methods and compositions of the present invention induces an anti-HSV immune response. In another embodiment, the immune response impedes replication of the HSV in the subject. In another embodiment, the immune response impedes neuronal spread of the HSV in the subject. In another embodiment, the immune response results in killing of HSV-infected cells in the subject.

In one embodiment, the mutant HSV strain as described in the methods and compositions of the present invention is a mutant HSV-1 strain. In another embodiment, the mutant HSV-1 strain confers protection against an HSV-1 infection, spread, or a consequence thereof (e.g. zosteriform lesions or herpetic ocular disease). In another embodiment, the mutant HSV strain is a mutant HSV-2 strain. In another embodiment, the mutant HSV-2 strain confers protection against an HSV-2 infection, spread, or a consequence thereof (e.g. zosteriform lesions or herpetic ocular disease). In another embodiment, the mutant HSV strain is any other mutant HSV strain known in the art.

In one embodiment, a mutant HSV-1 strain of the present invention protects a subject against infection and disorders and symptoms associated with infection with wild-type HSV-1. In another embodiment, the disorders and symptoms include herpes labialis (cold sores or fever blisters). In another embodiment, the disorders and symptoms include HSV-mediated cornea disease. In another embodiment, the disorders and symptoms include herpes-mediated retinitis. In another embodiment, the disorders and symptoms include herpes-mediated encephalitis. In another embodiment, the disorders and symptoms include HSV-1-mediated genital ulcer disease. In another embodiment, a mutant HSV-1 strain of the present invention provides substantial protection against HSV-1 infection and partial protection against one or more symptoms associated with HSV-2 infection. In another embodiment, these HSV-2 symptoms include the symptoms described hereinabove.

In another embodiment, the disorders and symptoms include HSV infections in an immunocompromised subject, including subjects with HIV. In another embodiment, a mutant HSV-1 strain of the present invention prevents or inhibits transmission of genital HSV-1 from a vaccinated mother to her newborn infant. In another embodiment, a mutant HSV strain of the present invention treats, suppresses, prevents or inhibits HSV in elderly subjects.

In one embodiment, a mutant HSV-2 strain of the present invention protects a subject against infection and disorders and symptoms associated with infection with wild-type HSV-2. In another embodiment, the mutant HSV-2 strain prevents or inhibits transmission of genital HSV-2 from the vaccinated mother to her newborn infant. In another embodiment, the mutant HSV-2 strain prevents or inhibits genital ulcer disease. In another embodiment, the mutant HSV-2 strain provides substantial protection against both HSV-2 and HSV-1 infection.

According to any of the methods of the invention, and in one embodiment, the infection is an HSV-1 infection. In another embodiment, the infection is an HSV-2 infection.

According to any of the methods of the invention, and in one embodiment, the vaccine strain is from a different species from the strain against which protection is conferred ("challenge strain"). In another embodiment, the vaccine strain is of the same species as the challenge strain.

In one embodiment, a vaccine as described in the methods and compositions of the present invention protects a subject against a challenge with heterologous HSV. In another embodiment, the heterologous challenge is a different strain of the same species. In another embodiment, in the case of a mutant HSV-1 vaccine strain, the vaccine confers protection against a heterologous HSV-1 strain. In another embodiment, in the case of a mutant HSV-2 vaccine strain, the vaccine confers protection against a heterologous HSV-2 strain. In another embodiment, the heterologous strain has an antigenic protein that is significantly heterologous relative to the vaccine strain. In another embodiment, the antigenic protein is gD. In another embodiment, the antigenic protein is gB. In another embodiment, the antigenic protein is any other antigenic protein known in the art.

In one embodiment, the heterologous strain has a gD protein that is significantly heterologous relative to the vaccine strain. In another embodiment, the gD protein of the heterologous strain shares 50% homology with the vaccine strain. In another embodiment, the homology shared between the gD protein of the heterologous strain and the vaccine strain is 55%. In another embodiment, the homology shared is 60%. In another embodiment, the homology shared is 65%. In another embodiment, the homology shared is 70%. In another embodiment, the homology shared is 75%. In another embodiment, the homology shared is 80%. In another embodiment, the homology shared is 85%. In another embodiment, the homology shared is 90%. In another embodiment, the homology shared is 95%. In another embodiment, the homology shared is 98%. In another embodiment, the homology shared is greater than 98%.

In one embodiment, the heterologous strain has a gB protein that is significantly heterologous relative to the vaccine strain. In another embodiment, the gB protein of the heterologous strain shares 50% homology with the vaccine strain. In another embodiment, the homology shared between the gB protein of the heterologous strain and the vaccine strain is 55%. In another embodiment, the homology shared is 60%. In another embodiment, the homology shared is 65%. In another embodiment, the homology shared is 70%. In another embodiment, the homology shared is 75%. In another embodiment, the homology shared is 80%. In another embodiment, the homology shared is 85%. In another embodiment, the homology shared is 90%. In another embodiment, the homology shared is 95%. In another embodiment, the homology shared is 98%. In another embodiment, the homology shared is greater than 98%.

In one embodiment, the heterologous challenge strain is HSV-1 NS. In another embodiment, the heterologous challenge strain is HSV-1(F). In another embodiment, the heterologous challenge strain is HSV-1(17). In another embodiment, the heterologous challenge strain is any other HSV-1 strain known in the art.

In one embodiment, the heterologous challenge strain is HSV-2(2.12). In another embodiment, the heterologous challenge strain is any other HSV-2 strain known in the art.

In one embodiment, the heterologous challenge strain is a different HSV species. In another embodiment, in the case of a mutant HSV-1 vaccine strain, the vaccine confers protection against HSV-2 challenge. In another embodiment, in the case of a mutant HSV-2 vaccine strain, the vaccine confers protection against HSV-1 challenge.

In one embodiment, a vaccine as described in the methods and compositions of the present invention protects a subject against a challenge with a large inoculum of HSV. In another embodiment, the large inoculum is $10^6$ plaque-forming units (pfu). In another embodiment, the inoculum is $1.5 \times 10^6$ pfu. In another embodiment, the inoculum is $2 \times 10^6$ pfu. In another embodiment, the inoculum is $3 \times 10^6$ pfu. In another embodiment, the inoculum is $4 \times 10^6$ pfu. In another embodiment, the inoculum is $5 \times 10^6$ pfu. In another embodiment, the inoculum is $7 \times 10^6$ pfu. In another embodiment, the inoculum is $1 \times 10^7$ pfu. In another embodiment, the inoculum is $1.5 \times 10^7$ pfu. In another embodiment, the inoculum is $2 \times 10^7$ pfu. In another embodiment, the inoculum is $3 \times 10^7$ pfu. In another embodiment, the inoculum is $4 \times 10^7$ pfu. In another embodiment, the inoculum is $5 \times 10^7$ pfu. In another embodiment, the inoculum is $7 \times 10^7$ pfu. In another embodiment, the inoculum is $10^8$ pfu. In another embodiment, the inoculum is $10^3$-$10^6$ pfu. In another embodiment, the inoculum is $10^3$-$10^5$ pfu. In another embodiment, the inoculum is $10^4$-$10^6$ pfu. In another embodiment, the inoculum is $3 \times 10^4$-$3 \times 10^6$ pfu. In another embodiment, the inoculum is $10^4$-$10^7$ pfu. In another embodiment, the inoculum is $3 \times 10^4$-$3 \times 10^7$ pfu. In another embodiment, the inoculum is $10^5$-$10^8$ pfu. In another embodiment, the inoculum is $3 \times 10^5$-$3 \times 10^8$ pfu. In another embodiment, the inoculum is more than $10^8$ pfu.

In one embodiment, a vaccine as described in the methods and compositions of the present invention exhibits enhanced safety relative to gE-containing HSV vaccine strains, due to its inability to infect the ganglia. In another embodiment, a method of the present invention exhibits enhanced safety relative to gE-containing HSV vaccine strains, due to its inability to spread in neurons.

Various embodiments of dosage ranges of mutant HSV particles can be used, in another embodiment, in methods of the present invention. In another embodiment, the dosage is $10^3$ pfu. In another embodiment, the dosage is $2 \times 10^3$ pfu. In another embodiment, the dosage is $3 \times 10^3$ pfu. In another embodiment, the dosage is $5 \times 10^3$ pfu. In another embodiment, the dosage is $10^4$ pfu. In another embodiment, the dosage is $1.5 \times 10^4$ pfu. In another embodiment, the dosage is $10^4$ pfu. In another embodiment, the dosage is $2 \times 10^4$ pfu. In another embodiment, the dosage is $3 \times 10^4$ pfu. In another embodiment, the dosage is $5 \times 10^4$ pfu. In another embodiment, the dosage is $7 \times 10^4$ pfu. In another embodiment, the dosage is $10^5$ pfu. In another embodiment, the dosage is $2 \times 10^5$ pfu. In another embodiment, the dosage is $3 \times 10^5$ pfu. In another embodiment, the dosage is $5 \times 10^5$ pfu. In another embodiment, the dosage is $7 \times 10^5$ pfu. In another embodiment, the dosage is $10^6$ pfu. In another embodiment, the dosage is $2 \times 10^6$ pfu. In another embodiment, the dosage is $3 \times 10^6$ pfu. In another embodiment, the dosage is $5 \times 10^6$ pfu. In another embodiment, the dosage is $7 \times 10^6$ pfu. In another embodiment, the dosage is $10^7$ pfu. In another embodiment, the dosage is $2 \times 10^7$ pfu. In another embodiment, the dosage is 3×10⁷ pfu. In another embodiment, the dosage is 5×10⁷ pfu. In another embodiment, the dosage is 7×10⁷ pfu. In another embodiment, the dosage is 10⁸ pfu. In another embodiment, the dosage is 2×10⁸ pfu. In another embodiment, the dosage is 3×10⁸ pfu. In another embodiment, the dosage is 5×10⁸ pfu. In another embodiment, the dosage is 7×10⁸ pfu.

In another embodiment, the dosage is 10³ pfu/dose. In another embodiment, the dosage is 2×10³ pfu/dose. In another embodiment, the dosage is 3×10³ pfu/dose. In another embodiment, the dosage is 5×10³ pfu/dose. In another embodiment, the dosage is 10⁴ pfu/dose. In another embodiment, the dosage is 1.5×10⁴ pfu/dose. In another embodiment, the dosage is 10⁴ pfu/dose. In another embodiment, the dosage is 2×10⁴ pfu/dose. In another embodiment, the dosage is 3×10⁴ pfu/dose. In another embodiment, the dosage is 5×10⁴ pfu/dose. In another embodiment, the dosage is 7×10⁴ pfu/dose. In another embodiment, the dosage is 10⁵ pfu/dose. In another embodiment, the dosage is 2×10⁵ pfu/dose. In another embodiment, the dosage is 3×10⁵ pfu/dose. In another embodiment, the dosage is 5×10⁵ pfu/dose. In another embodiment, the dosage is 7×10⁵ pfu/dose. In another embodiment, the dosage is 10⁶ pfu/dose. In another embodiment, the dosage is 2×10⁶ pfu/dose. In another embodiment, the dosage is 3×10⁶ pfu/dose. In another embodiment, the dosage is 5×10⁶ pfu/dose. In another embodiment, the dosage is 7×10⁶ pfu/dose. In another embodiment, the dosage is 10⁷ pfu/dose. In another embodiment, the dosage is 2×10⁷ pfu/dose. In another embodiment, the dosage is 3×10⁷ pfu/dose. In another embodiment, the dosage is 5×10⁷ pfu/dose. In another embodiment, the dosage is 7×10⁷ pfu/dose. In another embodiment, the dosage is 10⁸ pfu/dose. In another embodiment, the dosage is 2×10⁸ pfu/dose. In another embodiment, the dosage is 3×10⁸ pfu/dose. In another embodiment, the dosage is 5×10⁸ pfu/dose. In another embodiment, the dosage is 7×10⁸ pfu/dose. In another embodiment, the dose is more than 10⁸ pfu. In another embodiment, the dose is 10³-10⁶ pfu. In another embodiment, the dose is 10³-10⁵ pfu. In another embodiment, the dose is 10⁴-10⁶ pfu. In another embodiment, the dose is 3×10⁴-3×10⁶ pfu. In another embodiment, the dose is 10⁴-10⁷ pfu. In another embodiment, the dose is 3×10⁴-3×10⁷ pfu. In another embodiment, the dose is 10⁵-10⁸ pfu. In another embodiment, the dose is 3×10⁵-3×10⁸ pfu.

In one embodiment, "treating" refers to both therapeutic treatment and prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing, the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter aria to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, symptoms are primary, while in another embodiment, symptoms are secondary. In one embodiment, "primary" refers to a symptom that is a direct result of the subject viral infection, while in one embodiment, "secondary" refers to a symptom that is derived from or consequent to a primary cause. In one embodiment, the compositions and strains for use in the present invention treat primary or secondary symptoms or secondary complications related to HSV infection.

In another embodiment, "symptoms" may be any manifestation of a HSV infection, comprising blisters, ulcerations, or lesions on the urethra, cervix, upper thigh, and/or anus in women and on the penis, urethra, scrotum, upper thigh, and anus in men, inflammation, swelling, fever, flu-like symptoms, sore mouth, sore throat, pharyngitis, pain, blisters on tongue, mouth or lips, ulcers, cold sores, neck pain, enlarged lymph nodes, reddening, bleeding, itching, dysuria, headache, muscle pain, etc., or a combination thereof.

The gE protein as described in the methods and compositions of the present invention has, in one embodiment, the sequence:

```
                                               (SEQ ID No: 2)
MDRGAVVGFLLGVCVVSCLAGTPKTSWRRVSVGEDVSLLPAPGPTGRG

PTQKLLWAVEPLDGCGPLHPSWVSLMPPKQVPETVVDAACMRAPVPLA

MAYAPPAPSATGGLRTDFVWQERAAVVNRSLVIHGVRETDSGLYTLSV

GDIKDPARQVASVVLVVQPAPVPTPPPTPADYDEDDNDEGEDESLAGT

PASGTPRLPPPPAPPRSWPSAPEVSHVRGVTVRMETPEAILFSPGETF

STNVSIHAIAHDDQTYSMDVVWLRFDVPTSCAEMRIYESCLYHPQLPE

CLSPADAPCAASTWTSRLAVRSYAGCSRTNPPPRCSAEAHMEPVPGLA

WQAASVNLEFRDASPQHSGLYLCVVYVNDHIHAWGHITISTAAQYRNA

VVEQPLPQRGADLAEPTHPHVGAPPHAPPTHGALRLGAVMGAALLLSA

LGLSVWACMTCWRRRAWRAVKSRASGKGPTYIRVADSELYADWSSDSE

GERDQVPWLAPPERPDSPSTNGSGFEILSPTAPSVYPRSDGHQSRRQL

TTFGSGRPDRRYSQASDSSVFW.
```

In another embodiment, the gE protein is a homologue of SEQ ID No: 2. In another embodiment, the gE protein is a variant of SEQ ID No: 2. In another embodiment, the gE protein is an isomer of SEQ ID No: 2. In another embodiment, the gE protein is a fragment of SEQ ID No: 2. In another embodiment, the gE protein comprises SEQ ID No: 2.

In another embodiment, the gE protein is encoded by a nucleotide sequence having the sequence:

```
                                               (SEQ ID No: 3)
atggatcgcggggcggtggtggggtttcttctcggtgtttgtgttgta tcgtgcttggcgggaacgcccaaaacgtcctggagacgggtgagtgtc ggcgaggacgtttcgttgcttccagctccggggcctacggggcgcggc ccgacccagaaactactatgggccgtggaaccctggatgggtgcggc cccttacaccgtcgtgggtctcgctgatgcccccaagcaggtgccc gagacggtcgtggatgcggcgtgcatgcgcgctccggtcccgctggcg atgcgtacgccccccggccccatctgcgaccgggggtctacgaacg gacttcgtgtggcaggagcgcgcggccgtggttaaccggagtctggtt
```

-continued

```
attcacggggtccgagagacggacagcggcctgtataccctgtccgtg ggcgacataaaggacccggctcgccaagtggcctcggtggtcctggtg gtgcaaccggcccagttccgaccccaccccgacccagccgattac gacgaggatgacaatgacgagggcgaggacgaaagtctcgccggcact cccgccagcgggacccccggctcccgcctccccgccccccgagg tcttggcccagcgccccgaagtctcacatgtgcgtggggtgaccgtg cgtatggagactccggaagctatcctgttttccccggggagacgttc agcacgaacgtctccatccatgccatcgcccacgacgaccagacctac tccatggacgtcgtctggttgaggttcgacgtgccgacctcgtgtgcc gagatgcgaatatacgaatcgtgtctgtatcacccgcagctcccagaa tgtctgtccccggccgacgcgcgtgcgccgcgagtacgtggacgtct cgcctggccgtccgcagctacgcggggtgttccagaacaaaccccca ccgcgctgttcggccgaggacacatggagcccgtcccggggctggcgt ggcaggcggcctccgtcaatctggagttccgggacgcgtcccacaac actccggcctgtatctgtgtgtggtgtacgtcaacgaccatattcacg cctggggccacattaccatcagcaccgcggcgcagtaccggaacgcgg tggtggaacagcccctcccacagcgcggcgcggatttggccgagccca cccaccgcacgtcggggcccctccccacgcgcccccaacccacggcg ccctgcggttaggggcggtgatgggggccgccctgctgctgtctgcac tggggttgtcggtgtgggcgtgtatgacctgttggcgcaggcgtgccc ggcgggcggttaaaagcagggcctcgggtaaggggcccacgtacattc gcgtggccgacagcgagctgtacgcggactggagctcggacagcgagg gagaacgcgaccaggtcccgtggctggccccccggagagacccgact ctccctccaccaatggatccggctttgagatcttatccaacggctc cgtctgtataccccgtagcgatgggcatcaatctcgccgccagctca caaccttggatccggaaggcccgatcgccgttactcccaggcctccg attcgtccgtcttctggtaa.
```

In another embodiment, the gE protein is encoded by a nucleotide molecule that a homologue of SEQ ID No: 3. In another embodiment, the nucleotide molecule is a variant of SEQ ID No: 3. In another embodiment, the nucleotide molecule is an isomer of SEQ ID No: 3. In another embodiment, the nucleotide molecule is a fragment of SEQ ID No: 3. In another embodiment, the nucleotide molecule comprises SEQ ID No: 3.

In another embodiment, the gE protein as described in the methods and compositions of the present invention has the sequence:

```
                                           (SEQ ID No: 4)
MDRGAVVGFLLGVCVVSCLAGTPKTSWRRVSVGEDVSLLPAPGPTGRG

PTQKLLWAVEPLDGCGPLHPSWVSLMPPKQVPETVVDAACMRAPVPLA

MAYAPPAPSATGGLRTDFVWQERAAVVNRSLVIYGVRETDSGLYTLSV

GDIKDPARQVASVVLVVQPAPVPTPPPTPADYDEDDNDEGEGEDESLA

GTPASGTPRLPPSPAPPRSWPSAPEVSHVRGVTVRMETPEAILFSPGE

AFSTNVSIHAIAHDDQTYTMDVVWLRFDVPTSCAEMRIYESCLYHPQL

PECLSPADAPCAASTWTSRLAVRSYAGCSRTNPPPRCSAEAHMEPFPG

LAWQAASVNLEFRDASPQHSGLYLCVVYVNDHIHAWGHITINTAAQYR

NAVVEQPLPQRGADLAEPTHPHVGAPPHAPPTHGALRLGAVMGAALLL

SALGLSVWACMTCWRRRAWRAVKSRASGKGPTYIRVADSELYADWSSD

SEGERDQVPWLAPPERPDSPSTNGSGFEILSPTAPSVYPRSDGHQSRR

QLTTFGSGRPDRRYSQASDSSVFW.
```

In another embodiment, the gE protein is a homologue of SEQ ID No: 4. In another embodiment, the gE protein is a variant of SEQ ID No: 4. In another embodiment, the gE protein is an isomer of SEQ ID No: 4. In another embodiment, the gE protein is a fragment of SEQ ID No: 4. In another embodiment, the gE protein comprises SEQ ID No: 4.

In another embodiment, the gE protein is encoded by a nucleotide sequence having the sequence:

```
                                           (SEQ ID No: 5)
atggatcgcggggcggtggtggggtttcttacggtgtttgtgttgtat cgtgcttggcgggaacgcccaaaacgtcctggagacgggtgagtgtcg gcgaggacgtttcgttgctaccagctccggggcctacggggcgcggcc cgacccagaaactactatgggccgtggaacccctggatgggtgcggcc ccttacacccgtcgtgggtctcgctgatgccccccaagcaggtacccg agacggtcgtggatgcggcgtgcatgcgcgctccggtcccgctggcga tggcatacgcccccccggcccatctgcgaccgggggtctacggacgg acttcgtgtggcaggagcgcgcggccgtggttaaccggagtctggtta tttacggggtccgagagacggacagcggcctgtataccctgtctgtgg gcgacataaaggacccggctcgccaagtggcctcggtggtcctggtgg tgcaaccggcccagttccgactccaccccgacccagccgattacg acgaggatgacaatgacgagggcgagggcgaggacgaaagtctagccg gcactcccgccagcgggaccccggctcccgccttccccgcccccc cgaggtcttggcccagcgccccgaagtctcacacgtgcgtggggtga ccgtgcgtatggagactccggaagctatcctgttttccccggggagg cgtttagcacgaacgtctccatccatgccatcgcccacgacgaccaga cctacaccatggacgtcgtctggttgaggttcgacgtgccgacctcgt gtgccgagatgcgaatatacgaatcgtgtctgtatcatccgcagctcc cagagtgtctgtccccggccgacgctccgtgcgccgcgagtacgtgga cgtctcgcctggccgtccgcagctacgcggggtgttccagaacaaacc ccccgccgcgctgttcggccgaggctcacatggagcccttcccggggc tggcgtggcaggcggcctcagtcaatctggagttccgggacgcgtccc cacaacactccgggctgtatctgtgcgtggtgtacgtcaacgaccata ttcacgcatggggccacattaccatcaacaccgcggcgcagtaccgga acgcggtggtggaacagcccctcccacagcgcggcgcggatttggccg agcccacccacccgcacgtcggggcccctccccacgcgcccccaaccc
```

-continued

```
acggcgccctgcggttaggggcggtgatgggggccgccctgctgctgt ctgcgctggggttgtcggtgtgggcgtgtatgacctgttggcgcaggc gtgcctggcgggcggttaaaagcagggcctcgggtaaggggcccacgt acattcgcgtggccgacagcgagctgtacgcggactggagctcggaca gcgagggagaacgcgaccaggtcccgtggctggcccccccggagagac ccgactctccctccaccaatggatccggctttgagatcttatcaccaa cggctccgtctgtataccccccgtagcgatgggcatcaatctcgccgcc agctcacaacctttggatccggaaggcccgatcgccgttactcccagg cctccgattcgtccgtcttctggtaa.
```

In another embodiment, the gE protein is encoded by a nucleotide molecule that a homologue of SEQ ID No: 5. In another embodiment, the nucleotide molecule is a variant of SEQ ID No: 5. In another embodiment, the nucleotide molecule is an isomer of SEQ ID No: 5. In another embodiment, the nucleotide molecule is a fragment of SEQ ID No: 5. In another embodiment, the nucleotide molecule comprises SEQ ID No: 5.

In another embodiment, the gE protein as described in the methods and compositions of the present invention has the sequence:

```
(SEQ ID No: 6; this protein was mutated in
Examples 1-5 herein)
MARGAGLVFFVGVWVVSCLAAAPRTSWKRVTSGEDVVLLPAPAERTRA

HKLLWAAEPLDACGPLRPSWVALWPPRRVLETVVDAACMRAPEPLAIA

YSPPFPAGDEGLYSELAWRDRVAVVNESLVIYGALETDSGLYTLSVVG

LSDEARQVASVVLVVEPAPVPTPTPDDYDEEDDAGVTNARRSAFPPQP

PPRRPPVAPPTHPRVIPEVSHVRGVTVHMETLEAILFAPGETFGTNVS

IHAIAHDDGPYAMDVVWMRFDVPSSCADMRIYEACLYHPQLPECLSPA

DAPCAVSSWAYRLAVRSYAGCSRTTPPPRCFAEARMEPVPGLAWLAST

VNLEFQHASPQHAGLYLCVVYVDDHIHAWGHMTISTAAQYRNAVVEQH

LPQRQPEPVEPTRPHVRAPHPAPSARGPLRLGAVLGAALLLAALGLSA

WACMTCWRRRSWRAVKSRASATGPTYIRVADSELYADWSSDSEGERDG

SLWQDPPERPDSPSTNGSGFEILSPTAPSVYPHSEGRKSRRPLTTFGS

GSPGRRHSQASYPSVLW.
```

In another embodiment, the gE protein is a homologue of SEQ ID No: 6. In another embodiment, the gE protein is a variant of SEQ ID No: 6. In another embodiment, the gE protein is an isomer of SEQ ID No: 6. In another embodiment, the gE protein is a fragment of SEQ ID No: 6. In another embodiment, the gE protein comprises SEQ ID No: 6.

In another embodiment, the gE protein is encoded by a nucleotide sequence having the sequence:

```
(SEQ ID No: 7
atggctcgcggggccgggttggtgtttttgttggagtttgggtcgta tcgtgcctggcggcagcacccagaacgtcctggaaacgggtaacctcg ggcgaggacgtggtgttgcttccggcgcccgcggaacgcacccgggcc cacaaactactgtgggccgcggaacccctggatgcctgcggtcccctg
```

-continued

```
cgcccgtcgtgggtggcgctgtggcccccccgacgggtgctcgagacg gtcgtggatgcggcgtgcatgcgcgccccggaaccgctcgccatagca tacagtcccccgttccccgcgggcgacgagggactgtattcggagttg gcgtggcgcgatcgcgtagccgtggtcaacgagagtctggtcatctac ggggccctggagacggacagcggtctgtacaccctgtccgtggtcggc ctaagcgacgaggcgcgccaagtggcgtcggtggttctggtcgtggag cccgcccctgtgccgaccccgacccccgacgactacgacgaagaagac gacgcgggcgtgacgaacgcacgccggtcagcgttcccccccaaccc ccccccgtcgtcccccgtcgcccccccgacgcaccctcgtgttatc cccgaggtgtcccacgtgcgcggggtaacggtccatatggagaccctg gaggccattctgtttgcccccggggagacgtttgggacgaacgtctcc atccacgccattgcccacgacgacggtccgtacgccatggacgtcgtc tggatgcggtttgacgtgccgtcctcgtgcgccgatatgcggatctac gaagcttgtctgtatcacccgcagcttccagagtgtctatctccggcc gacgcgccgtgcgccgtaagttcctgggcgtaccgcctggcggtccgc agctacgccggctgttccaggactacgcccccgccgcgatgttttgcc gaggctcgcatggaaccggtcccggggttggcgtggctggcctccacc gtcaatctggaattccagcacgcctcccccagcacgccggcctctac ctgtgcgtggtgtacgtggacgatcatatccacgcctggggccacatg accatcagcaccgcggcgcagtaccggaacgcggtggtggaacagcac ctcccccagcgccagcccgagcccgtcgagcccacccgcccgcacgtg agagccccccatcccgcgccctccgcgcgcggcccgctgcgcctcggg gcggtgctgggggcggccctgttgctggccgccctcgggctgtccgcg tgggcgtgcatgacctgctggcgcaggcgctcctggcgggcggttaaa agccgggcctcggcgacgggccccacttacattcgcgtggcggacagc gagctgtacgcggactggagttcggacagcgaggggggagcgcgacggg tccctgtggcaggaccctccggagagacccgactctccctccacaaat ggatccggctttgagatcttatcaccaacggctccgtctgtatacccc catagcgaggggcgtaaatctcgccgcccgctcaccacctttggttcg ggaagcccgggccgtcgtcactcccaggcctcctatccgtccgtcctc tggtaa;
``` this gene was mutated in Examples 1-5 herein. In another embodiment, the gE protein is encoded by a nucleotide molecule that a homologue of SEQ ID No: 7. In another embodiment, the nucleotide molecule is a variant of SEQ ID No: 7. In another embodiment, the nucleotide molecule is an isomer of SEQ ID No: 7. In another embodiment, the nucleotide molecule is a fragment of SEQ ID No: 7. In another embodiment, the nucleotide molecule comprises SEQ ID No: 7.

In one embodiment, the gE protein is encoded by one of the following GenBank Accession Numbers: DQ889502, NC_001806, NC_001798, Z86099, X14112, L00036, X02138, and X04798, and any of AJ626469-AJ626498. In another embodiment, the gE protein is homologous to a sequence disclosed in one of the above GenBank Accession Numbers. In another embodiment, the gE protein is a variant of a sequence disclosed in one of the above GenBank Accession Numbers. In another embodiment, the gE protein is a fragment of a sequence disclosed in one of the above GenBank Accession Numbers.

In one embodiment, a gE protein HSV-1 glycoprotein E (gE) is a virion surface protein which is necessary for spread in neurons, and in one embodiment, is necessary for spread along axons in either direction, both to ("retrograde"), and from ("anterograde"), the neuronal cell body. In another embodiment, gE also facilitates evasion of the host immune system by sequestering host antibodies against HSV-1, rendering them inactive. In one embodiment, a gE-deleted HSV-1 replicates in the skin, but cannot spread along neurons to establish latency or escape the host's antibody response. Thus, in one embodiment, infection with the live attenuated gE-deleted HSV-1 or HSV-2 will elicit a robust immune response in the skin and protect the host from future encounters with the wild-type virus.

In one embodiment, the gE protein is a HSV-1 gE protein. In another embodiment, the gE protein is a HSV-1 (NS) gE protein. In another embodiment, the gE protein is a HSV-1 (17) gE protein. In another embodiment, the gE protein is a HSV-1(F) gE protein. In another embodiment, the gE protein is a HSV-1(KOS) gE protein. In another embodiment, the gE protein is a HSV-1(CL101) gE protein. In another embodiment, the gE protein is a HSV-1(MacIntyre) gE protein. In another embodiment, the gE protein is a HSV-1(MP) gE protein. In another embodiment, the gE protein is a HSV-1 (17+syn) gE protein. In another embodiment, the gE protein is a HSV-1(HF) gE protein. In another embodiment, the gE protein is any other HSV-1 gE protein known in the art.

In one embodiment, the gE protein is a HSV-2 gE protein. In another embodiment, the gE protein is a HSV-2(HG52) gE protein. In another embodiment, the gE protein is a HSV-2 (2.12) gE protein. In another embodiment, the gE protein is a HSV-2(MS) gE protein. In another embodiment, the gE protein is a HSV-2(186) gE protein. In another embodiment, the gE protein is a HSV-2(G) gE protein. In another embodiment, the gE protein is any other HSV-2 gE protein known in the art.

In another embodiment, the gE protein is any other HSV-1 or HSV-2 gE protein which in one embodiment has greater than 80% homology, in another embodiment, greater than 85% homology, in another embodiment greater than 95% homology, and in another embodiment greater than 98% homology to one of the gE proteins or nucleic acid sequences listed hereinabove. In another embodiment, the gE protein has 98.6% homology to HSV(NS) or HSV(17), or both.

In one embodiment, the gE protein is any other gE protein known in the art. In another embodiment, the gE protein is encoded by any Us8 nucleotide known in the art. In one embodiment, the Us8 gene has a nucleic acid sequence that corresponds to that set forth in Genbank Accession Nos: GeneID:2703448 or GeneID:1487360, or encodes a protein sequence of glycoprotein E, which in one embodiment, corresponds to that set forth in Genbank Accession Nos: NP_044670.1 or NP_044538.1.

In one embodiment, the HSV strain of and for use in the methods of the present invention comprise an additional inactivating mutation, which in one embodiment, is an inactivation of the Us6 gene. In one embodiment, the Us6 gene has a nucleic acid sequence that corresponds to that set forth in Genbank Accession Nos: GeneID:2703444, GeneID: 1487358, NC_001806, NC_001798, EU029158, EF177451, EF177450, EF157322, EF157321, EF157320, EF157319, Z86099, AJ004801, X14112, AF147806, AY779754, AY779753, AY779752, AY779751, AY779750, AY517492, AY155225, AB016432, AF021342, U12183, U12182, U12181, U12180, or InterPro:IPR002896, or encodes a protein sequence of glycoprotein D, which in one embodiment, corresponds to that set forth in Genbank Accession Nos: NP_044668.1, NP_044536.1, CAA38245, AAB59754, AAA19629, AAA19631, AAA19630, AAK93950, ABS84899, ABM66848, ABM66847, AAW23134, AAW23133, AAW23132, AAW23131, AAW23130, AAS01730, ABM52981, ABM52980, ABM52979, ABM52978, AAN74642, AAO26211, AAL90884, AAL90883, AAK19597, AAA45785, BAA00020, AAB60555, AAB60554, AAB60553, AAB60552, AAA98962, AAA98963, AAA45842, AAA45786, VGBEDZ, CAB06713, CAA32283, AAB72102, or CAB06713.1.

In another embodiment, the gD protein is any other HSV-1 or HSV-2 gD protein which in one embodiment has greater than 80% homology, in another embodiment, greater than 85% homology, in another embodiment greater than 95% homology, and in another embodiment greater than 98% homology to one of the gD proteins or nucleic acid sequences listed hereinabove.

In one embodiment, the HSV strain of and for use in the methods of the present invention comprise an additional inactivating mutation, which in one embodiment, is an inactivation of the Us9 gene. In one embodiment, the Us9 gene has a nucleic acid sequence that corresponds to that set forth in Genbank Accession Nos: GeneID:2703452 or GeneID: 1487362, or encodes a protein sequence of Us9 membrane protein, which in one embodiment, corresponds to that set forth in Genbank Accession Nos: NP_044672.1 or NP_044540.1.

In one embodiment, the HSV strain of and for use in the methods of the present invention comprise an additional inactivating mutation, which in one embodiment, is an inactivation of the Us5 gene. In one embodiment, the Us5 gene has a nucleic acid sequence that corresponds to that set forth in Genbank Accession Nos: GeneID:2703406 or GeneID: 1487357, or encodes a protein sequence of glycoprotein J, which in one embodiment, corresponds to that set forth in Genbank Accession Nos: NP_044667.1 or NP_044535.1.

In one embodiment, the HSV strain of and for use in the methods of the present invention comprise an additional inactivating mutation, which in one embodiment, is an inactivation of the Us4 gene. In one embodiment, the Us4 gene has a nucleic acid sequence that corresponds to that set forth in Genbank Accession Nos: GeneID:2703404 or GeneID: 1487356, or encodes a protein sequence of glycoprotein G, which in one embodiment, corresponds to that set forth in Genbank Accession Nos: NP_044666.1 or NP_044534.1.

In one embodiment, the HSV strain of and for use in the methods of the present invention comprise an additional inactivating mutation, which in one embodiment, is an inactivation of the UL53 gene. In one embodiment, the UL53 gene has a nucleic acid sequence that corresponds to that set forth in Genbank Accession Nos: GeneID:2703425 or GeneID: 1487342, or encodes a protein sequence of glycoprotein K, which in one embodiment, corresponds to that set forth in Genbank Accession Nos: NP_044656.1 or NP_044524.1.

In one embodiment, the HSV strain of and for use in the methods of the present invention comprise an additional inactivating mutation, which in one embodiment, is an inactivation of the UL1 gene. In one embodiment, the UL10 gene has a nucleic acid sequence that corresponds to that set forth in Genbank Accession Nos: GeneID:2703379 or GeneID: 1487293, or encodes a protein sequence of glycoprotein M, which in one embodiment, corresponds to that set forth in Genbank Accession Nos: NP_044611.1 or NP_044479.1.

In one embodiment, the HSV strain of and for use in the methods of the present invention comprise an additional inactivating mutation, which in one embodiment, is an inactivation of the UL1 gene. In one embodiment, the UL1 gene has a nucleic acid sequence that corresponds to that set forth in Genbank Accession Nos: GeneID:2703393 or GeneID: 1487292, or encodes a protein sequence of glycoprotein L, which in one embodiment, corresponds to that set forth in Genbank Accession Nos: NP_044602.1 or NP_044470.1.

In one embodiment, the HSV strain of and for use in the methods of the present invention comprise an additional inactivating mutation, which in one embodiment, is an inactivation of the UL22 gene. In one embodiment, the UL22 gene has a nucleic acid sequence that corresponds to that set forth in Genbank Accession Nos: GeneID:2703373 or GeneID: 1487306, or encodes a protein sequence of glycoprotein H, which in one embodiment, corresponds to that set forth in Genbank Accession Nos: NP_044623.1 or NP_044491.1.

In one embodiment, the HSV strain of and for use in the methods of the present invention comprise an additional inactivating mutation, which in one embodiment, is an inactivation of the UL27 gene. In one embodiment, the UL27 gene has a nucleic acid sequence that corresponds to that set forth in Genbank Accession Nos: GeneID:2703455 or GeneID: 1487312, or encodes a protein sequence of glycoprotein B, which in one embodiment, corresponds to that set forth in Genbank Accession Nos: NP_044629.1 or NP_044497.1.

In one embodiment, the HSV strain of and for use in the methods of the present invention comprise an additional inactivating mutation, which in one embodiment, is an inactivation of the UL44 gene. In one embodiment, the UL44 gene has a nucleic acid sequence that corresponds to that set forth in Genbank Accession Nos: GeneID:2703410 or GeneID: 1487331, or encodes a protein sequence of glycoprotein C, which in one embodiment, corresponds to that set forth in Genbank Accession Nos: NP_044646.1 or NP_044514.1.

In one embodiment, the HSV strain of and for use in the methods of the present invention comprise an additional inactivating mutation, which in one embodiment, is an inactivation of the UL49a gene. In one embodiment, the UL49a gene has a nucleic acid sequence that corresponds to that set forth in Genbank Accession Nos: GeneID:2703419 or GeneID: 1487337, or encodes a protein sequence of glycoprotein N, which in one embodiment, corresponds to that set forth in Genbank Accession Nos: NP_044652.1 or NP_044520.1.

In another embodiment, the additional mutation is in an HSV-1 or HSV-2 glycoprotein that, in one embodiment, has greater than 80% homology, in another embodiment, greater than 85% homology, in another embodiment greater than 95% homology, and in another embodiment greater than 98% homology to one or more of the glycoproteins listed hereinabove.

In one embodiment, HSV strains of and for use in the instant invention may comprise an inactivating mutation in a gene encoding gD, which in one embodiment is Us6. In another embodiment, HSV strains of and for use in the instant invention may comprise an inactivating mutation in a gene encoding gE, which in one embodiment is Us8. In another embodiment, HSV strains of and for use in the instant invention may comprise an inactivating mutation in a gene encoding gE and in a gene encoding gD. In one embodiment, the Us6 mutation is introduced to attenuate an HSV strain comprising a Us8 mutation that is highly virulent. In one embodiment, the Us6 mutation reduces virus entry. Us6 mutations, as well as any of the mutations of the present invention may be in either HSV-1 or HSV-2 or both. In one embodiment, HSV-1 gD and HSV-2 gD have a large degree of homology. In one embodiment, the amino acid sequences of HSV-1 gD and HSV-2 gD have 81% homology, or in another embodiment, greater than 80% homology, or in another embodiment, greater than 85% homology, or in another embodiment, greater than 90% homology, or in another embodiment, greater than 95% homology. In one embodiment, the nucleic acid sequences of HSV-1 gD and HSV-2 gD have 85% homology, or in another embodiment, greater than 80% homology, or in another embodiment, greater than 85% homology, or in another embodiment, greater than 90% homology, or in another embodiment, greater than 95% homology.

In one embodiment, the gD protein derived of the methods and compositions of the present invention has the sequence:

```
                                          (SEQ ID No: 14)
MGGTAARLGAVILFVVIVGLHGVRGKYALADASLKMADPNRFRGKDLP

VLDQLTDPPGVRRVYHIQAGLPDPFQPPSLPITVYYAVLERACRSVLL

NAPSEAPQIVRGASEDVRKQPYNLTIAWFRMGGNCAIPITVMEYTECS

YNKSLGACPIRTQPRWNYYDSFSAVSEDNLGFLMHAPAFETAGTYLRL

VKINDWTEITQFILEHRAKGSCKYALPLRIPPSACLSPQAYQQGVTVD

SIGMLPRFIPENQRTVAVYSLKIAGWHGPKAPYTSTLLPPELSETPNA

TQPELAPEDPEDSALLEDPVGTVAPQIPPNWHIPSIQDAATPYHPPAT

PNNMGLIAGAVGGSLLAALVICGIVYWMHRRTRKAPKRIRLPHIREDD

QPSSHQPL.
```

In another embodiment, the gD protein is a homologue of SEQ ID No: 14. In another embodiment, the gD protein is a variant of SEQ ID No: 14. In another embodiment, the gD protein is an isomer of SEQ ID No: 14. In another embodiment, the gD protein is a fragment of SEQ ID No: 14. In another embodiment, the gD protein comprises SEQ ID No: 14. In one embodiment, the gD amino acid sequence is an HSV-1 amino acid sequence.

In another embodiment, the gD protein is encoded by a nucleotide sequence having the sequence:

```
                                          (SEQ ID No: 15)
gtggcccggcccccaacaaaaatcacggtagcccggccgtgtgacac tatcgtccataccgaccacaccgacgaaccctaaggggagggggcca ttttacgaggaggaggggtataacaaagtctgtctttaaaaagcaggg gttagggagttgttcggtcataagcttcagcgcgaacgaccaactacc ccgatcatcagttatccttaaggtctcttttgtgtggtgcgttccggt atggggggactgccgccaggttgggggccgtgattttgtttgtcgtc atagtgggcctccatggggtccgcggcaaatatgccttggcggatgcc tctctcaagatggccgaccccaatcgctttcgcggcaaagaccttccg gtcctggaccagagaccgaccaccgggggtccggcgcgtgtaccacat ccaggcgggcctaccggacccgttccagccccccagcctcccgatcac ggtttactacgccgtgttggagcgcgcctgccgcagcgtgctcctaaa cgcaccgtcggaggccccccagattgtccgcggggcctccgaagacgt ccggaaacaaccctacaacctgaccatcgcttggtttcggatgggagg caactgtgctatccccatcacggtcatggagtacaccgaatgctccta caacaagtctctgggggcctgtcccatccgaacgcagccccgctggaa
```

```
ctactatgacagcttcagcgccgtcagcgaggataacctggggttcct gatgcacgccccgcgtttgagaccgccggcacgtacctgcggctcgt gaagataaacgactggacggagattacacagtttatcctggagcaccg agccaagggctcctgtaagtacgccctcccgctgcgcatccccccgtc agcctgcctctcccccaggcctaccagcaggggtgacggtggacag catcgggatgctgccccgcttcatcccgagaaccagcgcaccgtcgc cgtatacagcttgaagatcgccgggtggcacgggcccaaggcccata cacgagcaccctgctgcccccggagctgtccgagaccccaacgccac gcagccagaactcgccccggaagaccccgaggattcggccctcttgga ggaccccgtggggacggtggcgccgcaaatcccaccaaactggcacat cccgtcgatccaggacgccgcgacgccttaccatccccggccacccc gaacaacatgggcctgatcgccggcgcggtgggcggcagtctcctggc agccctggtcatttgcggaattgtgtactggatgcaccgccgcactcg gaaagcccaaagcgcatacgcctcccccacatccgggaagacgacca gccgtcctcgcaccagcccttgttttactagataccccccttaatgg gtgcgggggggtcaggtctgcggggttgggatgggaccttaactccat ataaagcgagtctggaagggggaaaggcggacagtcgataagtcggt agcggggacgcgcacctgttccgcctgtcgcacccacagctttttcg cgaaccgtcccgttttcgggat.
```

In another embodiment, the gD protein is encoded by a nucleotide molecule that a homologue of SEQ ID No: 15. In another embodiment, the nucleotide molecule is a variant of SEQ ID No: 15. In another embodiment, the nucleotide molecule is an isomer of SEQ ID No: 15. In another embodiment, the nucleotide molecule is a fragment of SEQ ID No: 15. In another embodiment, the nucleotide molecule comprises SEQ ID No: 15. In one embodiment, the gD nucleotide sequence is an HSV-1 nucleotide sequence.

In one embodiment, the gD protein as described in the methods and compositions of the present invention has the sequence:

```
                                        (SEQ ID No: 16)
MGRLTSGVGTAALLVVAVGLRVVCAKYALADPSLKMADPNRFRGKNLP

VLDQLTDPPGVKRVYHIQPSLEDPFQPPSIPITVYYAVLERACRSVLL

HAPSEAPQIVRGASDEARKHTYNLTIAWYRMGDNCAIPITVMEYTECP

YNKSLGVCPIRTQPRWSYYDSFSAVSEDNLGFLMHAPAFETAGTYLRL

VKINDWTEITQFILEHRARASCKYALPLRIPPAACLTSKAYQQGVTVD

SIGMLPRFIPENQRTVALYSLKIAGWHGPKPPYTSTLLPPELSDTTNA

TQPELVPEDPEDSALLEDPAGTVSSQIPPNWHIPSIQDVAPHHAPAAP

SNPGLIIGALAGSTLAVLVIGGIAFWVRRRAQMAPKRLRLPHIRDDDA

PPSHQPLFY.
```

In another embodiment, the gD protein is a homologue of SEQ ID No: 16. In another embodiment, the gD protein is a variant of SEQ ID No: 16. In another embodiment, the gD protein is an isomer of SEQ ID No: 16. In another embodiment, the gD Protein is a fragment of SEQ ID No: 16. In another embodiment, the gD protein comprises SEQ ID No: 16. In one embodiment, the gD amino acid sequence is an HSV-2 amino acid sequence.

In another embodiment, the gD protein is encoded by a nucleotide sequence having the sequence:

```
                                           (SEQ ID No: 17)
atgggcgtt tgacctccgg cgtcgggacg gcggccctgc tagttgtcgc ggtgggactc cgcgtcgtct gcgccaaata cgccttagca gacccctcgc ttaagatggc cgatcccaat cgatttcgcg ggaagaacct tccggttttg gaccagctga ccgaccccc cggggtgaag cgtgtttacc acattcagcc gagcctggag gacccgttcc agccccccag catcccgatc actgtgtact acgcagtgct ggaacgtgcc tgccgcagcg tgctcctaca tgccccatcg gaggccccc agatcgtgcg cggggcttcg gacgaggccc gaaagcacac gtacaacctg accatcgcct ggtatcgcat gggagacaat tgcgctatcc ccatcacggt tatggaatac accgagtgcc cctacaacaa gtcgttgggg gtctgcccca tccgaacgca gccccgctgg agctactatg acagctttag cgccgtcagc gaggataacc tgggattcct gatgcacgcc cccgccttcg agaccgcggg tacgtacctg cggctagtga agataaacga ctggacggag atcacacaat ttatcctgga gcaccgggcc cgcgcctcct gcaagtacgc tctcccctg cgcatccccc cggcagcgtg cctcacctcg aaggcctacc aacagggcgt gacggtcgac agcatcggga tgctaccccg ctttatcccc gaaaaccagc gcaccgtcgc cctatacagc ttaaaaatcg ccgggtggca cggccccaag ccccgtaca ccagcaccct gctgccgccg gagctgtccg acaccaccaa cgccacgcaa cccgaactcg ttccggaaga ccccgaggac tcggccctct tagaggatcc cgccgggacg gtgtcttcgc agatcccccc aaactggcac atcccgtcga tccaggacgt cgcgccgcac cacgccccg ccgcccccag caacccgggc ctgatcatcg gcgcgctggc cggcagtacc ctggcggtgc tggtcatcgg cggtattgcg ttttgggtac gccgccgcgc tcagatggcc cccaagcgcc tacgtctccc ccacatccgg gatgacgacg cgcccccctc gcaccagcca ttgttttact ag.
```

In another embodiment, the gD protein is encoded by a nucleotide molecule that a homologue of SEQ ID No: 17. In another embodiment, the nucleotide molecule is a variant of SEQ ID No: 17. In another embodiment, the nucleotide molecule is an isomer of SEQ ID No: 17. In another embodiment, the nucleotide molecule is a fragment of SEQ ID No: 17. In another embodiment, the nucleotide molecule comprises SEQ ID No: 17. In one embodiment, the gD nucleic acid sequence is an HSV-2 nucleic acid sequence.

In one embodiment, an inactivating mutation in a gene encoding gD comprises a mutation in which an alanine at amino acid 3 of HSV-1 gD or HSV-2 gD is mutated to a cysteine (A3C). In another embodiment, an inactivating mutation in a gene encoding gD comprises a mutation in which an alanine at residue 3 of HSV-1 gD or HSV-2 gD is mutated to a cysteine (A3C), a tyrosine at residue 2 to alanine (Y2A), a leucine at residue 4 to alanine (L4A), or a combination thereof. In another embodiment, an inactivating mutation in a gene encoding gD comprises a deletion of the alanine at residue 3 of HSV-1 gD or HSV-2 gD, a deletion of the tyrosine at residue 2, a deletion of leucine at residue 4, or a combination thereof. In another embodiment, an inactivating mutation in a gene encoding gD comprises a mutation at amino acid positions 38, 222, 223, 215, or a combination thereof. In another embodiment, an inactivating mutation in a gene encoding gD comprises a Y38C mutation, while in another embodiment, it comprises a R222N, F223I, D215G mutation, or combination thereof.

In another embodiment, an inactivating mutation in a gene encoding gD comprises mutations in amino acids 2 and 3, 3 and 4, 2-4, 1-5, 1-7, or 1-10. In another embodiment, an inactivating mutation in a gene encoding gD consists essentially of a mutation in which an alanine at amino acid 3 of HSV-1 gD or HSV-2 gD is mutated to a cysteine (A3C). In another embodiment, an inactivating mutation in a gene encoding gD consists of a mutation in which an alanine at amino acid 3 of HSV-1 gD or HSV-2 gD is mutated to a cysteine (A3C). In one embodiment, the numbering used to describe the location of the mutation refers to amino acid numbering of the mature peptide after cleaving of the signal sequence, which in one embodiment, is the first 25 amino acids for HSV-1 or HSV-2 gD, as is known in the art.

As provided herein and in one embodiment, a mutant HSV strain of the present invention comprising a mutation in gD has reduced virulence (Example 21) and ability to reach DRG (Example 22). In another embodiment, vaccination with a mutant HSV strain comprising a mutation in gD of the present invention protects against latent HSV infection (Example 23) after subsequent infection with virulent HSV. In another embodiment, the vaccination protects against disease caused by or associated with latent HSV infection. In another embodiment, the vaccination does not itself cause significant disease.

In some embodiments, any of the mutant HSV strains of and for use in the methods of this invention will comprise an inactivating mutation of the present invention, in any form or embodiment as described herein. In some embodiments, any of the mutant HSV strains of this invention will consist of an inactivating mutation of the present invention, in any form or embodiment as described herein. In some embodiments, the mutant HSV strains of this invention will consist essentially of an inactivating mutation of the present invention, in any form or embodiment as described herein. In some embodiments, the term "comprise" refers to the inclusion of the inactivating mutation, such as a mutation in gE or in gD, as well as inclusion of other mutations that may be known in the art. In some embodiments, the term "consisting essentially of" refers to a strain, whose only functional mutation is the indicated functional mutation, however, other mutations may be included that are not involved directly in the utility of the strain. In some embodiments, the term "consisting" refers to a strain, which contains mutation of a particular gene or a particular mutation.

In one embodiment, plasmid complementation may be used to complement the inactivating mutation, which in one embodiment, allows at least one round of infection with a mutant HSV of the invention.

In one embodiment, the present invention provides a composition for impeding formation of zosteriform lesions in a subject, the composition comprising a mutant HSV strain of the present invention.

In one embodiment, the present invention provides a composition for impeding herpetic ocular disease in a subject, the composition comprising a mutant HSV strain of the present invention.

In one embodiment, the present invention provides a composition for vaccinating a subject against an HSV infection, the composition comprising a mutant HSV strain of the present invention.

In one embodiment, the present invention provides a composition for impeding HSV infection in a subject, the composition comprising a mutant HSV strain of the present invention.

In one embodiment, the present invention provides a composition for impeding herpes-mediated encephalitis in a subject, the composition comprising a mutant HSV strain of the present invention.

In one embodiment, a gE protein of the present invention is homologous to a peptide disclosed or enumerated herein. The terms "homology," "homologous," etc., when in reference to any protein or peptide, refer, in one embodiment, to a percentage of amino acid (AA) residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

Homology is, in one embodiment, determined by computer algorithm for sequence alignment, by methods well described in the art. For example, computer algorithm analysis of nucleic acid sequence homology can include the utilization of any number of software packages available, such as, for example, the BLAST, DOMAIN, BEAUTY (BLAST Enhanced Alignment Utility), GENPEFT and TREMBL packages.

In one embodiment, "homology" refers to identity to a sequence selected from SEQ ID No: 2-7 of greater than 70%. In another embodiment, "homology" refers to identity to a sequence selected from SEQ ID No: 2-7 of greater than 72%. In another embodiment, "homology" refers to identity to one of SEQ ID No: 2-7 of greater than 75%. In another embodiment, "homology" refers to identity to a sequence selected from SEQ ID No: 2-7 of greater than 78%. In another embodiment, "homology" refers to identity to one of SEQ ID No: 2-7 of greater than 80%. In another embodiment, "homology" refers to identity to one of SEQ ID No: 2-7 of greater than 82%. In another embodiment, "homology" refers to identity to a sequence selected from SEQ ID No: 2-7 of greater than 83%. In another embodiment, "homology" refers to identity to one of SEQ ID No: 2-7 of greater than 85%. In another embodiment, "homology" refers to identity to one of SEQ ID No: 2-7 of greater than 87%. In another embodiment, "homology" refers to identity to a sequence selected from SEQ ID No: 2-7 of greater than 88%. In another embodiment, "homology" refers to identity to one of SEQ ID No: 2-7 of greater than 90%. In another embodiment, "homology" refers to identity to one of SEQ ID No: 2-7 of greater than 92%. In another embodiment, "homology" refers to identity to a sequence selected from SEQ ID No: 2-7 of greater than 93%. In another embodiment, "homology" refers to identity to one of SEQ ID No: 2-7 of greater than 95%. In another embodiment, "homology" refers to identity to a sequence selected from SEQ ID No: 2-7 of greater than 96%. In another embodiment, "homology" refers to identity to one of SEQ ID No: 2-7 of greater than 97%. In another embodiment, "homology" refers to identity to one of SEQ ID No: 2-7 of greater than 98%. In another embodiment, "homology" refers to identity to one of SEQ ID No: 2-7 of greater than 99%. In another embodiment, "homology" refers to identity to one of SEQ ID No: 2-7 of 100%.

In one embodiment, homology is determined via determination of candidate sequence hybridization, methods of which are well described in the art (See, for example, "Nucleic Acid Hybridization" Hames B D and Higgins S J, Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y.). In other embodiments, methods of hybridization are carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA.

Protein and/or peptide homology for any AA sequence listed herein is determined, in one embodiment, by methods well described in the art, including immunoblot analysis, or via computer algorithm analysis of AA sequences, utilizing any of a number of software packages available, via established methods. Some of these packages include the FASTA, BLAST, MPsrch or Scanps packages, and, in another embodiment, employ the use of the Smith and Waterman algorithms, and/or global/local or BLOCKS alignments for analysis, for example.

In one embodiment, "variant" refers to an amino acid or nucleic acid sequence (or in other embodiments, an organism or tissue) that is different from the majority of the population but is still sufficiently similar to the common mode to be considered to be one of them, for example splice variants.

In one embodiment, "isomer" refers to one of any of two or more substances that are composed of the same elements in the same proportions but differ in chemical and/or bological properties because of differences in the arrangement of atoms, which in one embodiment are stereoisomers, in another embodiment, constitutional isomers or tautomers. In one embodiment, an isomer is an optical isomer or entantiomer, a geometric isomer, a D- and L-isomer, positional isomer, or a cis-trans isomer.

In one embodiment of the present invention, "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA is, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al., Genes & Devel 16: 2491-96 and references cited therein). DNA can be, in other embodiments, in form of plasmid DNA, viral DNA, linear DNA, or chromosomal DNA or derivatives of these groups. In addition, these forms of DNA and RNA can be single-, double-, triple-, or quadruple-stranded. The term also includes, in another embodiment, artificial nucleic acids that contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane-modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al. Biochem Biophys Res Commun. 297:1075-84. The production and use of nucleic acids is known to those skilled in art and is described, for example, in Molecular Cloning, (2001), Sambrook and Russell, Eds., and Methods in Enzymology: Methods for molecular cloning in eukaryotic cells (2003) Purchio and G. C. Fareed.

In one embodiment, the present invention provides a kit comprising a compound or composition utilized in performing a method of the present invention. In another embodiment, the present invention provides a kit comprising a composition, tool, or instrument of the present invention.

"Contacting," in one embodiment, refers to directly contacting the target cell with a mutant HSV strain of the present invention. In another embodiment, "contacting" refers to indirectly contacting the target cell with a mutant HSV strain of the present invention. Thus, in one embodiment, methods of the present invention include methods in which the subject is contacted with a mutant HSV strain which is brought in contact with the target cell by diffusion or any other active transport or passive transport process known in the art by which compounds circulate within the body.

In one embodiment of the methods of the present invention, the mutant HSV strain is carried in the subjects' bloodstream to the target cell. In another embodiment, the mutant HSV strain is carried by diffusion to the target cell. In another embodiment, the mutant HSV strain is carried by active transport to the target cell. In another embodiment, the mutant HSV strain is administered to the subject in such a way that it directly contacts the target cell.

Pharmaceutical Compositions and Methods of Administration

In one embodiment, the methods of the present invention comprise administering a pharmaceutical composition comprising the mutant HSV strain and a pharmaceutically acceptable carrier.

"Pharmaceutical composition" refers, in one embodiment, to a therapeutically effective amount of the active ingredient, i.e. the mutant HSV strain, together with a pharmaceutically acceptable carrier or diluent. A "therapeutically effective amount" refers, in one embodiment, to that amount which provides a therapeutic effect for a given condition and administration regimen.

The pharmaceutical compositions containing the mutant HSV strain can be, in one embodiment, administered to a subject by any method known to a person skilled in the art, such as parenterally, transmucosally, transdermally, intramuscularly, intravenously, intra-dermally, subcutaneously, intra-peritonealy, intra-ventricularly, intra-cranially, intra-vaginally or intra-tumorally.

In another embodiment as described in the methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like.

Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In another embodiment, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Suitable topical formulations include gels, ointments, creams, lotions, drops and the like. For topical administration, the mutant HSV strain is prepared and applied as a solution, suspension, or emulsion in a physiologically acceptable diluent with or without a pharmaceutical carrier.

In another embodiment, the pharmaceutical compositions provided herein are controlled-release compositions, i.e. compositions in which the mutant HSV strain is released over a period of time after administration. Controlled- or sustained-release compositions include formulation in lipophilic depots (e.g. fatty acids, waxes, oils). In another embodiment, the composition is an immediate-release composition, i.e. a composition in which all the mutant HSV strain is released immediately after administration.

Each of the above additives, excipients, formulations and methods of administration represents a separate embodiment of the present invention.

EXPERIMENTAL DETAILS SECTION

Example 1

HSV$_{(gE\ NULL)}$ Does not Cause Disease

Materials and Experimental Methods (Examples 1-4)

Virus Strains

Wild-type HSV-1 strain NS, a low-passage-number clinical isolate, was used for generation of mutant viruses. To construct HSV-1$_{(gE\ null)}$, the entire gE coding sequence was excised from pCMV3gE-1 with XbaI and cloned into pSPT18. pSPT18 has the sequence:

```
                                        (SEQ ID No: 1)
gaatacaagcttgcatgcctgcaggtcgactctagaggatccccgggt accgagctcgaattccggtctccctatagtgagtcgtattaatttcga taagccagctgggcctcgcgcgtttcggtgatgacggtgaaaacctct gacacatgcagctcccggagacggtcacagcttgtctgtaagcggatg ccgggagcagacaagcccgtcagggcgcgtcagcgggtgttggcgggt gtcggggcgcagccatgacccagtcacgtagcgatagcggagtgtata tactggcttaactatgcggcatcagagcagattgtactgagagtgcac catatgcggtgtgaaataccgcacagatgcgtaaggagaaaataccgc atcaggcgctcttccgcttcctcgctcactgactcgctgcgctcggtc gttcggctgcggcgagcggtatcagctcactcaaaggcggtaatacgg ttatccacagaatcaggggataacgcaggaaagaacatgtgagcaaag gccagcaaaaggccaggaaccgtaaaaaggccgcgttctggcgttttt ccataggctccgcccccctgacgagcatcacaaaaatcgacgctcaag tcagaggtggcgaaacccgacaggactataaagataccaggcgtttcc ccctggaagctccctcgtgcgctctcctgttccgaccctgccgcttac cggatacctgtccgcctttctcccttcgggaagcgtggcgctttctca atgctcacgctgtaggtatctcagttcggtgtaggtcgttcgctccaa gctgggctgtgtgcacgaaccccccgttcagcccgaccgctgcgcctt atccggtaactatcgtcttgagtccaacccggtaagacacgacttatc gccactggcagcagccactggtaacaggattagcagagcgaggtatgt aggcggtgctacagagttcttgaagtggtggcctaactacggctacac tagaaggacagtatttggtatctgcgctctgctgaagccagttacctt cggaaaaagagttggtagctcttgatccggcaaacaaaccaccgctgg tagcggtggtttttttgtttgcaagcagcagattacgcgcagaaaaaa aggatctcaagaagatcctttgatcttttctacggggtctgacgctca gtggaacgaaaactcacgttaagggattttggtcatgagattatcaaa aaggatcttcacctagatccttttaaattaaaaatgaagttttaaatc aatctaaagtatatatgagtaaacttggtctgacagttaccaatgctt aatcagtgaggcacctatctcagcgatctgtctatttcgttcatccat agttgcctgactccccgtcgtgtagataactacgatacgggagggctt accatctggccccagtgctgcaatgataccgcgagacccacgctcacc ggctccagatttatcagcaataaaccagccagccggaagggccgagcg cagaagtggtcctgcaactttatccgcctccatccagtctattaattg ttgccgggaagctagagtaagtagttcgccagttaatagtttgcgcaa cgttgttgccattgctacaggcatcgtggtgtcacgctcgtcgtttgg tatggcttcattcagctccggttcccaacgatcaaggcgagttacatg atccccatgttgtgcaaaaaagcggttagctccttcggtcctccgat cgttgtcagaagtaagttggccgcagtgttatcactcatggttatggc agcactgcataattctcttactgtcatgccatccgtaagatgcttttc tgtgactggtgagtactcaaccaagtcattctgagaatagtgtatgcg gcgaccgagttgctcttgcccggcgtcaatacgggataataccgcgcc acatagcagaacttaaaagtgctcatcattggaaaacgttcttcggg gcgaaaactctcaaggatcttaccgctgttgagatccagttcgatgta acccactcgtgcacccaactgatcttcagcatcttttactttcaccag cgtttctgggtgagcaaaaacaggaaggcaaaatgccgcaaaaaggg aataagggcgacacggaaatgttgaatactcatactcttccttttca
```

-continued

```
atattattgaagcatttatcagggttattgtctcatgagcggatacat atttgaatgtatttagaaaaataaacaaatagggttccgcgcacatt tccccgaaaagtgccacctgacgtctaagaaaccattattatcatgac attaacctataaaaataggcgtatcacgaggcccttcgtctcgcgcg tttcggtgatgacggtgaaaacctctgacacatgcagctcccggagac ggtcacagcttgtctgtaagcggatgccgggagcagacaagcccgtca gggcgcgtcagcgggtgttggcgggtgtcggggctggcttaactatgc ggcatcagagcagattgtactgagagtgcaccatatcgacgctctccc ttatgcgactcctgcattaggaagcagcccagtagtaggttgaggccg ttgagcaccgccgccgcaaggaatggtgcatgcaaggagatggcgccc aacagtcccccggccacgggcctgccaccatacccacgccgaaacaag cgctcatgagcccgaagtggcgagcccgatcttcccatcggtgatgtc ggcgatataggcgccagcaaccgcacctgtggcgccggtgatgccggc cacgatgcgtccggcgtagaggatctggctagcgatgaccctgctgat tggttcgctgaccatttccgggtgcgggacggcgttaccagaaactca gaaggttcgtccaaccaaaccgactctgacggcagtttacgagagaga tgatagggtctgcttcagtaagccagatgctacacaattaggcttgta catattgtcgttagaacgcggctacaattaatacataaccttatgtat catacacatacgatttaggtgacactata.
```

Figure 5:
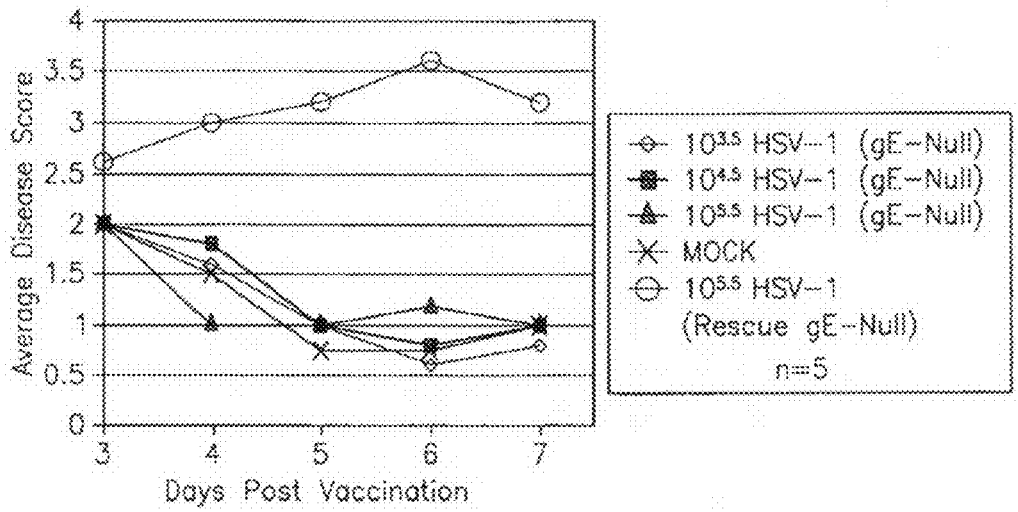
Figure 6:
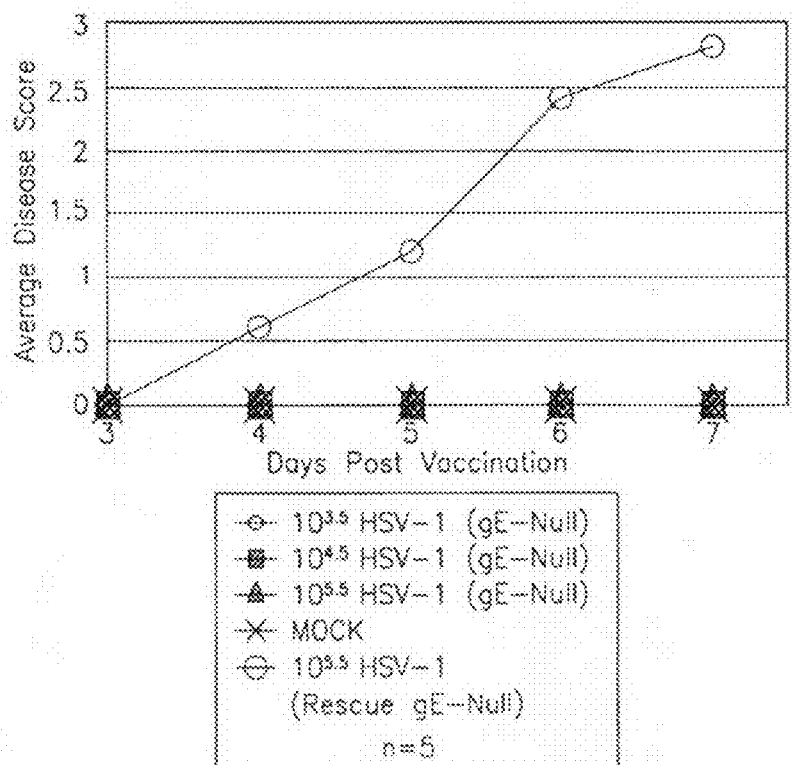
Figure 7:
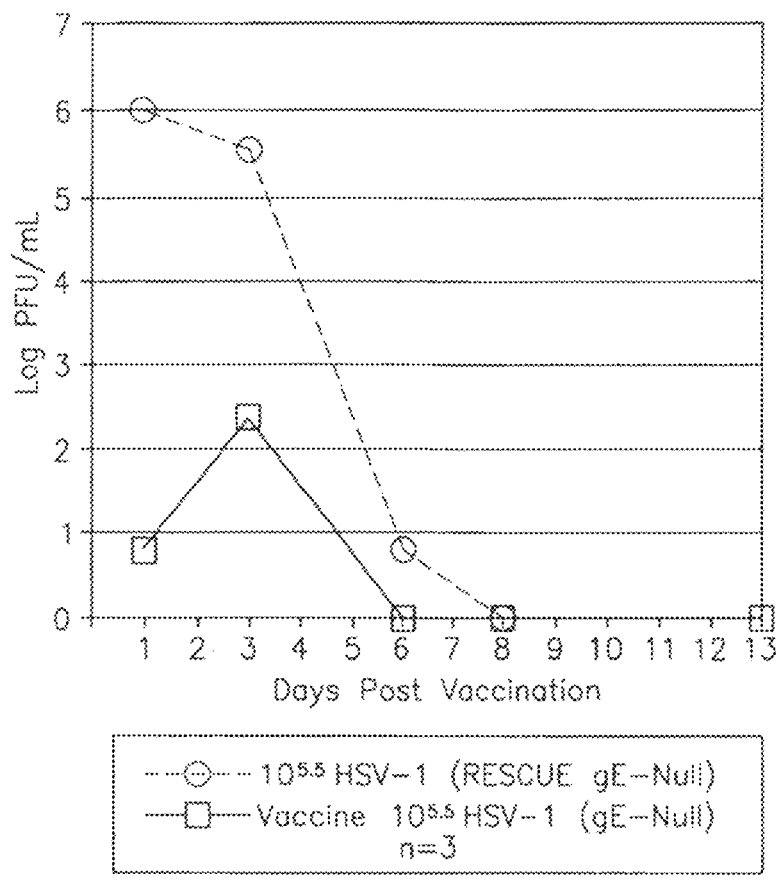
Figure 8:
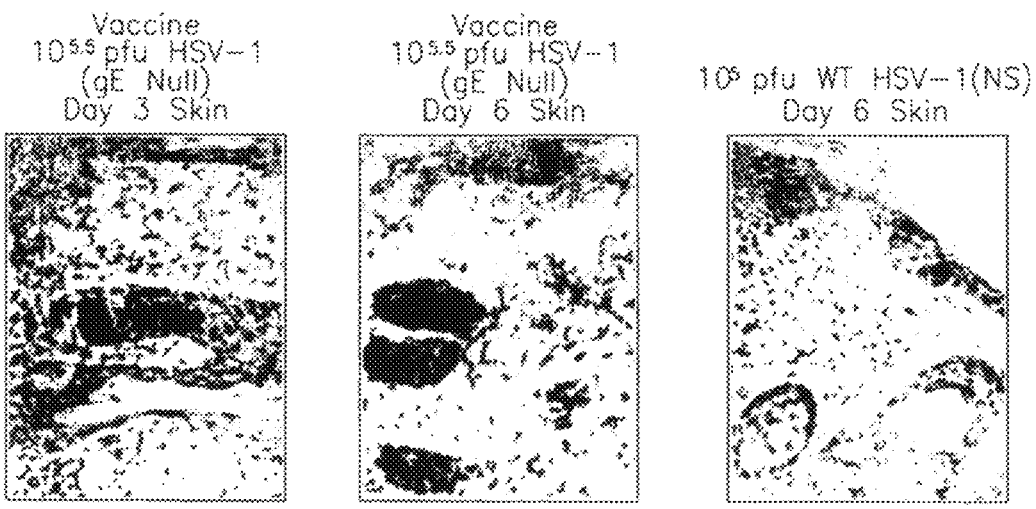
Figure 9:
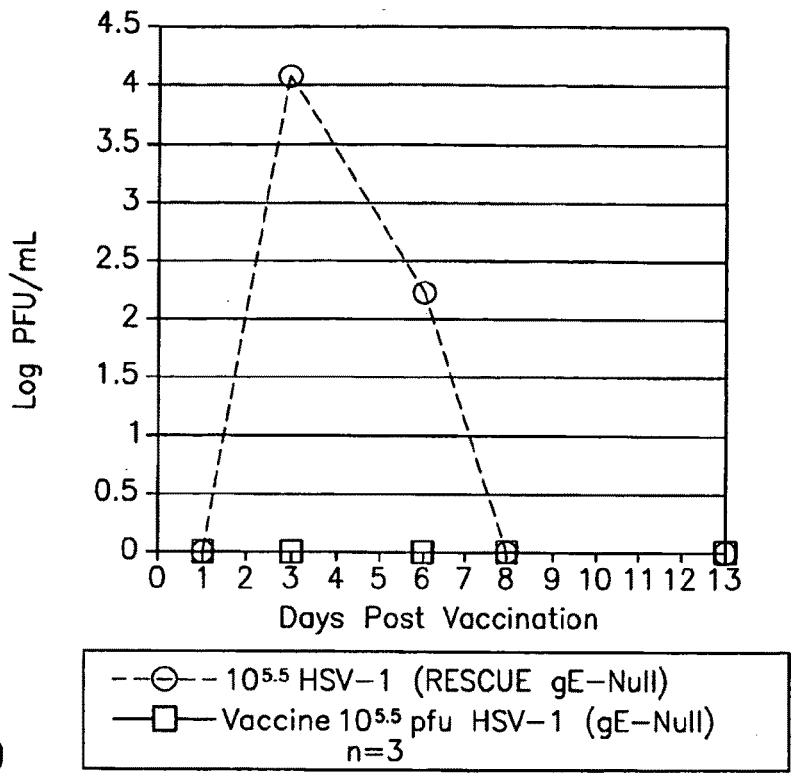
Figure 10:
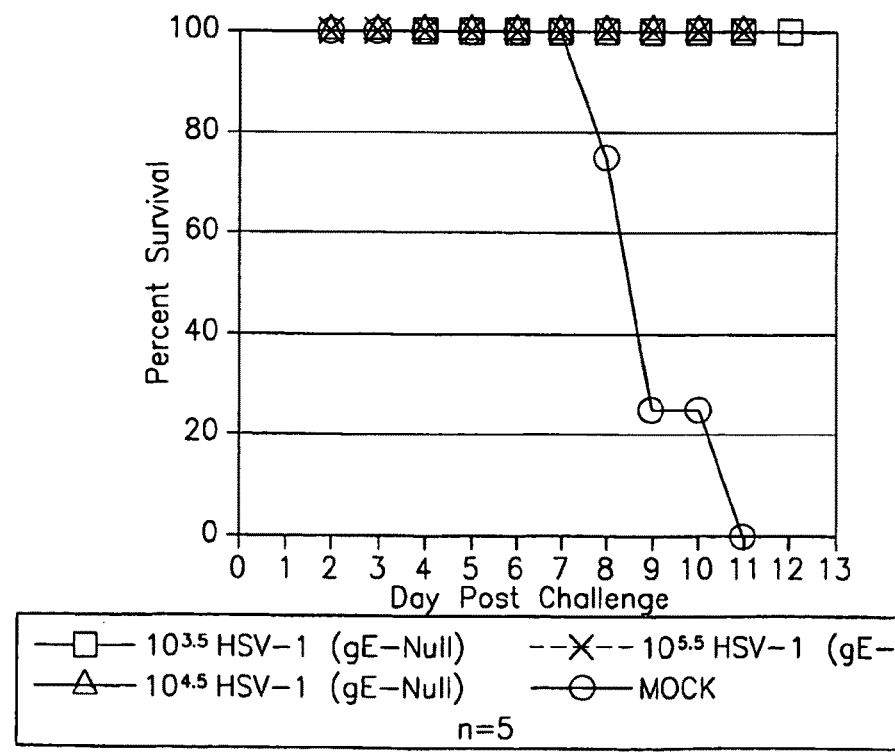
Figure 11:
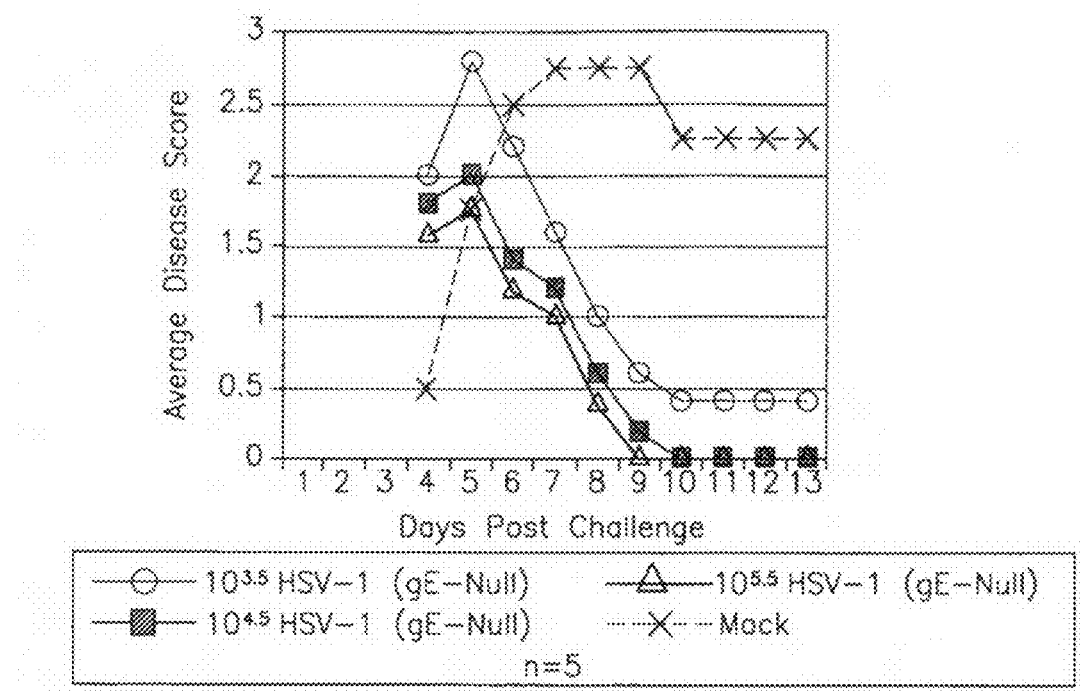
Figure 12:
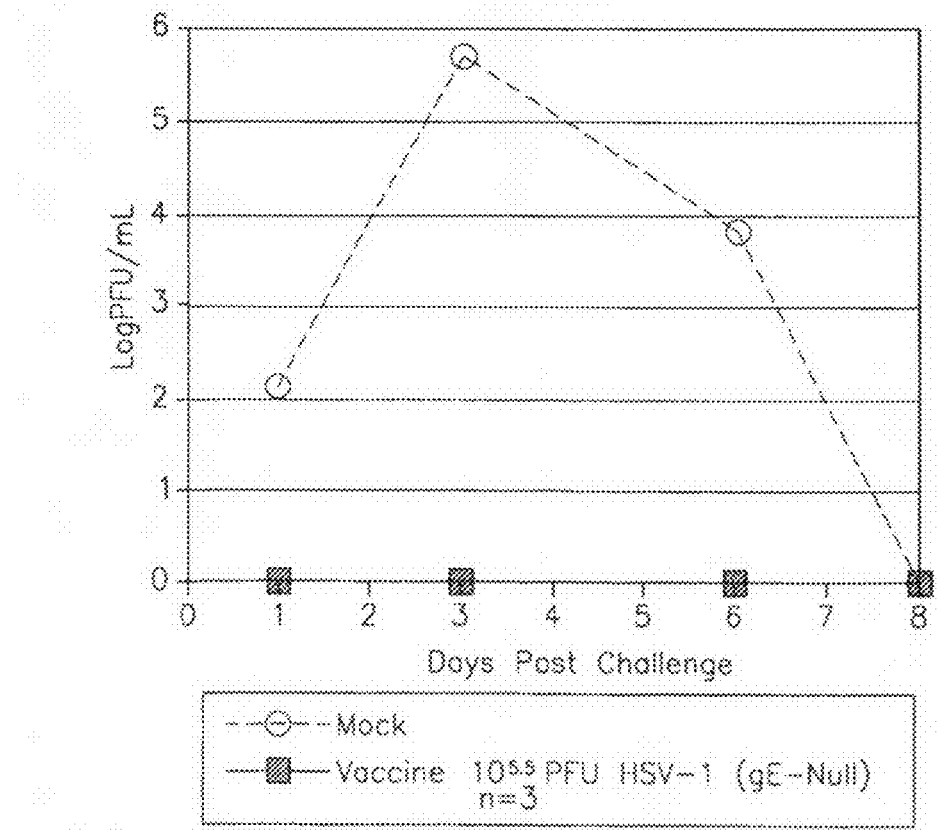
Figure 13:
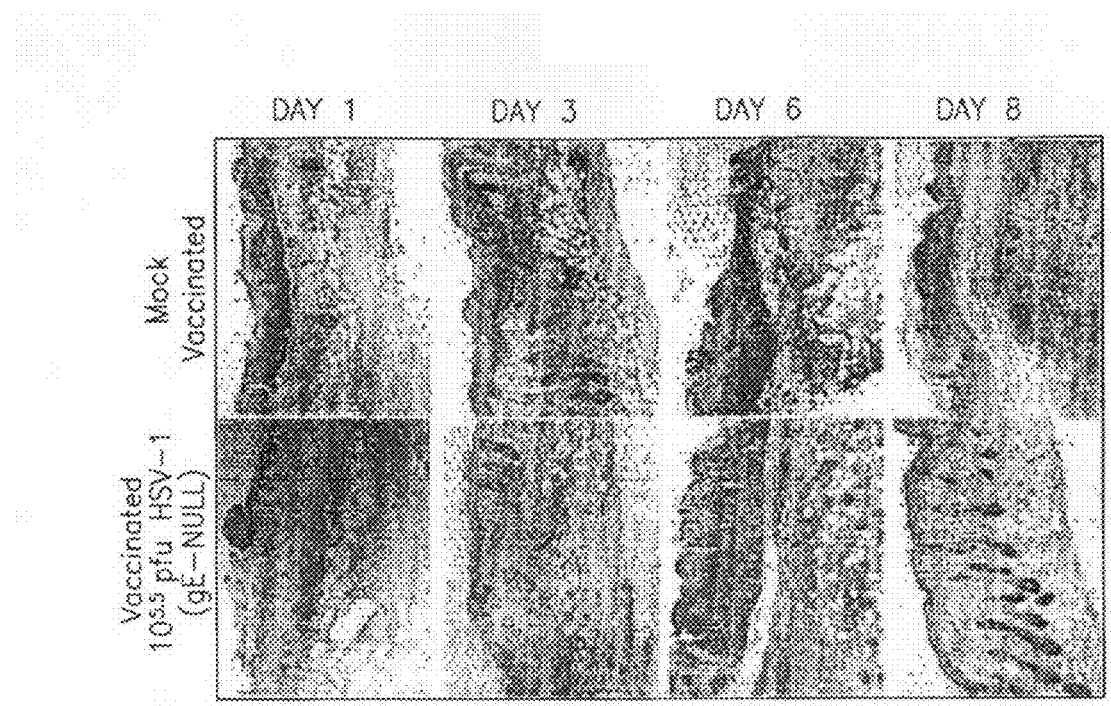
Figure 14:
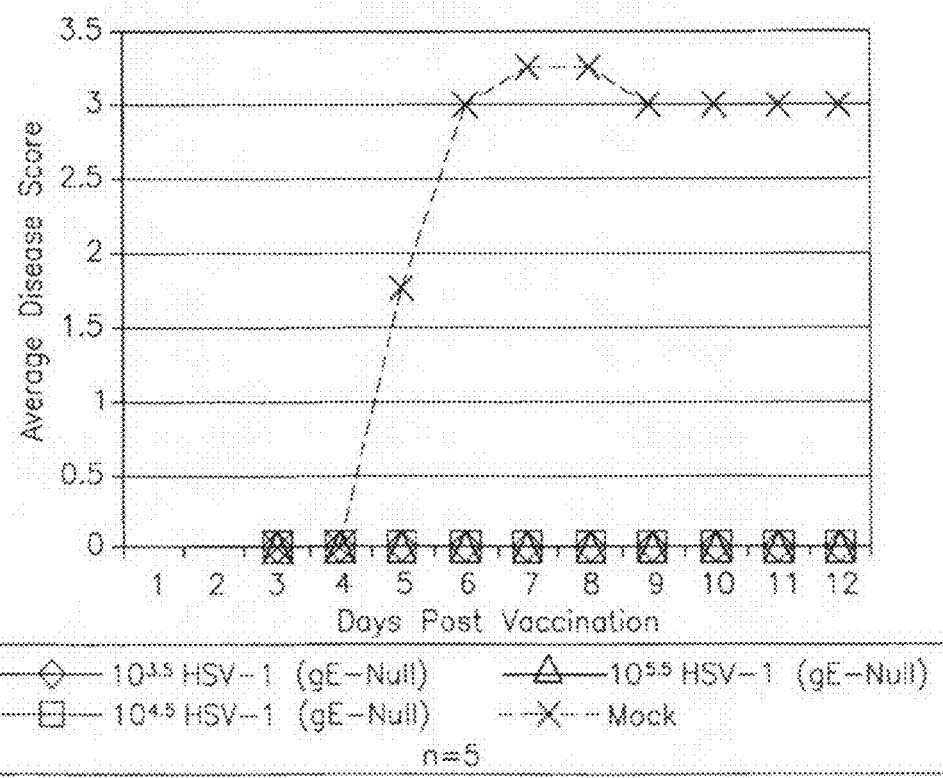
Figures 15, 16:
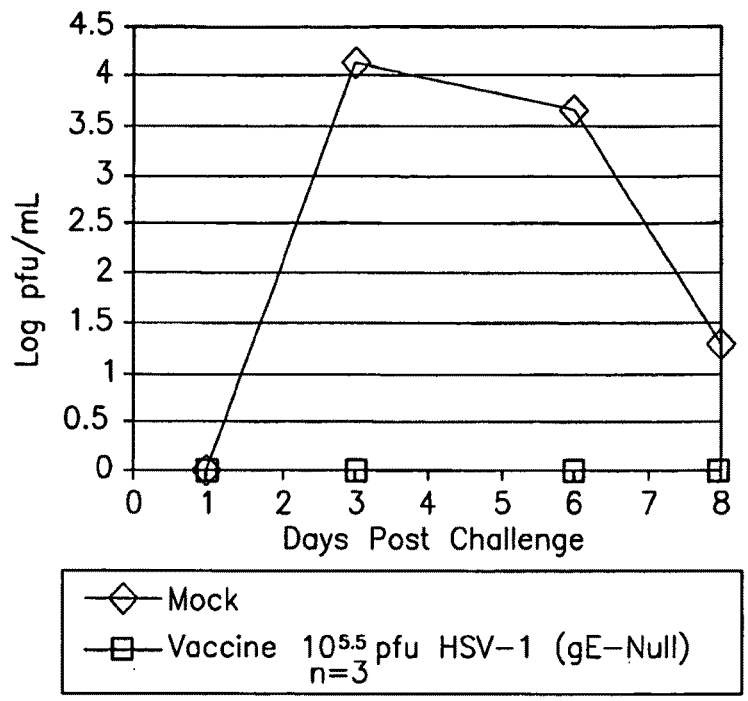

A 1.1-kb HpaI-BglII fragment from amino acids (AA) 124-508 was excised, and the HpaI site was changed to a BglII site. A 4.3-kb fragment derived from pD6P containing the *Escherichia coli* p-galactosidase gene (β-gal) under the control of the HSV ICP6 promoter was cloned into the BglII site. The resultant vector contains 374 bp of NS DNA sequences 5' and 225 bp 3' of the ICP6::lacZ cassette and was used to construct the gE null virus. The XbaI fragment containing the flanking sequence vector was isolated, and 750 ng was cotransfected into Vero cells with 1.0 Ng of NS DNA by calcium phosphate transfection. The DNA-calcium phosphate mixture was removed, and cells were shocked with 15% glycerol. Cells were harvested when cytopathic effects were noted in 30-40% of cells and were sonicated to prepare a virus pool. Recombinant gE null virus expressing β-gal was selected by infecting Vero cells and overlaying with 0.5% agarose, 5.0% fetal bovine serum (FBS), and 300 μg of 5-bromo-D-galactopyranoside (X-Gal). Blue plaques were picked and purified twice in X-Gal agarose overlay and once by limiting dilution. Virus was purified from supernatant fluids of infected Vero cells on a 5-70% sucrose gradient.

HSV-$1_{(Rescue\ gE\ null)}$ was prepared by co-transfection of Vero cells with 1.0 μg of NS-gEnull DNA and 1.5 μg of wild-type gE fragment purified from pCMV3gE-1, which was obtained by digesting HSV-1 (NS) DNA with NruI. Progeny viruses were examined by immunoperoxidase staining using anti-gE MAb 1BA10 to confirm expression of gE on the surface of infected cells. Plaques were purified by limiting dilution, and virus pools were prepared.

Virus stocks were grown on confluent Vero cells (an African green monkey kidney epithelial cell line) at an MOI of 2.0. 24 hours post-infection, cells were scraped in the media and centrifuged at 3,000×g. All but 1 mL of supernatant was removed, and cells were resuspended, sonicated for 3 seconds and distributed into 50 mcL (microliter) aliquots. For mock infections, similar aliquots were made using uninfected cells.

Mouse Flank Infection Protocol

All experimental protocols were approved by the University of Pennsylvania animal and laboratory resources IACUC committee. Five- to six-week-old BalbC mice (National Cancer Institute) were allowed to acclimate to the biosafety level 2 animal facility with constant temperature and photoperiod (12 hours of light, 12 hours of darkness) for 1 week. Mice were shaved and depilated with depilatory cream comprising calcium hydroxide and potassium thyoglycolate (NAIR™) along the right flank (for vaccination) or the left flank (for challenge), then washed with warm water. The next day, mice were anesthetized via intraperitoneal injection of 75 mcL of 14.3 mg/ml ketamine and 1.8 mg/ml xylazine in PBS, then infected by making 60 superficial scratches in a 1 $cm^2$ area of the flank, 1 cm dorsal to the spine, with a $26^3/8$-gauge needle through a 10 mcL droplet containing $5\times10^3$-$5\times10^5$ pfu HSV (FIG. 1). In HSV flank-infected mice, secondary spread back to the skin from the neurons of one or more spinal ganglia results in a belt-like lesion (FIG. 2). Mice were sacrificed by asphyxiation with $C0_2$, followed by cervical dis-location. Mice were observed at 24-hour intervals starting at day 3 post-inoculation to record the appearance and severity of skin lesions and illness. A standardized scoring system to describe lesion severity was used to provide consistency in observations (FIG. 3).

Vaccination and Challenge

For vaccination, mice were infected by making scratches through the inoculum, containing either HSV-1(gE null) or virus-free cell lysate (described above), on the right flank. Mice were challenged 28 days later on the opposite (left) flank by scratching through a droplet containing $1\times10^5$ pfu HSV-1(NS).

Dissections of Dorsal Root Ganglia and Skin

Dorsal root ganglia (DRG) along either the right (for analysis of HSV-$1_{(gE\ null)}$ vaccination or HSV-$1_{(Rescue\ gE\ null)}$ infection), or left (for analysis of HSV-1(NS) challenge) sides of the spinal column were removed, pooled, and placed in 110 mcL DMEM (2.5% FBS) and frozen at −80° C. until analysis.

A 1-$cm^2$ area of skin at the site of inoculation was removed. Half of the sample was placed in a tube containing 110 mcL DMEM (2.5% FBS) and frozen at −80° C. until analysis. The other half was placed on an index card with like-samples and immersed in 4% paraformaldehyde in 1×PBS for 24 hours at 4° C., then the solution was replaced with 1×PBS. Samples remained at 4° C. until processing for histological analysis.

Sectioning, Histology and Immunohistochemistry

Paraffin embedding, sectioning and staining of skin samples was performed by the Pathology Core Facility at Children's Hospital of Philadelphia. Skin sections were stained for HSV-1 antigen using anti-HSV-1 rabbit polyclonal antibody (DAKO) and counter-stained with hematoxylin.

Results

Groups of five mice were flank-infected by scarification of $10^{3.5}$, $10^{4.5}$, or $10^{5.5}$ plaque-forming units (pfu) of the vaccine strain, HSV-$1_{(gE\ null)}$. For comparison to the virulent form of HSV-1, another group of five mice was flank-infected with $10^{5.5}$ pfu of HSV-$1_{(Rescue\ gE\ null)}$ the vaccine strain backbone with the gene encoding gE restored. HSV-$1_{(Rescue\ gE\ null)}$ infection resulted in illness and 60% mortality (FIG. 4). However, no clinical signs of disease, illness or death occurred following HSV-$1_{(gE\ null)}$ vaccination.

In addition, the HSV-1$_{(Rescue\ gE\ null)}$ infection caused severe primary lesions that appeared ulcerative and necrotic (FIG. 5). In contrast, HSV-1$_{(gE\ null)}$ infection caused a mild skin pathology at the site of inoculation indistinguishable from that of mock vaccination. Thus, all or essentially all of the skin pathology following the administration of HSV-1$_{(gE\ null)}$ resulted from the process of scratch inoculation itself.

These findings show that infection with gE null herpes viruses does not cause disease.

Example 2

HSV$_{(gE\ NULL)}$ Does not Spread within Sensory Neurons

HSV-$1_{(Rescue\ gE\ null)}$ infection caused severe secondary (zosteriform) ulcerative and necrotic lesions that first appeared at 4-5 (days post-infection) dpi (FIG. 6). In contrast, no secondary lesions were seen following HSV-$1_{(gE\ null)}$ infection. Since secondary lesion formation along the dermatome depends on the ability of the virus to spread along neurons from the skin to the ganglia, and then back again, these results show that the vaccine is not able to spread within sensory neurons. Therefore, HSV$_{(gE\ null)}$ is unable to cause recurrent infection.

Example 3

HSV$_{(gE\ NULL)}$ Replicates within Skin Cells

To determine the extent of replication of HSV-$1_{(gE\ null)}$ in skin cells, mice (n=3) were infected with HSV-$1_{(gE\ null)}$ or virulent HSV-$1_{(Rescue\ gE\ null)}$. On days 1, 3, 6, 8 and 13 post-inoculation, mice were sacrificed, skin at the site of inoculation was removed, and DRG from the right side of each mouse were pooled. Titering to determine viral content of the homogenized tissue revealed that HSV-$1_{(gE\ null)}$ replicated in skin following vaccination, but less extensively than HSV-$1_{(Rescue\ gE\text{-}null)}$ (FIG. 7). Further, HSV-$1_{(gE\ null)}$-vaccinated skin was infiltrated by immune cells, and the virus was cleared by day 6 (FIG. 8).

These results show that HSV$_{(gE\ null)}$ replicates in the skin, and thus is expected to elicit an inflammatory response by the host.

Levels of HSV-$1_{(Rescue\ gE\ null)}$ exceeded that of HSV-$1_{(gE\ null)}$ by 4 orders of magnitude (FIG. 9). In addition, no infectious virus was detected in DRG of mice infected with HSV-$1_{(gE\ null)}$. The absence of the characteristic belt-like pattern of lesions and of detectable virus in the ganglia confirmed that no neuronal viral spread occurred after HSV-$1_{(gE\ null)}$ vaccination.

Thus, HSV infection in the absence of gE is limited to the skin of the host, and the immune system is able to detect and clear the virus rapidly.

Example 4

HSV-$1_{(gE\ NULL)}$ Vaccination is Protective Against Wild-Type HSV-1 Infection Mock-vaccinated or HSV-$1_{(gE\ null)}$ vaccinated mice were challenged with a lethal dose of $10^5$ pfu WT HSV-1 (NS strain) 28 days after vaccination. Whereas 100% of mock-vaccinated mice died following challenge, 100% of HSV-$1_{(gE\ null)}$-vaccinated mice survived the lethal challenge (FIG. 10). All tested doses of HSV-$1_{(gE\ null)}$ ($10^{3.5}$, $10^{4.5}$, and $10^{5.5}$ pfu) were protective against challenge. Additionally, very little primary (inoculation site) disease was observed after challenge of the HSV-$1_{(gE\ null)}$-vaccinated mice (FIG. 11). Vaccinated mice had undetectable levels of challenge virus in skin, at least 5 orders of magnitude less than mock-vaccinated mice (FIG. 12).

In contrast to the severely diseased mock-vaccinated mice, primary disease healed rapidly in vaccinated mice. Confirming this observation, immunohistochemistry of equivalent skin samples demonstrated the presence of very little antigen in vaccinated mice on day 3, and clearance by day 6 (FIG. 13). Histological analyses also revealed that vaccinated mice had significant infiltration of immune cells, showing that the vaccine successfully primed the host immune system.

Unlike the severe dermatome lesions resulting from zosteriform spread of the virus in mock-vaccinated mice, no zosteriform disease was seen in vaccinated mice (FIG. 14). In addition, viral titers in pulverized DRG were undetectable in vaccinated mice and thus, at least 4 orders of magnitude less than in mock-vaccinated mice (FIG. 15).

Example 5

HSV$_{(gE\ NULL)}$ Vaccination Prevents Establishment of Latent Wild-Type HSV-1 Infection after Subsequent Challenge

Materials and Experimental Method

Recovery of Infectious Virus from Tissues

DRG and skin samples were removed from mice immediately after sacrifice (at 1, 3, 6, 8 or 13 dpi). Three mice were infected for each data point, but like tissues from these mice were analyzed individually. Tissues were placed in 110 mcL DMEM containing 2.5% FBS and stored at −80° C. until analysis. To determine viral titer, tissue was thawed and pulverized with a disposable pestle. Infectious virus in 50 mcL of the supernatant, serially diluted (1:10, 1:100 and 1:1000), was quantified by plaque assay on confluent Vero cells in 12-well dishes.

Explant of DRG

To recover infectious virus from latently infected mice, DRG were removed from the same (right) side of infection with HSV-$1_{(gE\ null)}$. All DRG from an individual mouse were placed in one well of a 12-well dish of confluent Vero cells bathed in DMEM (2.5% FBS). Medium was changed every 2 days and cells were monitored for signs of CPE, an indication that DRG contained infectious virus.

Results

DRG were removed from vaccinated mice, 28 days post-challenge, and explanted in order to reactivate latent challenge virus. Reactivation from associated neurons of only 1/15 of the vaccinated mice occurred upon removal (FIG. 16).

Results of this and the previous Example show that HSV$_{(gE\ null)}$ protects mice from neuronal infection upon challenge and from developing latent infection typically associated with WT HSV infections.

Example 6

Vaccination of Mice with HSV-1ΔgE Cross Protects Against HSV-2 Challenge

Materials and Experimental Methods

Female Balb/C mice, 6-8 weeks old, were acclimated to the animal facility for 10 days. Mice were anesthetized and shaved and hair was removed with depilatory cream (NAIR™) treatment of the right flank. The following day, anesthetized mice were mock-vaccinated or vaccinated with $5 \times 10^5$ pfu HSV-1.DELTA.gE (which is referred to, in one embodiment, as gE null) by scratching 60 times through a 10 mcl (microliter) droplet of inoculum with a 26 (5/8)-gauge needle. The opposite flank (left side) of each mouse was shaved and denuded as before, twenty-seven days later. Mice were challenged the following day (day 28) by scratch inoculation of $10^5$ pfu HSV-2 (strain 2.12). Mice were observed and scored daily for inoculation site disease, zosteriform disease and survival. (Scoring: 0=no disease 4=severe necrotic disease). Error bars represent the standard error of the mean (SEM).

Results

Figure 17:
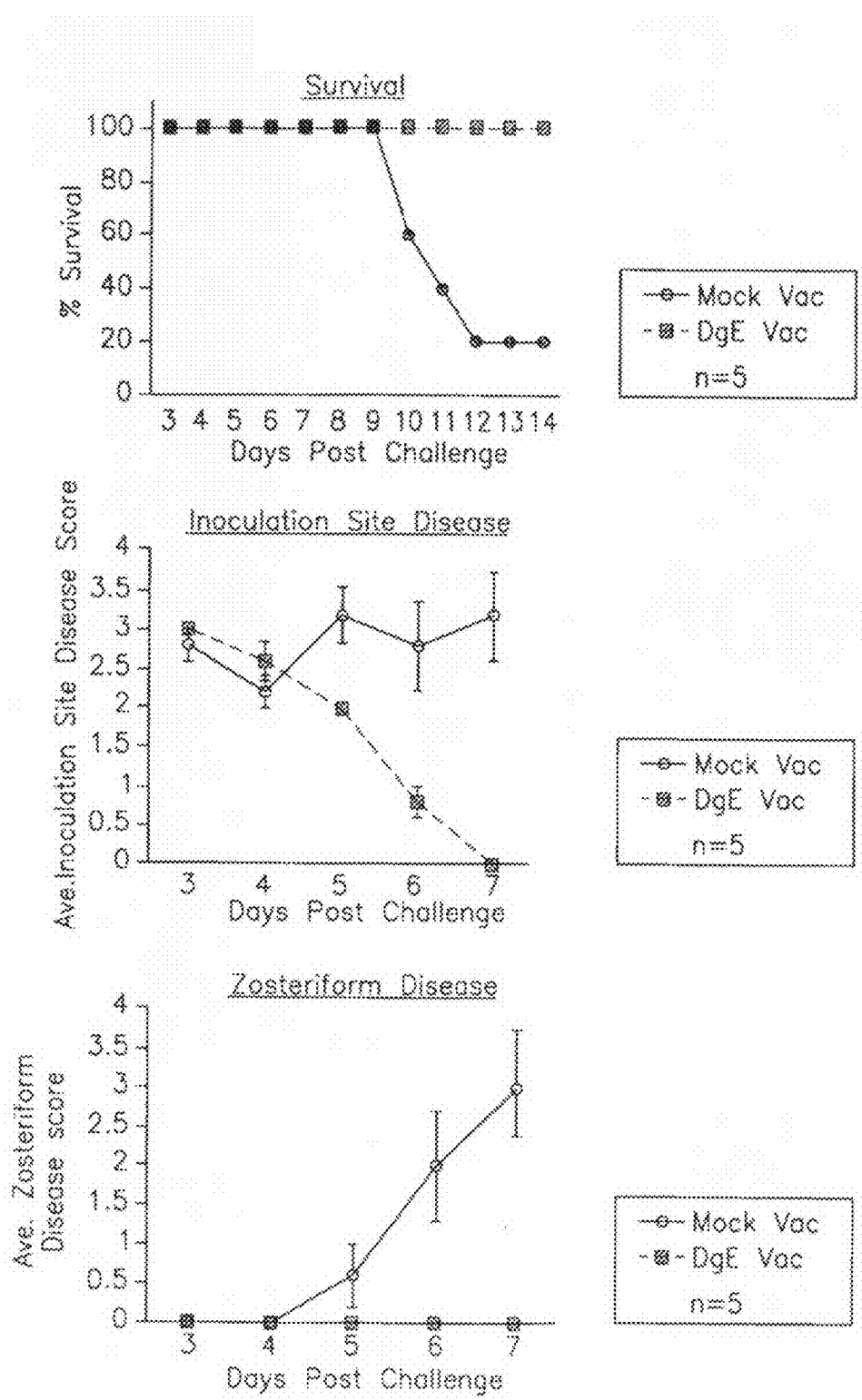

To test the ability of HSV-1ΔgE vaccination to protect against HSV-2 disease, HSV-1ΔgE-vaccinated mice were epidermally challenged with wild-type HSV-2. None of the HSV-1ΔgE vaccinated mice died, while 80% of mock vaccinated mice died (FIG. 17, top panel). Vaccinated mice exhibited inoculation site disease that healed rapidly compared to the unvaccinated mice (FIG. 17, middle panel). Additionally, vaccinated mice were completely protected from the zosteriform disease and death observed in the mock-vaccinated mice (FIG. 17, bottom panel).

Thus, ΔgE HSV vaccination is capable of protecting subjects against heterologous HSV disease, even of a different species of herpes simplex.

Example 7

Vaccination with HSV-1ΔgE Protects Against HSV-1(KOS) and Inhibits Establishment of HSV-1 Latency Materials and Experimental Methods Vaccination and assessment of disease were performed as described for the previous Example, except that $5 \times 10^5$ pfu HSV-1, strain KOS, was used for the challenge. For measurement of latent infection, mice were sacrificed 41 d post-challenge, and DRG from both right and left sides were removed, placed in DMEM/10% FBS, minced with scissors, and explanted onto sub-confluent Vero cell monolayers. Cultures were monitored daily for 20 d for plaque formation, indicative of reactivation from latency.

Results

Figure 18:
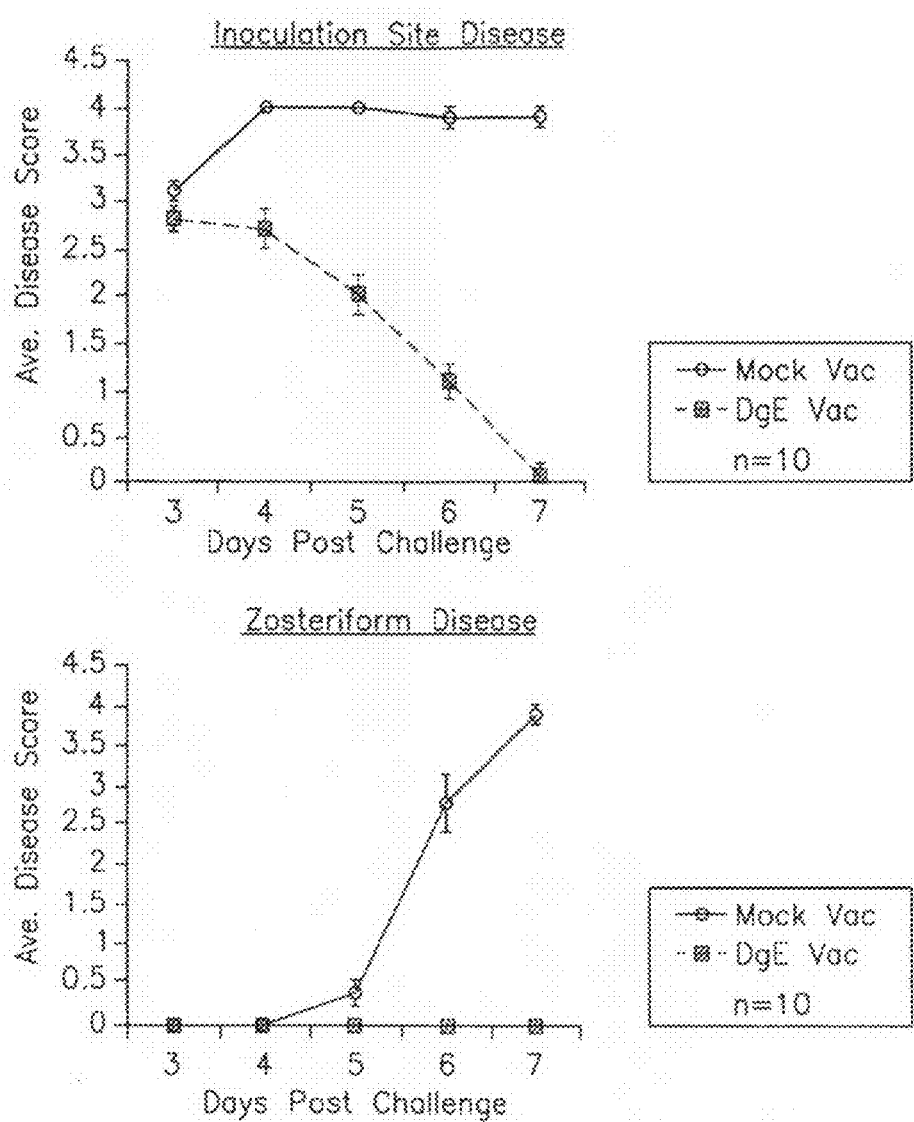

This experiment tested the ability of HSV-1ΔgE vaccination to protect mice from the disease associated with a heterologous HSV-1 wild-type strain. HSV-1ΔgE-vaccinated mice challenged with wild-type HSV-1, strain KOS, exhibited inoculation site disease that healed rapidly compared to unvaccinated mice (FIG. 18, top panel). Additionally, HSV-1ΔgE vaccination protected HSV-1 KOS-challenged mice completely against zosteriform disease (FIG. 18, middle panel). Since HSV-1 KOS infection of mice is not lethal, this strain was utilized to compare viral reactivation from latency in mock-versus HSV-1ΔgE-vaccinated mice at 4 weeks post-challenge. In mock-vaccinated mice, HSV-1(KOS) virus reactivated from explanted DRG in 100% of mice (n=10), whereas only 1/10 HSV-1ΔgE vaccinated mice (10%) exhibited reactivation (FIG. 18, table in bottom panel), which could have been latent infection by either the vaccine or the challenge virus. Therefore, HSV-1ΔgE vaccination is effective at protecting mice from both disease and establishment of latency by heterologous HSV viruses.

Example 8

Vaccination with HSV-1ΔgE Protects Against HSV-1 Vaginal Challenge

Materials and Experimental Methods

Vaccination was performed as described for Example 6. Medroxyprogesterone acetate (2 mg) (Sicor Pharmaceuticals, Inc., Irvine Calif.), diluted to 100 mcl total volume in a 0.9% NaCl/10 mM HEPES buffer, was injected subcutaneously 33 days later into the neck area of each mouse. Five days later (day 38), mice were anesthetized, intra-vaginally swabbed with a calcium alginate swab dipped in PBS, and challenged by intra-vaginal instillation of $5 \times 10^5$ pfu HSV-1 (strain NS). Mice were allowed to recover in their cages, resting in a prone position. Challenged mice were observed daily for vaginal disease and survival. Daily intra-vaginal swabs were taken for analysis by viral titering on Vero cells.

Results

Figure 19A:
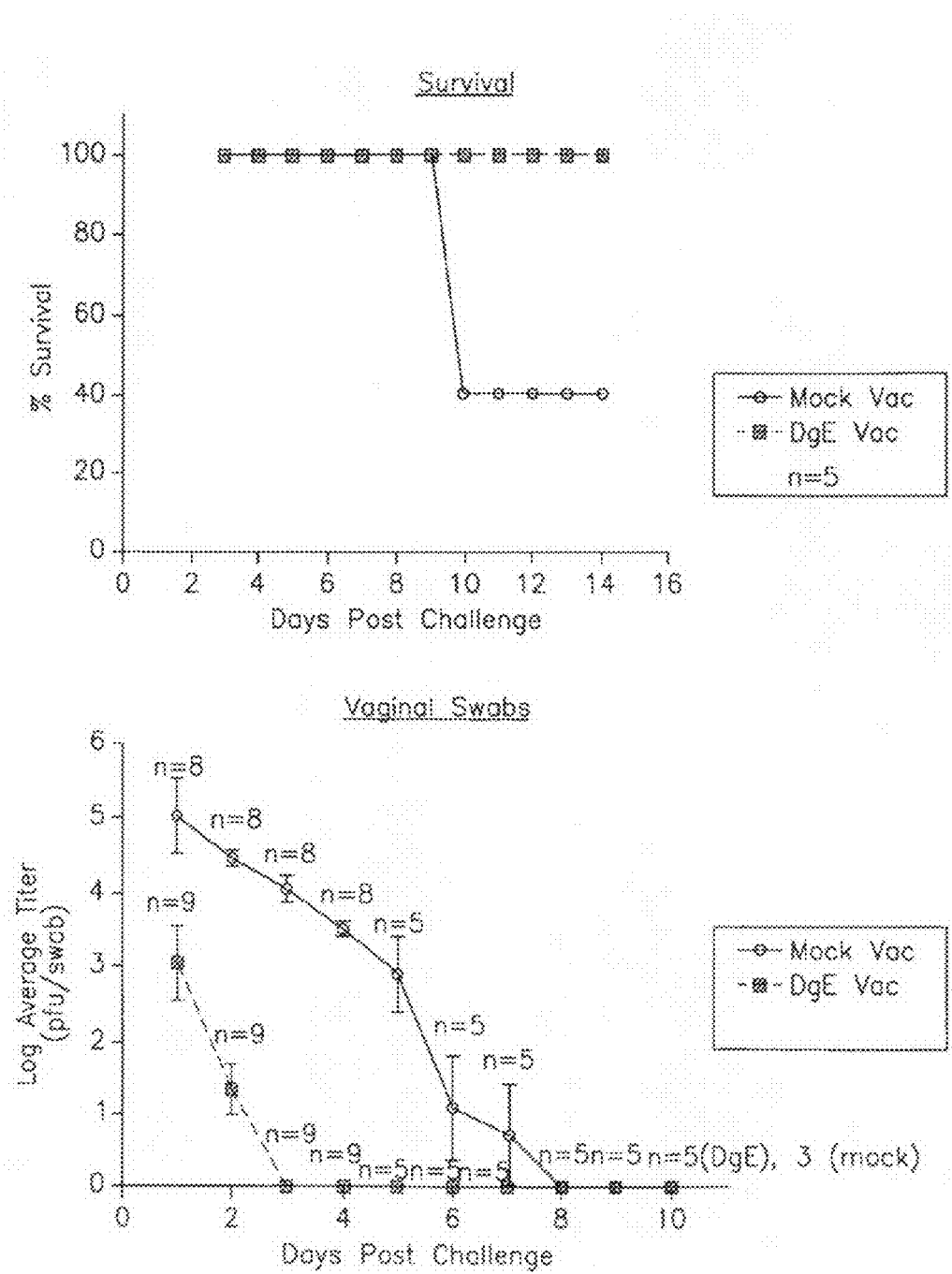
Figure 19B:
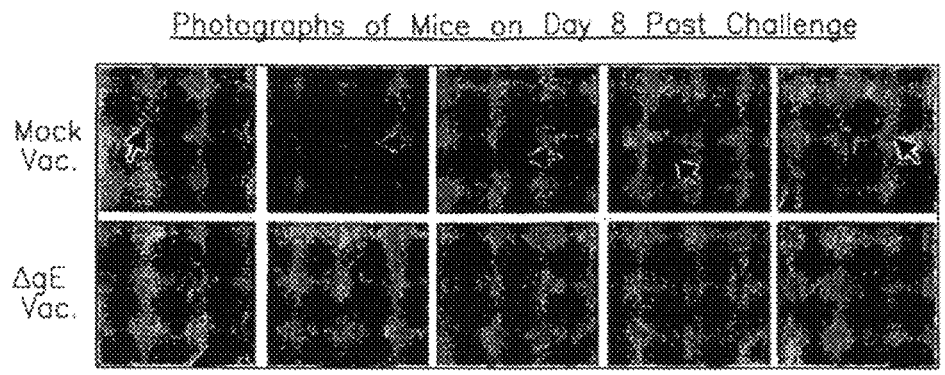

The ability of HSV-1ΔgE vaccination to protect against vaginal challenge with wild-type HSV-1 was tested. All mice vaccinated with HSV-1ΔgE survived the challenge, whereas 60% of mock-vaccinated mice succumbed (FIG. 19A, top panel). All mock-vaccinated mice showed some sign of visible disease in the vaginal area; however HSV-1ΔgE-vaccinated mice showed no obvious visible signs of disease (FIG. 19B). By day 1 post-vaginal challenge, HSV-1ΔgE-vaccinated mice had 100-fold less infectious virus than mock-vaccinated animals, as detected in vaginal swab samples. By day three post-challenge, no infectious virus was detected in swabs from HSV-1ΔgE-vaccinated mice, a value that is at least 30,000-fold less than mock-vaccinated mice on the same day. Additionally, infection of HSV-1ΔgE-vaccinated mice cleared nearly three times faster than mock-vaccinated mice (FIG. 19A, bottom panel). Thus, vaccination with HSV-1Δprotects from death and disease associated with HSV-1 vaginal challenge and confers the ability to rapidly clear HSV infection.

Example 9

Vaccination with HSV-1ΔgE by Epidermal, Subcutaneous, and Intramuscular Routes Protects Against HSV-1 Challenge Materials and Experimental Methods Vaccination was performed with $5 \times 10^5$ pfu HSV-1ΔgE by scratching 60 times through a 10 mcl droplet of inoculum with a 26 (5/8)-gauge needle, injection of 100 mcl inoculum into the scruff of the neck subcutaneously, or by intramuscular injection of 100 mcl inoculum into the right rear thigh muscle.

For measurement of latent infection, mice were sacrificed 32 days post-challenge, and DRG from both right and left sides were removed, placed in DMEM/10% FBS, minced with scissors, and explanted onto sub-confluent Vero cell monolayers. Cultures were monitored daily (for 15 days) for plaque formation, indicating reactivation from latency.

Results

Figure 20:
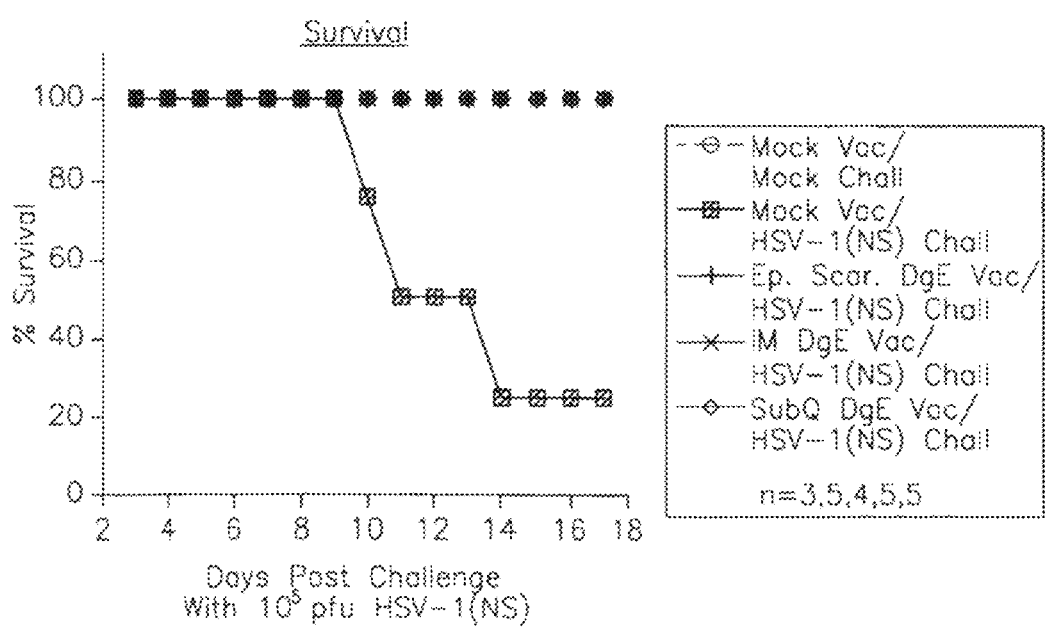
Figure 20:
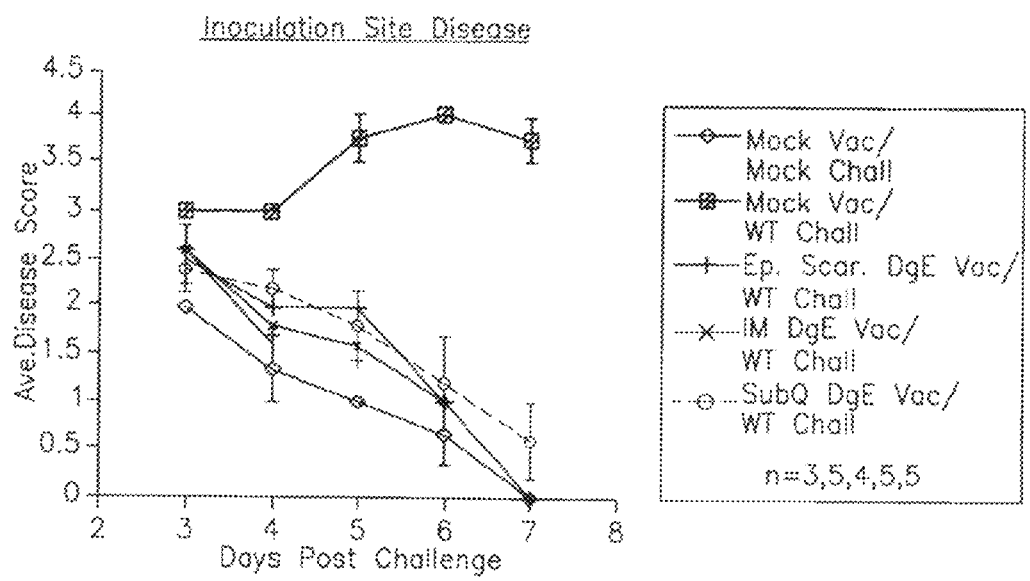
Figure 20:
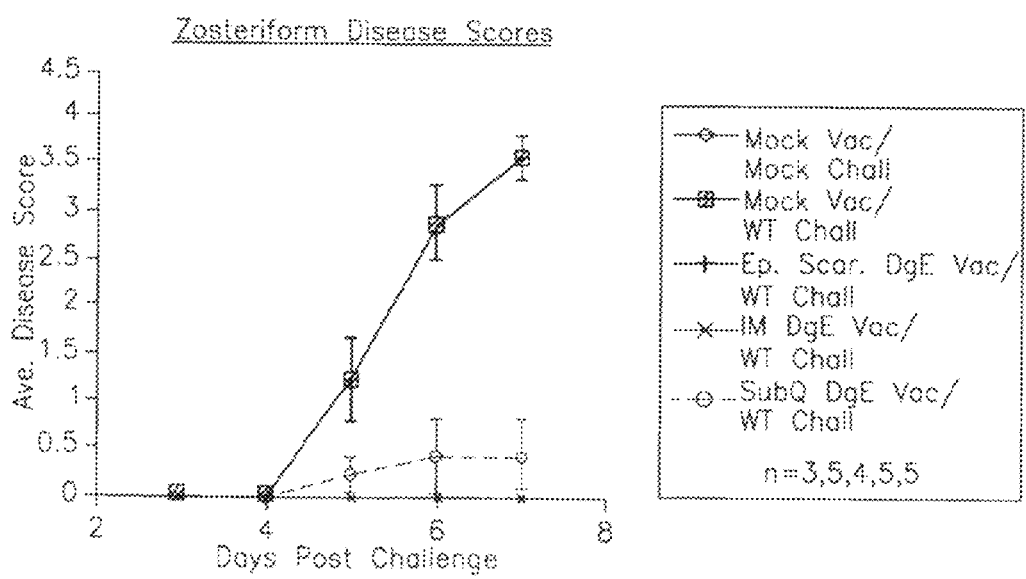

The efficacy of intramuscular and subcutaneous mutes of administration of the HSV-1ΔgE vaccine was compared to epidermal scarification used in previous Examples. All routes of vaccination were effective at protecting mice against death upon epidermal challenge with HSV-1(NS) (FIG. 20, top panel). Mice vaccinated by each of the three mutes exhibited inoculation site disease upon HSV-1(NS) challenge that was only slightly greater than mock-challenged mice (FIG. 20, bottom left panel). HSV-1ΔgE vaccination by epidermal scarification or intramuscular injection protected mice completely against zosteriform disease (FIG. 20, bottom right panel). Following challenge, ⅕ mice vaccinated by the subcutaneous mute had several discrete zosteriform lesions, which were not severe and resolved quickly (FIG. 20, bottom right panel). In addition, the ability of the vaccine to prevent latent infection was measured. HSV-1ΔgE vaccination by all mutes protected against the establishment of latency (Table 1). Mock-vaccinated mice showed 100% reactivation (Table 1; also see FIG. 18).

TABLE 1

HSV-1 vaccination by different routes protects against HSV latency.

| Vaccination Route | Reactivation from Latency |
| --- | --- |
| Mock | 1 of 1 |
| Epidermal Scarification | 0 of 4 |
| Intra-Muscular | 0 of 5 |
| Subcutaneous | 1 of 5 |

Thus, HSV-1ΔgE administered by epidermal, intramuscular or subcutaneous mutes each protects against acute disease, flares and latent disease by wild-type HSV challenge.

Example 10

Vaccination with HSV-1ΔgE by Epidermal Scarification, Subcutaneous Injection and Intramuscular Injection Induces Neutralizing Antibodies Materials and Experimental Methods Mice were vaccinated as described in the previous Example. On day 21, mice were bled through jugular veins. On day 28, the opposite flank (left side) of each mouse was shaved and denuded as before. Neutralization assays on serum samples were done by incubating 50 mcl serum dilution (1:10 to 1:320) with $10^2$ pfu HSV-1 (NS) in 5 mcl for 1 hour at 37° C., and then inoculating Vero cell monolayers.

Results

Figure 21:
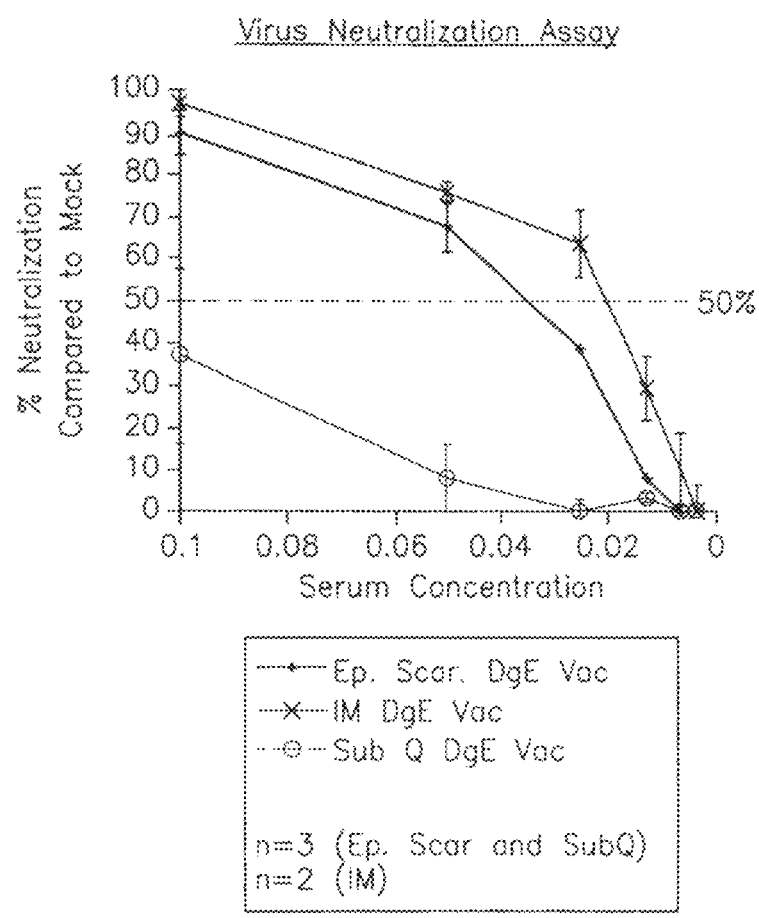

The efficacy of HSV-1ΔgE vaccination by the epidermal scarification, intramuscular, and subcutaneous routes of administration for induction of neutralizing antibodies were measured. HSV-1ΔgE vaccination of mice by all three routes induced neutralizing antibody formation; the epidermal scarification and intramuscular routes yielded significantly higher levels than subcutaneous vaccination (FIG. 21).

Example 11

Figure 22:
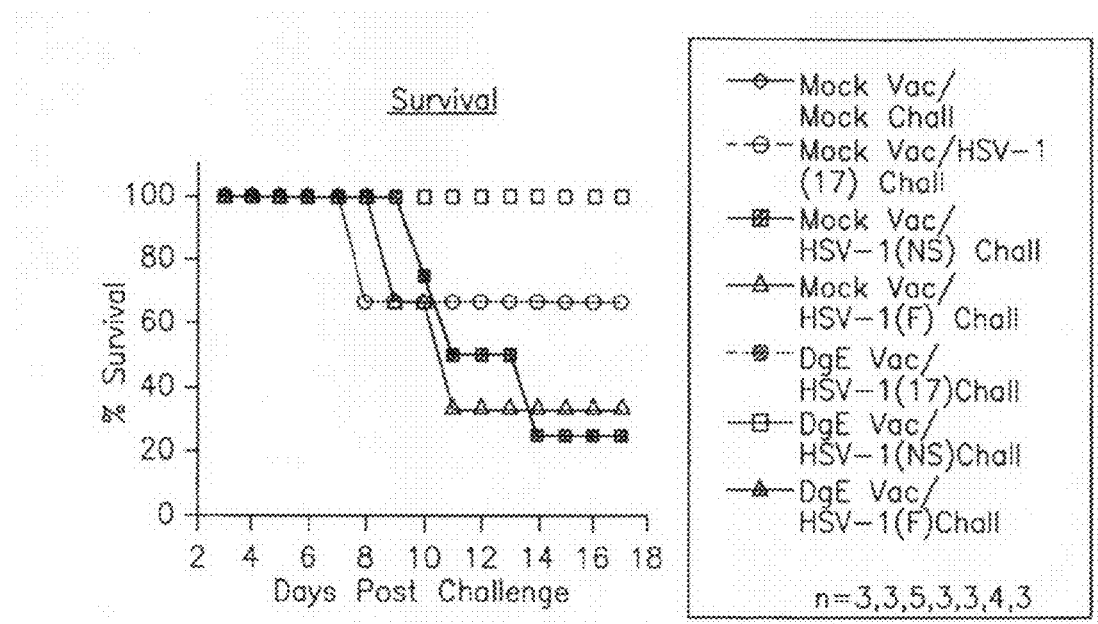
Figure 22:
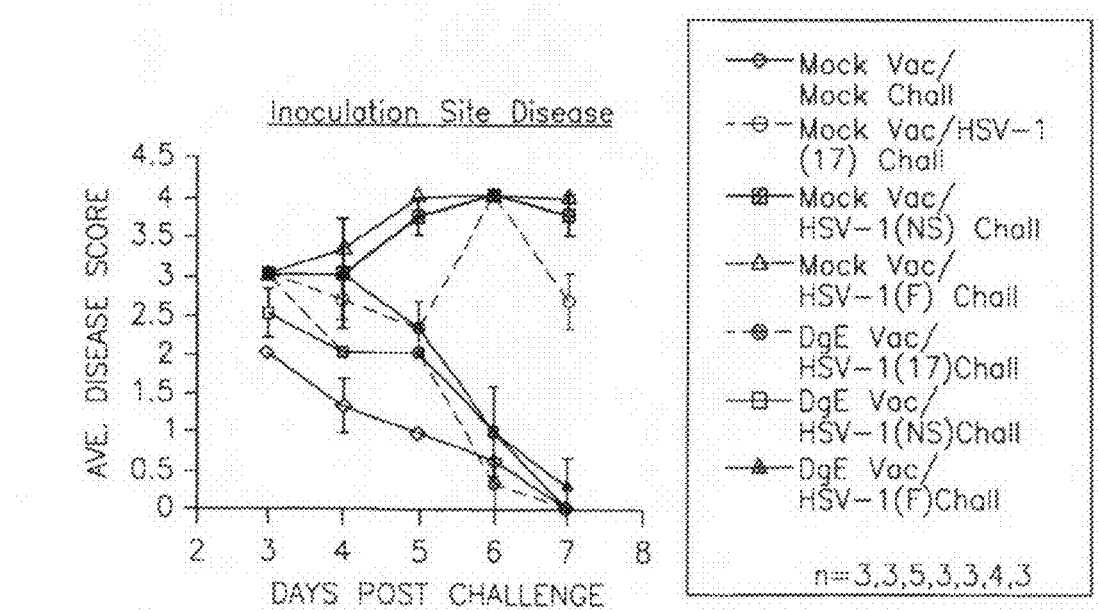
Figure 22:
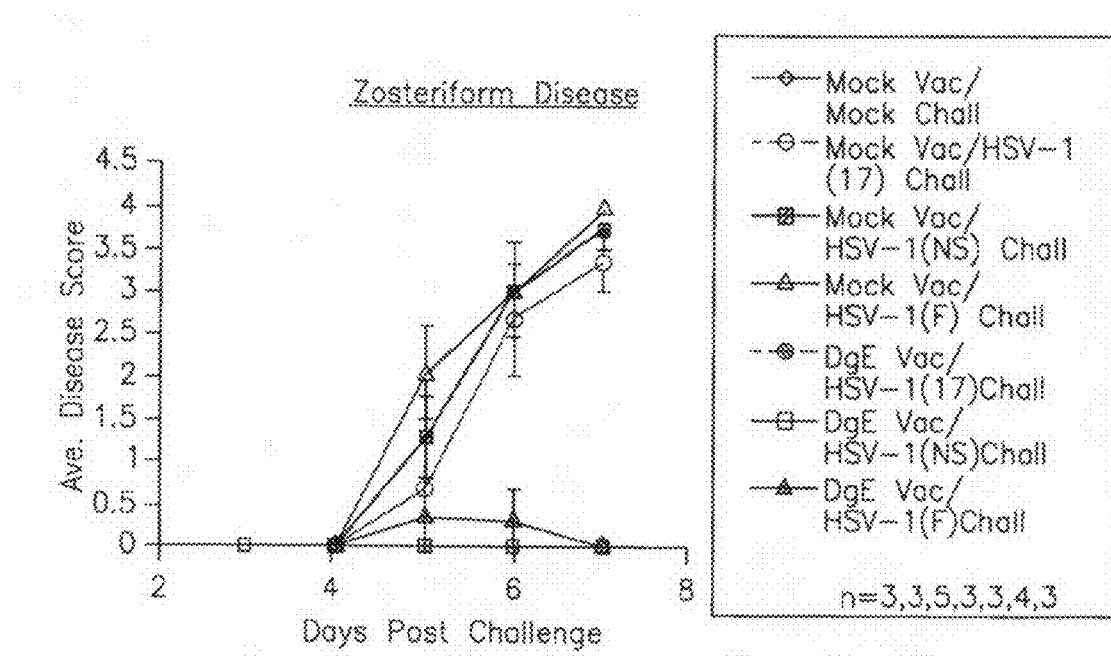

Vaccination with HSV-1ΔgE protects against flank Challenge with Various Heterologous HSV-1 Strains Ability of HSV-1ΔgE vaccination to protect against heterologous, higher virulence wild-type HSV-1 strains (F and 17) was measured; with vaccination and challenged performed as described for Example 7, except that challenge utilized various strains. HSV-1ΔgE vaccination protected mice completely from death upon epidermal challenge with HSV-1 (NS), HSV-1(F) and HSV-1(17) (FIG. 22, top panel). Vaccination also reduced inoculation site disease, although challenge with HSV-1(F) caused slightly more disease at the inoculation site than HSV-1(NS) or HSV-1(17) (FIG. 22, middle panel). Moreover, HSV-1ΔgE vaccination completely protected all mice challenged with HSV-1(NS) and HSV-1 (17) from zosteriform disease and ⅔ mice challenged with HSV-1(F); the other mouse challenged with HSV-1(F) had two small zosteriform lesions (FIG. 22, bottom panel). Thus, HSV-1ΔgE vaccination protects mice against various heterologous strains of HSV-1.

Example 12

Vaccination with HSV-1ΔgE Protects Against Flank Challenge with Doses up to $1 \times 10^7$ Pfu of HSV-1(NS)

Figure 23:
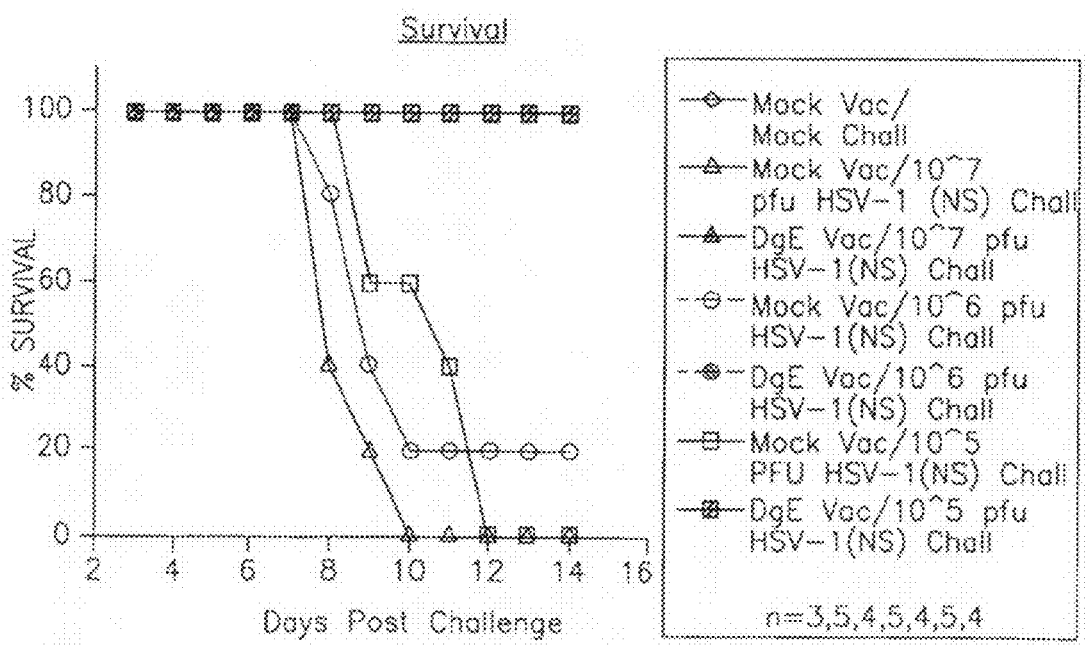
Figure 23:
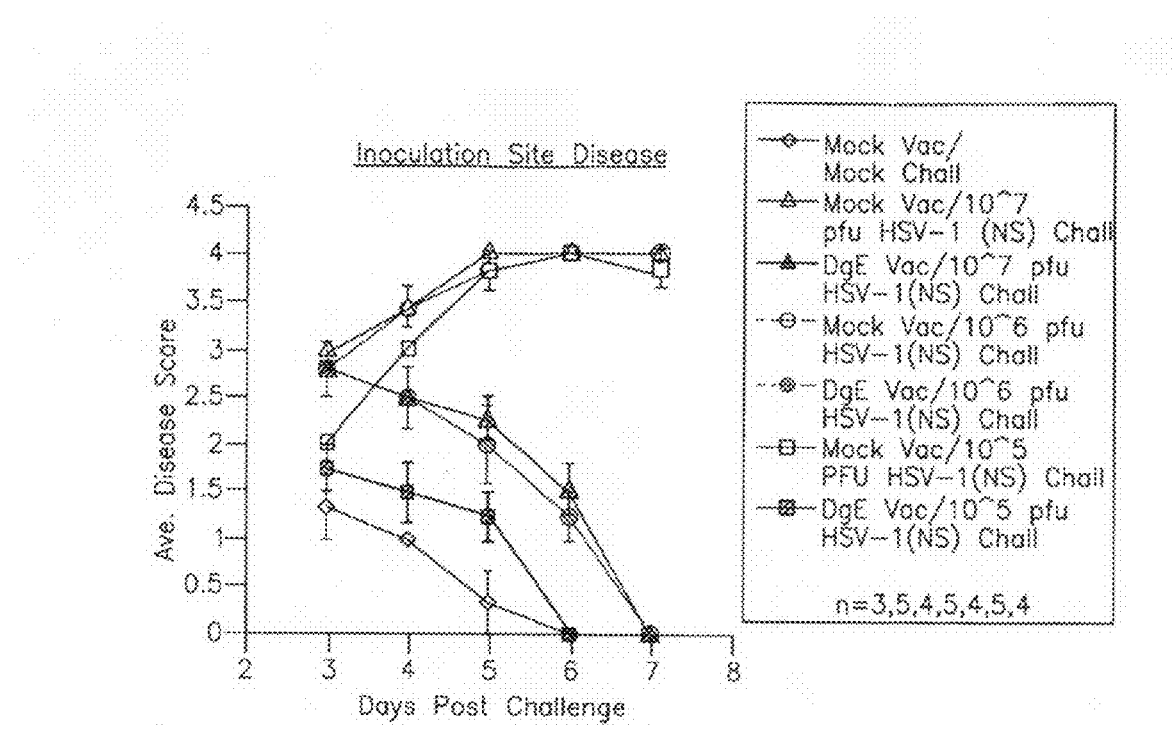
Figure 23:
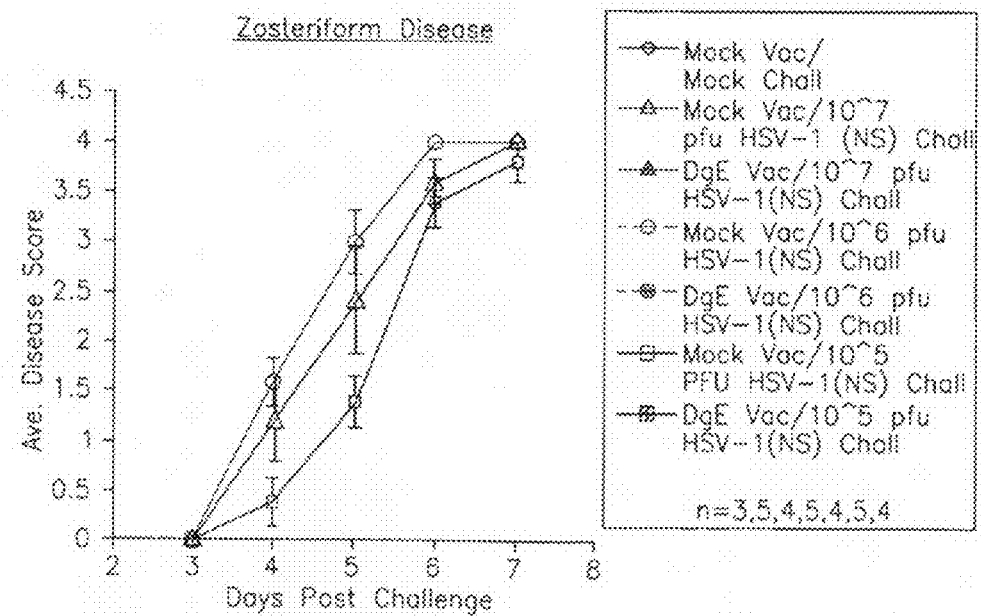

The ability of HSV-1Δvaccination to protect against higher doses of wild-type HSV-1 was measured; with vaccination and challenged performed as described for Example 7, except that challenge utilized higher doses of $10^5$, $10^6$ or $10^7$ pfu of HSV-1(NS). Vaccinated mice were all completely protected from death and zosteriform disease (FIG. 23, top and bottom panels). Vaccinated mice challenged with $10^5$ pfu HSV-1(NS) exhibited inoculation site disease that was slightly more severe than mock-challenged mice, indicating that most of the disease was caused by the scarification (needle scratch). Challenge of HSV-1ΔgE vaccinated mice with $10^6$ or $10^7$ pfu was associated with significantly reduced disease at the inoculation site, which healed rapidly compared with mock-vaccinated mice (middle panel).

Example 13

HSV-2$_{(gE\ NULL)}$ Does not Cause Disease

Materials and Experimental Methods

Cells and Viruses

Vero cells (ATCC CCL81) are cultured in Dulbecco's modified Eagle's medium containing heat-inactivated 10% newborn calf serum (Life Technologies, Gaithersburg, Md.) plus 50 micrograms (mcg) of penicillin/ml, 50 mcg/ml of streptomycin/ml, and 0.15 mcg/ml of Fungizone® (Life Technologies) at 37° C. and 5% $CO_2$. Clarified stocks of HSV-2 strains are prepared from infected Vero monolayers and stored at −80° C. until used. Titers of virus are determined by standard plaque assays.

Figure 24B:
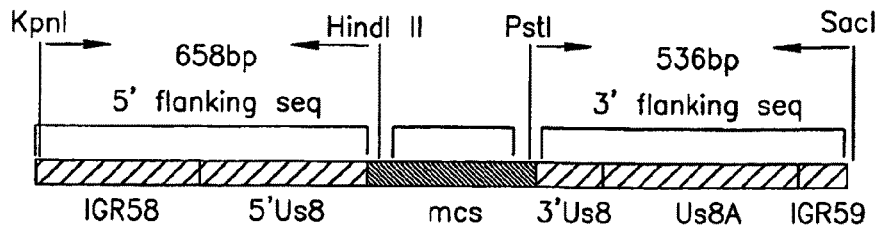

A deletion in base pairs (bp) 369-1479 of the 1635 bp HSV-2 (2.12) Us8 gene, encoding HSV-2 gE, was introduced as follows. Two PCR fragments from HSV-2(2.12), namely a 658 bp fragment corresponding to the region 5' of the intended deletion and a 536 bp fragment 3' of the intended deletion, were subcloned into the pBluescript SK+ multiple cloning site (MCS). The 5' flanking region was subcloned into the KpnI and HindIII sites of the pBluescript SK+ MCS, and the 3' flanking region was subcloned into the PstI and SacI sites of the MCS. This left a short stretch of the MCS between the 5' and 3' flanking regions that includes the EcoRI and EcoRV restriction sites and causes a frameshift such that only the first 123 amino acids of gE were expressed (FIG. 24B). The vector was co-transfected into Vero cells with HSV-2 (2.12) genomic DNA to allow for homologous recombination. The virion DNA purified from resulting plaques was screened by PCR to detect incorporation of the deletion.

Mouse Vaginal Model of HSV-2 Infection

Mice are treated with 2.0 mg of Depo-Provera (Upjohn, Kalamazoo, Mich.) subcutaneously in the scruff of the neck 7 and 1 day prior to viral inoculation to synchronize their estrus cycles and to increase their susceptibility to HSV-2 vaginal infection. HSV-2 virus ($10^4$ pfu) is instilled in the vaginal cavity following wet and then dry vaginal swabbing with a calcium alginate swab (Fisher Scientific, Pittsburgh, Pa.). Animals are assessed daily for symptomatic disease (as indicated by hair loss and erythema near the vagina) through 14 days post-inoculation (p.i.). Survival is followed through 21 days p.i. As an additional indicator of infection, vaginal swabs are collected and tested for viral content on Vero cells.

Results gE null HSV-2 virus is constructed from strain HG52, using a similar strategy as that used for HSV-1 (Example 1). The HSV-1 (NS) gE (Examples 1-5) and HSV-2 (HG52) gE sequences are 72% identical and 79% similar (positive) (FIG. 24A). In addition, an HSV-$2_{(Rescue\ gE\ null)}$ strain is constructed.

To test whether the HSV-$2_{(gE\ null)}$ strain causes disease, a dose of $10^4$ pfu (lethal in the case of wt virus) of wt HSV-2 and the HSV-$2_{(gE\ null)}$ strain are administered to separate groups of mice. While the mice receiving the wt and HSV-$2_{(Rescue\ gE\ null)}$ virus are expected to die, those receiving the HSV-$2_{(gE\ null)}$ strain are expected to survive, and are not expected to exhibit significant signs of disease.

Example 14

HSV-$2_{(gE\ NULL)}$ Vaccination is Protective Against Wild-Type HSV-2 Infection Materials and Experimental Methods Mice are vaccinated with HSV-$2_{(gE\ null)}$ or mock-vaccinated as described in the previous Example, and are challenged 28 days later with a lethal dose of WT HSV-2. HSV-$2_{(gE\ null)}$-vaccinated mice are expected to be protected from the lethal challenge, whereas mock-vaccinated mice are expected to succumb to the infection. Additionally, HSV-$2_{(gE\ null)}$ vaccination is expected to substantially decrease or eliminate primary (inoculation site) disease after challenge with wt HSV-2. Unlike the hair loss and erythema expected near the vagina in mock-vaccinated mice, no zosteriform disease is expected to be observed in vaccinated mice. Confirming this observation, immunohistochemistry of equivalent skin samples is expected to demonstrate substantially reduced antigen levels in vaccinated mice several days post-challenge. Histological analyses are expected to reveal that vaccinated mice exhibit significant infiltration of immune cells.

In additional experiments, the HSV-$2_{(gE\ null)}$ vaccine is tested in the mouse flank model (Examples 4-5), and is expected to be protective against HSV-2 infection.

Example 15

Efficacy of HSV-$2_{(gE\ NULL)}$ Vaccination Against Existing HSV-2 Genital Infection in a Guinea Pig Model Materials and Experimental Methods Guinea Pig Model of Genital Herpes On the day of inoculation, vaginal closure membranes are ruptured with a pre-moistened calcium alginate swab. Vaginal vault is swabbed with a dry calcium alginate swab, and $10^{5.7}$ pfu of HSV-2 is instilled into the vaginal vault with a syringe and a 20-gauge plastic catheter. This dose is sublethal, while providing infection of nearly every inoculated animal. During acute genital infection, animals are evaluated daily through day 14 p.i. for genital skin disease and urinary retention. Disease is quantified by a skin lesion scoring system ranging from 0 (no disease) to 4 (severe disease characterized by large ulcers with maceration). Following acute disease, animals are distributed to produce statistically similar groups based upon disease severity. Daily scoring of each animal proceeds from day 21-56 p.i. to establish frequency of external recurrent herpetic lesions.

Viral Shedding Detection

Guinea pigs spontaneously shed HSV-2 from the vaginal cavity even in the absence of signs of disease. Viral DNA can be detected in 10 to 20% of the vaginal swabs from latently infected guinea pigs, allowing for the study of viral shedding frequencies and comparisons of the magnitudes. Vaginal cavities are swabbed daily with a calcium alginate-tipped swab from days 22-43 p.i. DNA is extracted from each swab sample using the QIAmp® DNA extraction system (Qiagen, Inc, Chatsworth, Calif.), including mock swab blanks as monitors for sample contamination, and subjected to quantitative PCR for HSV-2 DNA, using primers targeting the DNA polymerase gene. A separate reaction is performed for each of the specimens to address template quality and quantity, using a second set of primers to amplify the single-copy guinea pig albumin gene. The resulting 498-bp amplimer is utilized for normalization of DNA concentration and a more quantitative estimate of the HSV-2 burden in each specimen. Positive specimens are compared to amplification of a series of 10-fold serial dilutions of established genomic equivalents using MS HSV-2 stocks. Reactions are run in a GeneAmp® PCR System 9600 (Perkin-Elmer Corp, Norwalk, Conn.) beginning with a "hot start" at 95° C. for 2 min; then 35 cycles of denaturation at 95° C. for 1 min, annealing for 1 min at 65° C., and 72° C. extension for 1 min 30 s; and a final 7-min extension at 72° C. Amplification products of each sample, positive and negative controls, and the series of known standards are detected by Southern blotting. HSV-2 burdens are extrapolated from the linear relationship established from band density of a dilution series of known genomic equivalents amplified in parallel to the samples.

Determination of HSV-2 DNA Copy Numbers in Guinea Pig Dorsal Root Ganglia.

Sacral dorsal root ganglia (6-8 per animal) are dissected and weighed, viral DNA is extracted by using a QIAamp® DNA minikit (QIAGEN), and real-time PCR is performed. A standard curve is constructed for each experiment, using purified plasmid containing HSV-2 gD gene sequences. Data are normalized to probes specific for guinea pig lactalbumin DNA.

Results

The guinea pig model is utilized to evaluate the efficacy of ISS against recurrent herpetic disease. This model provides a naturally occurring recurrent disease similar to that seen in human HSV-2 infections, and latently infected guinea pigs shed virus vaginally at a frequency similar to that observed in humans.

Guinea pigs are vaccinated with HSV-$2_{(gE\ null)}$ r mock-vaccinated and are challenged 28 days later with $10^{5.7}$ pfu of HSV-2. HSV-$2_{(gE\ null)}$ vaccination is expected to significantly reduce the frequency of genital lesion development compared to mock-vaccinated animals and reduce the number of animals that experience any recurrences. In addition, HSV-2$_{(gE\ null)}$ vaccination is expected to significantly reduce the magnitude of viral shedding.

To test the effect of HSV-2$_{(gE\ null)}$ vaccination on the establishment of latent HSV-2 infection, accumulation of wt HSV-2 viral genomes in guinea pig DRG is evaluated. HSV-2$_{(gE\ null)}$ vaccination is expected to significantly reduce the number of viral genomes in the DRG.

This and the previous Example are expected to provide additional evidence that HSV-2$_{(gE\ null)}$ vaccines are efficacious in protecting subjects against HSV-2 infection and subsequent genital reactivation.

Example 16

Figure 25:
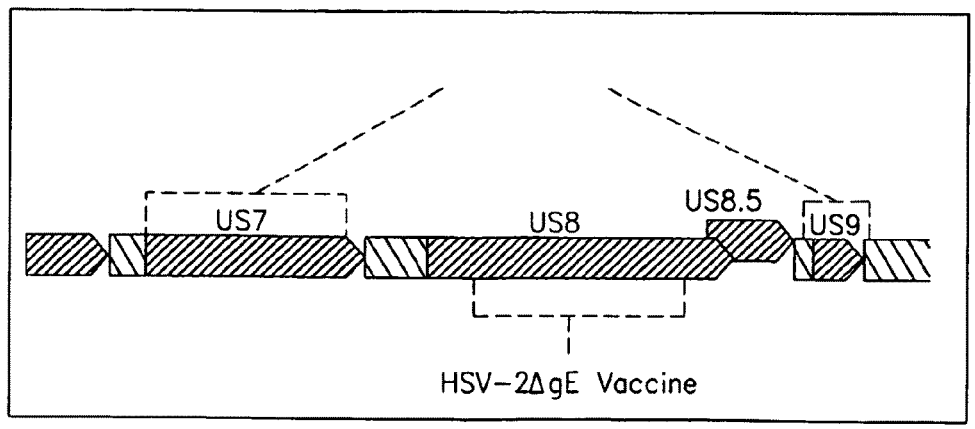

Introduction of Additional Deletions to the Us Region in Order to Further Impair the Anterograde Spread of the ΔgE-2 Vaccine Strain In order to further attenuate the ΔgE-2 vaccine strain, additional deletions are introduced into Us7 and Us9, encoding the gI and Us9 proteins (FIG. 25), using a similar approach to that used to construct the HSV-2 Us8 deletion. A cloning vector that contains two 500-1000 base pair flanking regions, each homologous to either the DNA sequence 5' or 3' of the intended deletion, is constructed. The DNA for these two regions is obtained by PCR of HSV-2(2.12) genomic DNA. The cloning vector is co-transfected with HSV-2 genomic DNA, so that the deletions are incorporated into the viral DNA by homologous recombination. The resulting plaques are screened for the correct Us deletion by PCR.

Example 17

Identification of Additional Mutations that Impair Anterograde Spread of the ΔgE-2 Vaccine Strain RNAi gene silencing methodology is utilized to identify genes other than gE, Us7 and Us9 that are involved in virus spread. RNAi technology uses approximately 20-22 base-pair double-stranded RNA fragments with sequences identical to the viral gene targeted for silencing. To target sequences on viral genes of HSV-1 or HSV-2, small RNA double-stranded fragments identical in sequence to the viral RNA are synthesized using standard techniques known in the art, and are introduced by transfection technology into cells that are then infected with HSV-1 or HSV-2 wild-type or mutant virus. Spread of defective virus is detected by screening for small plaques in human epidermal keratinocytes (HaCaT) cells (Collins W J et al. Herpes simplex virus gE/gI expressed in epithelial cells interferes with cell-to-cell spread. J Virol. 2003 February; 77(4):2686-95). The genes targeted by the RNAi fragments that induce small plaques are used in gene deletion studies. Inactivating mutations are then introduced into the gene or genes identified by the above RNAi screening method to create mutant viruses. Spread properties of mutant viruses are evaluated in vitro using rat superior cervical ganglion cell neuron cultures (Wang F, Tang W, McGraw H M, Bennett J, Enquist L W, and Friedman H M. J. Virol 79:13362-72, 2005) and the mouse retina eye infection model (Wang F, Tang W, McGraw H M, Bennett J, Enquist L W, Friedman H M. J. Virol 79:13362-72, 2005). The viral mutant strains identified that modify spread in vitro or in vivo are introduced into strains containing deletions of gE, Us7 or Us9 to develop strains containing deletions in multiple genes to identify the optimum combination of mutations that causes little or no disease when inoculated into laboratory animals, that results in low levels or no viral DNA in DRG, and that provides maximum protection against disease and establishment of viral latency when challenged by infection with wild type HSV-1 or HSV-2.

In other experiments, efforts are focused on virion membrane proteins, e.g. glycoproteins J, G, K, and M. Membrane glycoproteins required for virus entry, e.g. glycoproteins B, D, H and L, are excluded. These virion membrane proteins are analyzed as described in the previous paragraph.

Example 18

Characterization and Stability of HSV gD Mutant

Materials and Experimental Methods (Examples 18-23)

Virus Strains

Wild-type HSV-1 strain KOS was used to prepare gD mutants. To construct HSV-1$_{(gD\ null)}$, plasmid pSC594 was constructed by inserting A3C (alanine to cysteine) and Y38C (tyrosine to cysteine) mutations into plasmid pRM416 which contains the KOS gD open reading frame flanked by 474 base pairs 5' and 985 base pairs 3' of the open reading frame. HSV-1 gD-mull DNA and pSC594 DNA were co-transfected into VD60 cells. Recombinant virus was screened by replication in Vero cells and then plaque-purified. After each plaque purification, 600 base pairs were amplified by PCR at the 5' end of the gD gene that included the sites of the mutations. The amplified gD fragments were screened by restriction enzyme mapping. Introduction of a new SspI site confirmed the presence of the A3C mutation and the loss of an RsaI site confirmed the presence of the Y38C mutation. Following further plaque purification, DNA sequencing to confirm the presence of the mutations. The clones were grown to high titer on Vero cells, purified on a 10% to 60% sucrose gradient, and subjected to a final DNA sequence analysis and restriction mapping, which revealed that only the A3C mutation remained. The KOS-gDA3C was further purified on a sucrose gradient and the entire gD gene was sequenced to confirm the presence of the A3C mutation and the absence of additional unintended mutations.

Rescued KOS-gDA3C virus, referred to as rKOS-gDA3C, was generated by co-transfection of Vero cells with KOS-gDA3C and pRM416 DNA.

Virus stocks were grown in Dulbecco's minimum essential medium (DMEM), supplemented with 10% fetal calf serum (FCS). B78-H1 cells, mouse melanoma cells that are non-permissive for HSV-1 entry, were grown in DMEM with 5% FCS. B78-H1-A10 cells (A10) and B78-H1-C10 cells (C10) stably express HVEM and nectin-1, respectively, and were grown in DMEM containing 5% FCS and 500 µg/ml of G418. The gD-null virus was propagated in Vero cells stably transfected with gD DNA (VD60 cells). HSV-1 strain NS, a low-passage clinical isolate, was used for challenge studies in mice. Viruses were grown in Vero cells, unless otherwise noted, purified on sucrose gradients and stored at −80° C.

Mouse Flank Infection Protocol

All experimental protocols were approved by the University of Pennsylvania animal and laboratory resources IACUC committee. Five-six-week-old Balb/c mice (Charles River were allowed to acclimate to the biosafety level 2 animal facility with constant temperature and photoperiod (12 hours of light, 12 hours of darkness) for 1 week. Mice were shaved and depilated with depilatory cream with calcium hydroxide and potassium thyoglycolate as active ingredients (NAIR™) along the right flank (for vaccination) or the left flank (for challenge), then washed with warm water. The next day, mice were anesthetized via intraperitoneal injection of 75 mcL of 14.3 mg/ml ketamine and 1.8 mg/ml xylazine in PBS, then infected by making 60 superficial scratches in a 1 cm² area of the flank, 1 cm dorsal to the spine, with a 30-gauge needle through a 10 mcL droplet containing $5 \times 10^5$ pfu HSV Mice were observed at 24-hour intervals starting at day 3 post-inoculation to record the appearance and severity of skin lesions and illness. Scores at the inoculation site ranged from 0 to 5 and at the zosteriform site from 0 to 10. One point was assigned per vesicle or if lesions were confluent multiple points were assigned based on the size of the confluent lesions.

Entry Assay

KOS-gDA3C, rKOS-gDA3C or KOS (400 pfu) was incubated for one hour at 4° C. with B78-H1, A10, C10 or Vero cells. Cells were warmed to 37° C. for 0, 10, 30, 60 or 120 minutes followed by washing to remove unbound virus and exposed to a citrate buffer pH 3.0 wash for 1 minute to inactivate virus that had bound but had not entered cells. After an additional wash, cells were overlaid with 0.6% low-melt agar in DMEM, and plaques were visualized and counted after 68 hours.

Single-Step and Multi-Step Growth Curves

Single-step growth curves were performed on B78-H1, A10 and C10 cells inoculated with KOS, KOS-gDA3C or rKOS-gDA3C virus at an MOI of 3. After one hour at 37° C., cells were treated with citrate buffer pH 3.0 for one minute, and cells and supernatant fluids were collected immediately (time 0) or at 2, 4, 8, 10, 12, 20 and 24 hours. Samples were freeze-thawed once, sonicated three times each for 10 seconds and titered on Vero cells. Multi-step growth curves were performed in a similar fashion, except infection was performed at an MOI of 0.01 and titers measured at 24, 48 and 72 hours.

Real-Time Quantitative PCR for Viral DNA in Dorsal Root Ganglia (DRG)

DRG nearest the site of inoculation were harvested and DNA was isolated using the Qia Amp-mini DNA kit (Qiagen). The Us9 gene was amplified to quantify viral genome copy number in DRG. The PCR reaction was performed in a 50 mcl volume with a minimum of 200 ng of DNA from DRG. Fifty pmol of forward 5' cgacgccttaataccgactgtt (SEQ ID NO: 8) and reverse 5' acagcgcgatccgacatgtc (SEQ ID NO: 9) primers and 15 pmol of Taqman probe 5'tcgttggccgc-ctcgtcttcgct (SEQ ID NO: 10) were added. One unit of Ampli Taq Gold (Applied Bioscience) per 50 mcl reaction was added. Real time PCR amplification was performed on an ABI Prism7700 Sequence Detector (Applied Biosystems). A standard curve was generated from purified HSV-1 (NS) DNA. Mouse adipsin, a cellular housekeeping gene was also amplified from DRG DNA under identical conditions. The primers used for amplification were forward 5'gatgcagtc-gaaggtgtggtta (SEQ ID NO: 11) and reverse 5'cggtaggatga-cactcgggtat (SEQ ID NO: 12), while Taqman probe 5'tctcgcgtctgtggcaatggc (SEQ ID NO: 13) was used for detection. The viral DNA copies were then normalized based on the murine adipsin copy number.

Results

Figure 26A:
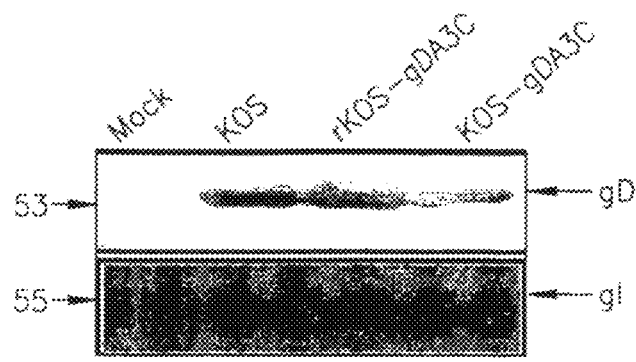
Figure 26B:
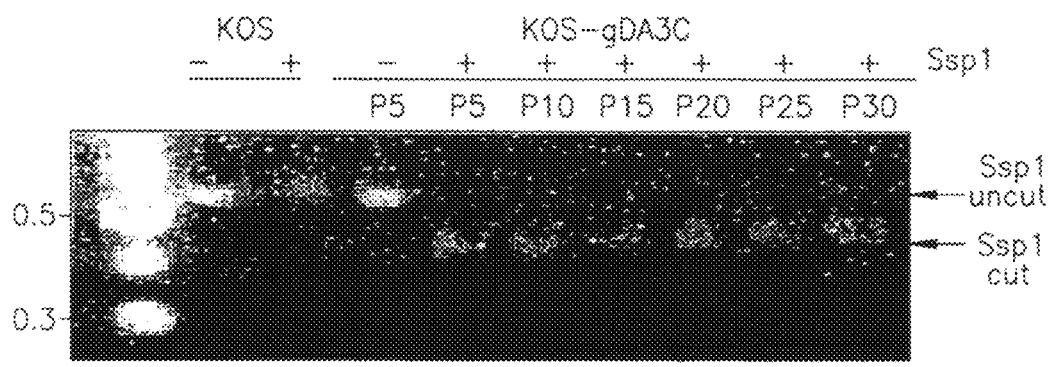

Since the gD transcript is co-terminal 3' with gI and gJ, the molecular mass of gD and gI was evaluated by western blots of cells infected with WT, rKOS-gDA3C, or KOS-gDA3C virus. The size of the proteins was similar for the three viruses (FIG. 26A), while DNA sequencing confirmed the integrity of the gJ gene in KOS-gDA3C (result not shown). The stability of the gDA3C mutation was confirmed by restriction digestion using SspI of PCR-amplified DNA fragments to confirm the presence of the cysteine residue at position 3. The Ssp1 site was maintained through 30 passages, suggesting that the change of alanine to cysteine at residue 3 was stable (FIG. 26B). This was confirmed by DNA sequence analysis after every five passages.

Figure 26C:
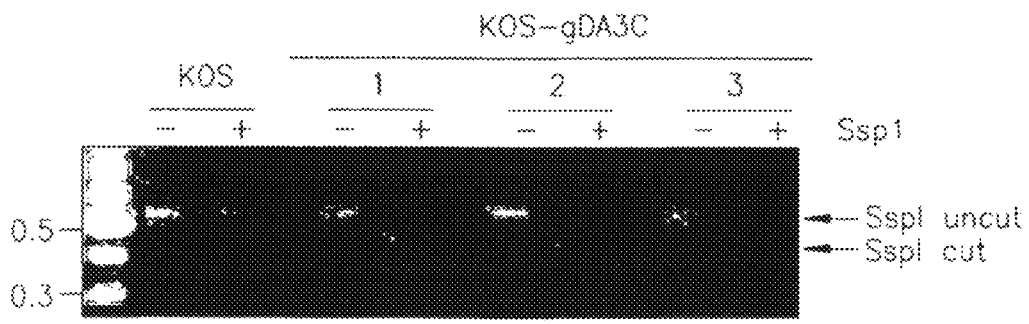

Mice were scratch-inoculated on the flank with KOS-gDA3C, and DRG harvested five days post-infection to confirm the stability of the gDA3C mutation in vivo. Virus was isolated from three individual plaques. All three isolates retained the Ssp1 site (FIG. 26C), suggesting that the cysteine residue at amino acid 3 was maintained, which was confirmed by DNA sequencing.

Example 19

HSV gD Mutant as an Entry-Impaired Live Virus Vaccine

Figure 27:
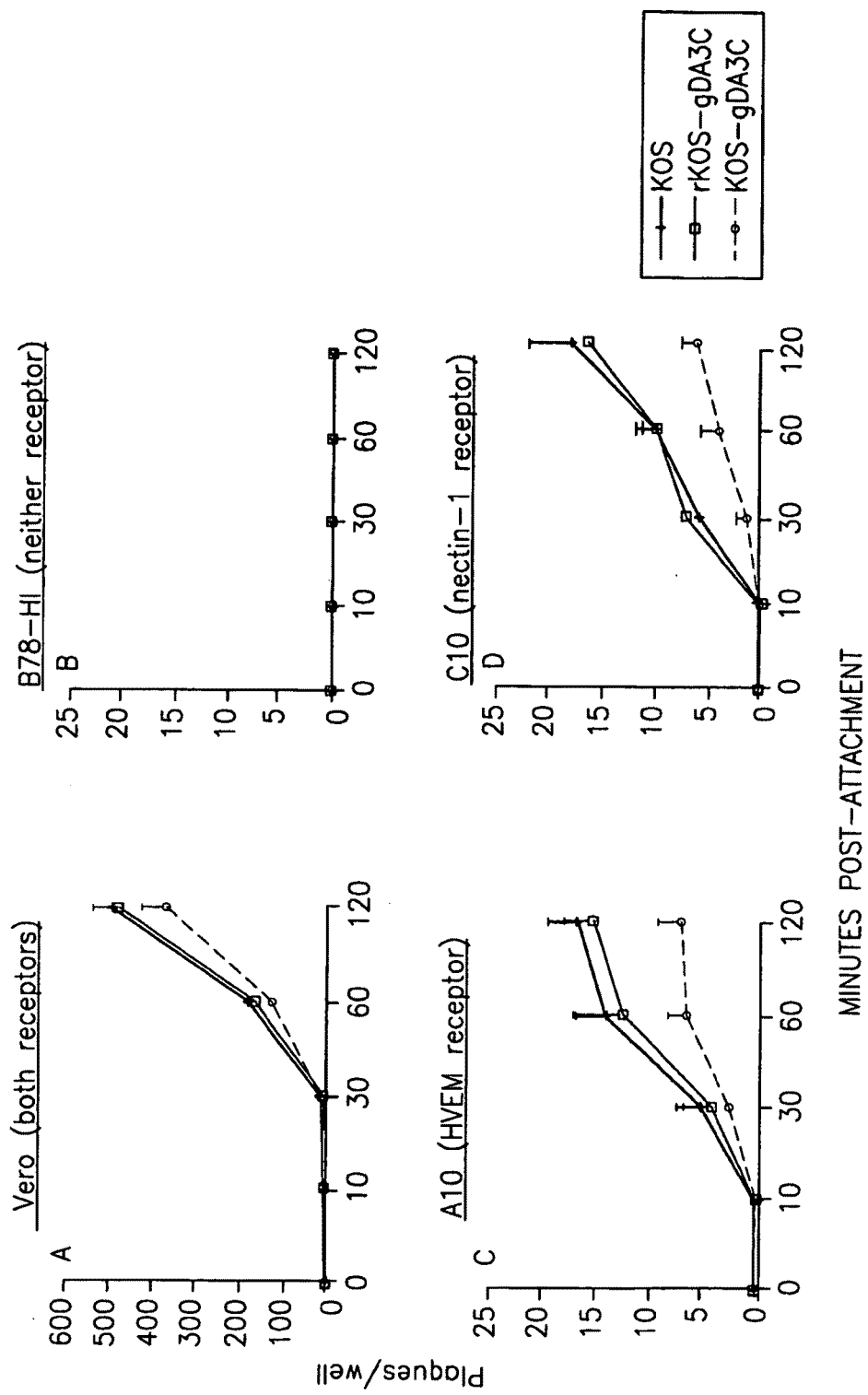

The entry of KOS, rKOS-gDA3C, and KOS-gDA3C into cells that express HVEM (A10), nectin-1 (C10), both (Vero), or neither receptor (B78-H1) was evaluated. Entry of the three viruses into Vero cells was comparable (FIG. 27A), while each virus failed to enter B78-H1 cells (FIG. 27B). Entry of KOS-gDA3C into A10 cells was reduced by approximately 50% compared with KOS or rKOS-gDA3C (FIG. 27C), and entry into C10 cells was reduced by approximately 70% (FIG. 27D).

These findings show that the gDA3C mutation reduces entry mediated by both HVEM and nectin-1 receptors.

Example 20

Growth Curves of HSV gD Mutant Virus

Virus replication was examined by performing single-step growth curve at an MOI of 3. KOS, rKOS-gDA3C and KOS-gDA3C failed to infect 1378-H1 cells (results not shown). Replication of the three viruses was comparable in MO cells (FIG. 28A) and C10 cells (FIG. 28B), except that the titers of KOS-gDA3C were reduced at time 0 (at the end of the one-hour adsorption period), which reflects the entry defect seen in Example 19.

Figure 28:
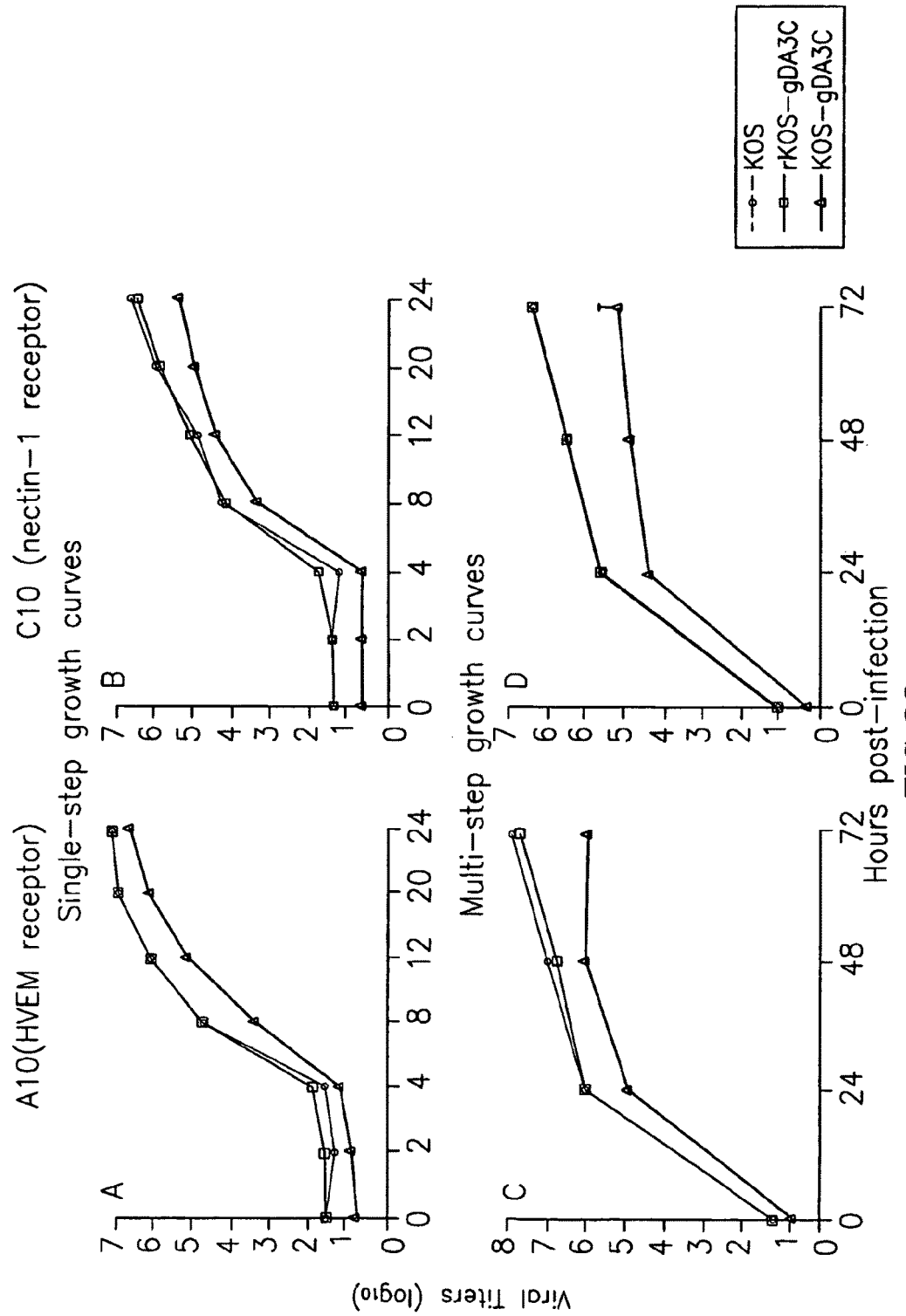

Multi-step growth curves were performed by infecting the cells at an MOI of 0.01 to allow multiple cycles of virus replication. Compared with KOS and rKOS-gDA3C, peak titers of KOS-gDA3C were reduced at 72 hours by approximately 1.5 log 10 in A10 cells (FIG. 28C) and 2 log 10 in C10 cells (FIG. 28D).

Example 21

HSV gD Mutant has Reduced Virulence

Figure 29:
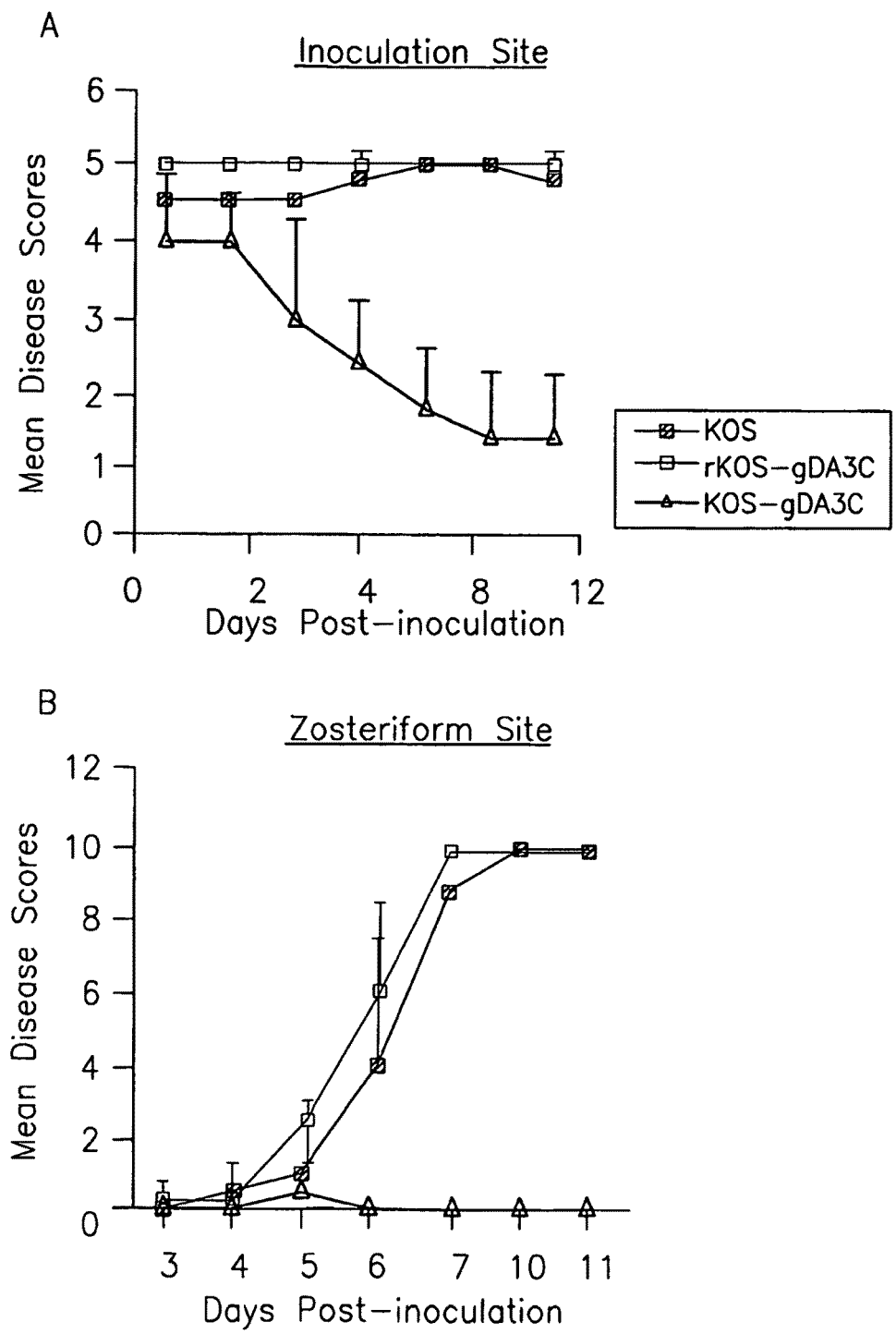
Figure 29:
Figure 29:
Figure 29:
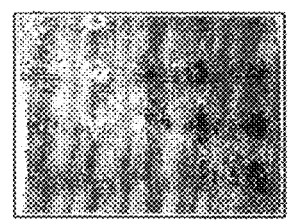
Figure 30:
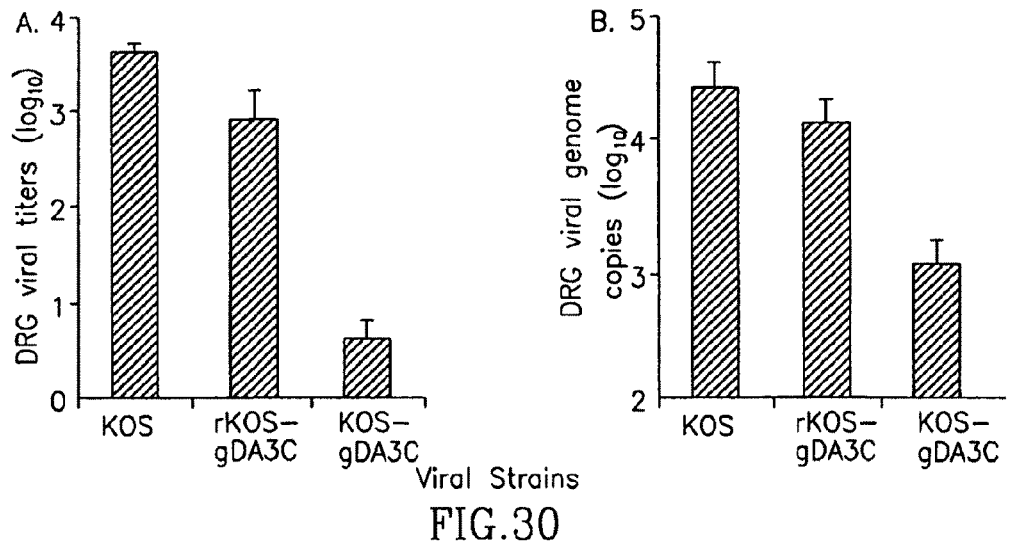
Figure 31:
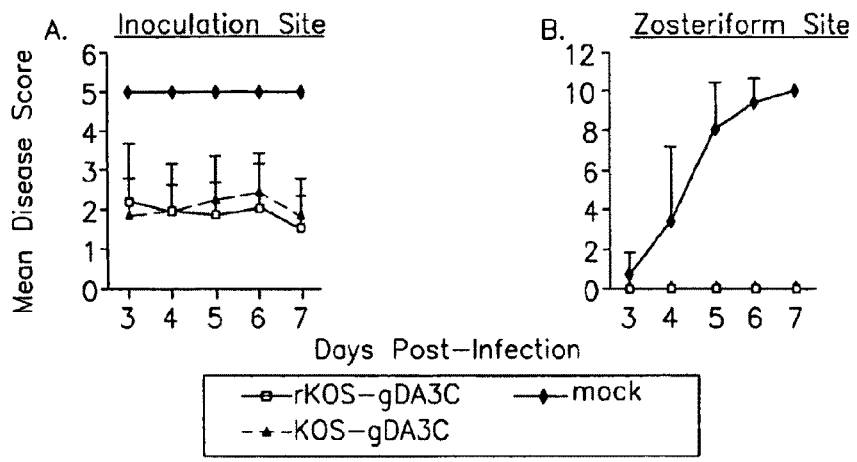
Figure 31:
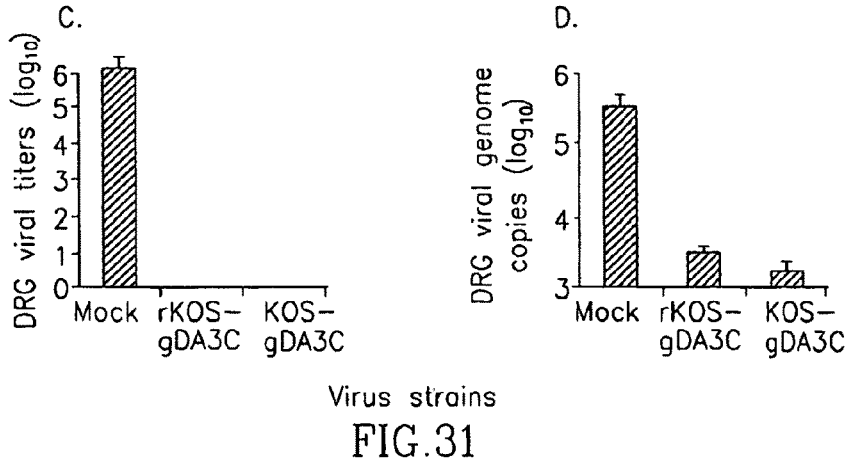
Figure 32:
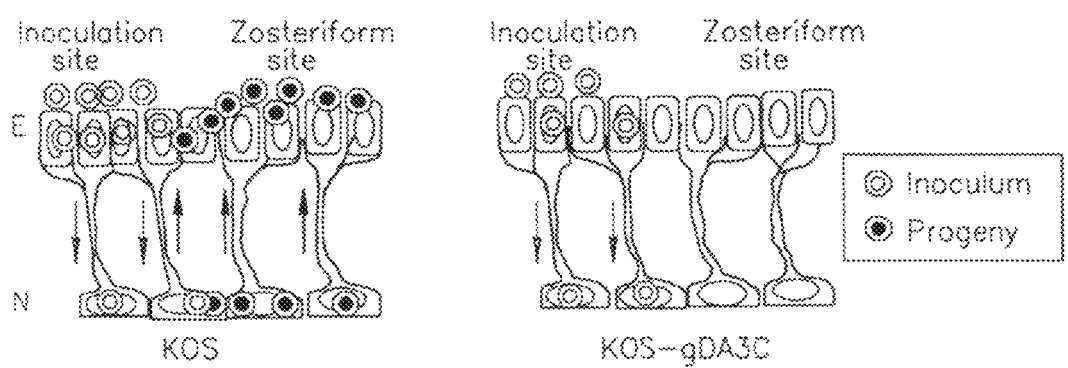

The virulence of the KOS-gDA3C mutant was evaluated in the mouse flank model. Mice were infected with $5 \times 10^5$ PFU of KOS, rKOS-gDA3C, or KOS-gDA3C and animals scored for disease at the inoculation and zosteriform sites. Mice infected with KOS-gDA3C had less severe disease at the inoculation site (FIG. 29A) and almost no zosteriform disease with only one of 30 mice developing 3 lesions on day 5 (FIG. 29B). Photographs of the zosteriform site disease are shown on day 10 (FIG. 29C).

These findings show that infection with the gD mutant herpes virus causes minimal disease.

Example 22

HSV gD has Reduced Ability to Reach DRG

Mice were inoculated with $5\times10^5$ PFU of KOS, rKOS-gDA3C, or KOS-gDA3C and at 5 days post-infection, the DRG were harvested to measure viral titers (FIG. 30A) and viral genome copy number (FIG. 30B), which were reduced for KOS-gDA3C compared with KOS or rKOS-gDA3C.

These findings show that the gD mutant herpes virus is defective in reaching the DRG.

Example 23

HSV gD Mutant as an Attentuated Live Virus Vaccine

Mice were mock-infected or infected with rKOS-gDA3C or KOS-gDA3C and allowed to recover. Although rKOS-gDA3C produced extensive disease, all animals survived, as did all mice infected with KOS. Thirty days later, mice previously infected with KOS-gDA3C or rKOS-gDA3C were challenged on the opposite flank with HSV-1 strain NS at 106 PFU (approximately 20 LD50). The challenge virus caused extensive disease at the inoculation (FIG. 31A) and zosteriform (FIG. 31B) sites in the mock group. KOS-gDA3C and rKOS-gDA3C protected against disease at the inoculation site and both viruses totally prevented zosteriform disease. None of the rKOS-gDA3C or KOS-gDA3C infected mice died after the NS strain challenge, while 100% of the mock-infected mice died (result not shown).

These findings show that KOS-gDA3C provided protection against challenge that was comparable to protection provided by the more virulent rKOS-gDA3C.

The ability of a prior infection with KOS-gDA3C to prevent the WT virus from reaching the DRG was evaluated. Mice were mock-infected or infected in the flank with $5\times10^5$ pfu of rKOS-gDA3C or KOS-gDA3C. Thirty days later, mice were challenged with $10^6$ pfu of NS on the opposite flank. DRG that innervate the challenge site were harvested five days post-challenge. NS viral titers were approximately 6 log 10 in DRG of mice that were previously mock infected, while no virus was recovered from DRG of mice previously infected with rKOS-gDA3C or KOS-gDA3C (FIG. 31C).

Quantitative PCR was performed on the DRG at five days post-challenge. Approximately 5.8 log 10 HSV-1 genome copies were detected in DRG of previously mock-infected mice compared with 3.4 or 3.2 log 10 DNA copies in mice previously infected with rKOS-gDA3C or KOS-gDA3C, respectively (FIG. 31D).

These findings show that KOS-gDA3C is attenuated in causing skin lesions at the inoculation and zosteriform sites and in infecting DRG, yet it is as effective as rKOS-gDA3C in protecting mice against WT HSV-1 challenge.

These examples suggest that an HSV strain with a mutation in gD may be used as an attenuated live HSV vaccine. FIG. 32 shows a model in which at each step of the virus life cycle, less KOS-gDA3C is produced because of the defect in virus entry. These steps include the amount of virus produced in epidermal cells (labeled E), in DRG nuclei (labeled N), and that return to the skin at the zosteriform site.

In one embodiment, the examples of the present invention provide experimental support for a method of vaccinating against HSV infection by contacting the subject with a mutant strain of HSV, containing one or more inactivating mutations.

What is claimed is:

1. An immunogenic composition comprising a mutant Herpes Simplex Virus type 2 (HSV-2) consisting of a single inactivating mutation in the Us8 gene, wherein said inactivating mutation is a deletion of base pairs (bp) 369-1479 of SEQ ID NO: 7, wherein said immunogenic composition induces an anti-HSV immune response in a subject.

2. A method of treating, reducing the pathogenesis of, or ameliorating the primary or secondary symptoms of a Herpes Simplex Virus (HSV) infection in a subject, comprising the step of inoculating said subject with a composition comprising the mutant HSV-2 of claim 1.

3. The method of claim 2, wherein said HSV infection is an HSV-1 infection or an HSV-2 infection.

4. The method of claim 2, wherein the neuronal viral spread of said mutant strain is impeded.

5. The method of claim 2, wherein said mutant strain is replication-competent in the skin tissue of said subject.

6. The method of claim 2, wherein said HSV infection is a genital HSV infection, HSV encephalitis, an HSV ocular infection, HSV labialis, or a combination thereof.

7. The method of claim 2, wherein said subject is infected by or is at risk for infection by HSV.

8. The method of claim 2, wherein said treating, reducing the pathogenesis of, or ameliorating the primary or secondary symptoms of a Herpes Simplex Virus (HSV) infection is by inducing an anti-HSV immune response in said subject.

9. The method of claim 8, wherein said anti-HSV immune response is an anti-HSV neutralizing antibody response.

10. The method of claim 2, wherein the step of contacting comprises epidermal, intramuscular, subcutaneous, or intra-respiratory mucosal injection.

11. The mutant HSV-2 of claim 1, wherein said HSV-2 is strain 2.12.

12. The mutant HSV-2 of claim 1, wherein said mutant HSV has a defect in neuronal spread in the anterograde and retrograde directions.

* * * * *

SEQUENCE LISTING

<160> NUMBER OF SEQ ID NOS: 17

<210> SEQ ID NO 1
<211> LENGTH: 3104
<212> TYPE: DNA
<213> ORGANISM: Herpes Simplex Virus Type 1

<400> SEQUENCE: 1
gaatacaagc ttgcatgcct gcaggtcgac tctagaggat ccccgggtac cgagctcgaa 60
ttccggtctc cctatagtga gtcgtattaa tttcgataag ccagctgggc ctcgcgcgtt 120
tcggtgatga cggtgaaaac ctctgacaca tgcagctccc ggagacggtc acagcttgtc 180
tgtaagcgga tgccgggagc agacaagccc gtcagggcgc gtcagcgggt gttggcgggt 240
gtcggggcgc agccatgacc cagtcacgta gcgatagcgg agtgtatata ctggcttaac 300
tatgcggcat cagagcagat tgtactgaga gtgcaccata tgcggtgtga aataccgcac 360
agatgcgtaa ggagaaaata ccgcatcagg cgctcttccg cttcctcgct cactgactcg 420
ctgcgctcgg tcgttcggct gcggcgagcg gtatcagctc actcaaaggc ggtaatacgg 480
ttatccacag aatcagggga taacgcagga aagaacatgt gagcaaaagg ccagcaaaag 540
gccaggaacc gtaaaaaggc cgcgttgctg gcgtttttcc ataggctccg cccccctgac 600
gagcatcaca aaaatcgacg ctcaagtcag aggtggcgaa acccgacagg actataaaga 660
taccaggcgt ttccccctgg aagctccctc gtgcgctctc ctgttccgac cctgccgctt 720
accggatacc tgtccgcctt tctcccttcg ggaagcgtgg cgctttctca atgctcacgc 780

```
tgtaggtatc tcagttcggt gtaggtcgtt cgctccaagc tgggctgtgt gcacgaaccc    840
cccgttcagc ccgaccgctg cgccttatcc ggtaactatc gtcttgagtc caacccggta    900
agacacgact tatcgccact ggcagcagcc actggtaaca ggattagcag agcgaggtat    960
gtaggcggtg ctacagagtt cttgaagtgg tggcctaact acggctacac tagaaggaca   1020
gtatttggta tctgcgctct gctgaagcca gttaccttcg gaaaagagt tggtagctct    1080
tgatccggca acaaaccac cgctggtagc ggtggttttt ttgtttgcaa gcagcagatt    1140
acgcgcagaa aaaaggatc tcaagaagat cctttgatct tttctacggg gtctgacgct    1200
cagtggaacg aaaactcacg ttaagggatt ttggtcatga gattatcaaa aaggatcttc    1260
acctagatcc ttttaaatta aaatgaagt tttaaatcaa tctaaagtat atatgagtaa    1320
acttggtctg acagttacca atgcttaatc agtgaggcac ctatctcagc gatctgtcta   1380
tttcgttcat ccatagttgc ctgactcccc gtcgtgtaga taactacgat acgggagggc   1440
ttaccatctg gccccagtgc tgcaatgata ccgcgagacc cacgctcacc ggctccagat   1500
ttatcagcaa taaaccagcc agccggaagg gccgagcgca gaagtggtcc tgcaacttta   1560
tccgcctcca tccagtctat taattgttgc cgggaagcta gagtaagtag ttcgccagtt   1620
aatagtttgc gcaacgttgt tgccattgct acaggcatcg tggtgtcacg ctcgtcgttt   1680
ggtatggctt cattcagctc cggttcccaa cgatcaaggc gagttacatg atccccatg    1740
ttgtgcaaaa aagcggttag ctccttcggt cctccgatcg ttgtcagaag taagttggcc   1800
gcagtgttat cactcatggt tatggcagca ctgcataatt ctcttactgt catgccatcc   1860
gtaagatgct tttctgtgac tggtgagtac tcaaccaagt cattctgaga atagtgtatg   1920
cggcgaccga gttgctcttg cccggcgtca atacgggata ataccgcgcc acatagcaga   1980
actttaaaag tgctcatcat tggaaaacgt tcttcgggc gaaaactctc aaggatctta    2040
ccgctgttga gatccagttc gatgtaaccc actcgtgcac ccaactgatc ttcagcatct   2100
tttactttca ccagcgtttc tgggtgagca aaaacaggaa ggcaaaatgc cgcaaaaaag   2160
ggaataaggg cgacacggaa atgttgaata ctcatactct tccttttca atattattga    2220
agcatttatc agggttattg tctcatgagc ggatacatat ttgaatgtat ttagaaaaat   2280
aaacaaatag gggttccgcg cacatttccc cgaaaagtgc cacctgacgt ctaagaaacc   2340
attattatca tgacattaac ctataaaaat aggcgtatca cgaggccctt tcgtctcgcg   2400
cgtttcggtg atgacggtga aaacctctga cacatgcagc tcccggagac ggtcacagct   2460
tgtctgtaag cggatgccgg gagcagacaa gcccgtcagg gcgcgtcagc gggtgttggc   2520
gggtgtcggg gctggcttaa ctatgcggca tcagagcaga ttgtactgag agtgcaccat   2580
atcgacgctc tcccttatgc gactcctgca ttaggaagca gcccagtagt aggttgaggc   2640
cgttgagcac cgccgccgca aggaatggtg catgcaagga gatggcgccc aacagtcccc   2700
cggccacggg cctgccacca tacccacgcc gaaacaagcg ctcatgagcc cgaagtggcg   2760
agcccgatct tccccatcgg tgatgtcggc gatataggcg ccagcaaccg cacctgtggc   2820
gccggtgatg ccggccacga tgcgtccggc gtagaggatc tggctagcga tgaccctgct   2880
gattggttcg ctgaccattt ccgggtgcgg gacggcgtta ccagaaactc agaaggttcg   2940
tccaaccaaa ccgactctga cggcagttta cgagagagat gatagggtct gcttcagtaa   3000
gccagatgct acacaattag gcttgtacat attgtcgtta gaacgcggct acaattaata   3060
cataacctta tgtatcatac acatacgatt taggtgacac tata                    3104
```

```
<210> SEQ ID NO 2
<211> LENGTH: 550
<212> TYPE: PRT
<213> ORGANISM: Herpes Simplex Virus Type 1

<400> SEQUENCE: 2

Met Asp Arg Gly Ala Val Val Gly Phe Leu Leu Gly Val Cys Val Val
1               5                   10                  15

Ser Cys Leu Ala Gly Thr Pro Lys Thr Ser Trp Arg Arg Val Ser Val
            20                  25                  30

Gly Glu Asp Val Ser Leu Leu Pro Ala Pro Gly Pro Thr Gly Arg Gly
        35                  40                  45

Pro Thr Gln Lys Leu Leu Trp Ala Val Glu Pro Leu Asp Gly Cys Gly
    50                  55                  60

Pro Leu His Pro Ser Trp Val Ser Leu Met Pro Pro Lys Gln Val Pro
65                  70                  75                  80

Glu Thr Val Val Asp Ala Ala Cys Met Arg Ala Pro Val Pro Leu Ala
                85                  90                  95

Met Ala Tyr Ala Pro Pro Ala Pro Ser Ala Thr Gly Gly Leu Arg Thr
            100                 105                 110

Asp Phe Val Trp Gln Glu Arg Ala Ala Val Val Asn Arg Ser Leu Val
        115                 120                 125

Ile His Gly Val Arg Glu Thr Asp Ser Gly Leu Tyr Thr Leu Ser Val
    130                 135                 140

Gly Asp Ile Lys Asp Pro Ala Arg Gln Val Ala Ser Val Val Leu Val
145                 150                 155                 160

Val Gln Pro Ala Pro Val Pro Thr Pro Pro Thr Pro Ala Asp Tyr
                165                 170                 175

Asp Glu Asp Asp Asn Asp Glu Gly Glu Asp Glu Ser Leu Ala Gly Thr
            180                 185                 190

Pro Ala Ser Gly Thr Pro Arg Leu Pro Pro Pro Ala Pro Pro Arg
        195                 200                 205

Ser Trp Pro Ser Ala Pro Glu Val Ser His Val Arg Gly Val Thr Val
210                 215                 220

Arg Met Glu Thr Pro Glu Ala Ile Leu Phe Ser Pro Gly Glu Thr Phe
225                 230                 235                 240

Ser Thr Asn Val Ser Ile His Ala Ile Ala His Asp Asp Gln Thr Tyr
                245                 250                 255

Ser Met Asp Val Val Trp Leu Arg Phe Asp Val Pro Thr Ser Cys Ala
            260                 265                 270

Glu Met Arg Ile Tyr Glu Ser Cys Leu Tyr His Pro Gln Leu Pro Glu
        275                 280                 285

Cys Leu Ser Pro Ala Asp Ala Pro Cys Ala Ala Ser Thr Trp Thr Ser
    290                 295                 300

Arg Leu Ala Val Arg Ser Tyr Ala Gly Cys Ser Arg Thr Asn Pro Pro
305                 310                 315                 320

Pro Arg Cys Ser Ala Glu Ala His Met Glu Pro Val Pro Gly Leu Ala
                325                 330                 335

Trp Gln Ala Ala Ser Val Asn Leu Glu Phe Arg Asp Ala Ser Pro Gln
            340                 345                 350

His Ser Gly Leu Tyr Leu Cys Val Val Tyr Val Asn Asp His Ile His
        355                 360                 365

Ala Trp Gly His Ile Thr Ile Ser Thr Ala Ala Gln Tyr Arg Asn Ala
    370                 375                 380
```

Val Val Glu Gln Pro Leu Pro Gln Arg Gly Ala Asp Leu Ala Glu Pro
385                 390                 395                 400

Thr His Pro His Val Gly Ala Pro Pro His Ala Pro Pro Thr His Gly
            405                 410                 415

Ala Leu Arg Leu Gly Ala Val Met Gly Ala Ala Leu Leu Leu Ser Ala
            420                 425                 430

Leu Gly Leu Ser Val Trp Ala Cys Met Thr Cys Trp Arg Arg Arg Ala
            435                 440                 445

Trp Arg Ala Val Lys Ser Arg Ala Ser Gly Lys Gly Pro Thr Tyr Ile
450                 455                 460

Arg Val Ala Asp Ser Glu Leu Tyr Ala Asp Trp Ser Ser Asp Ser Glu
465                 470                 475                 480

Gly Glu Arg Asp Gln Val Pro Trp Leu Ala Pro Pro Glu Arg Pro Asp
            485                 490                 495

Ser Pro Ser Thr Asn Gly Ser Gly Phe Glu Ile Leu Ser Pro Thr Ala
            500                 505                 510

Pro Ser Val Tyr Pro Arg Ser Asp Gly His Gln Ser Arg Arg Gln Leu
            515                 520                 525

Thr Thr Phe Gly Ser Gly Arg Pro Asp Arg Arg Tyr Ser Gln Ala Ser
            530                 535                 540

Asp Ser Ser Val Phe Trp
545                 550

<210> SEQ ID NO 3
<211> LENGTH: 1653
<212> TYPE: DNA
<213> ORGANISM: Herpes Simplx Virus

<400> SEQUENCE: 3

```
atggatcgcg gggcggtggt ggggtttctt ctcggtgttt gtgttgtatc gtgcttggcg    60
ggaacgccca aaacgtcctg agacgggtg agtgtcggcg aggacgtttc gttgcttcca   120
gctccggggc ctacggggcg cggcccgacc cagaaactac tatgggccgt gaacccctg    180
gatgggtgcg ccccttaca cccgtcgtgg gtctcgctga tgcccccaa gcaggtgccc    240
gagacggtcg tggatgcggc gtgcatgcgc gctccggtcc cgctggcgat ggcgtacgcc   300
ccccggccc catctgcgac cgggggtcta cgaacggact cgtgtggca ggagcgcgcg    360
gccgtggtta accggagtct ggttattcac ggggtccgag agacggacag cggcctgtat   420
accctgtccg tgggcgacat aaaggacccg gctcgccaag tggcctcggt ggtcctggtg   480
gtgcaaccgg cccagttcc gaccccaccc ccgaccccag ccgattacga cgaggatgac   540
aatgacgagg gcgaggacga aagtctcgcc ggcactcccg ccagcgggac ccccggctc    600
ccgcctcccc ccgcccccc gaggtcttgg ccagcgccc ccgaagtctc acatgtgcgt    660
ggggtgaccg tgcgtatgga gactccggaa gctatcctgt tttcccccgg ggagacgttc   720
agcacgaacg tctccatcca tgccatcgcc acgacgacc agacctactc catggacgtc    780
gtctggttga ggttcgacgt gccgacctcg tgtgccgaga tgcgaatata cgaatcgtgt   840
ctgtatcacc gcagctccc agaatgtctg tccccggccg acgcgccgtg cgccgcgagt   900
acgtggacgt ctcgcctggc cgtccgcagc tacgcggggt gttccagaac aaaccccca    960
ccgcgctgtt cggccgaggc tcacatggag cccgtccgg ggctggcgtg gcaggcggcc   1020
tccgtcaatc tggagttccg ggacgcgtcc cacaacact ccggcctgta tctgtgtgtg   1080
gtgtacgtca acgaccatat tcacgcctgg ggccacatta ccatcagcac cgcggcgcag   1140
```

```
taccggaacg cggtggtgga acagcccctc ccacagcgcg gcgcggattt ggccgagccc    1200
acccacccgc acgtcggggc ccctcccac gcgcccccaa cccacggcgc cctgcggtta    1260
ggggcggtga tggggccgc cctgctgctg tctgcactgg ggttgtcggt gtgggcgtgt    1320
atgacctgtt ggcgcaggcg tgcctggcgg gcggttaaaa gcagggcctc gggtaagggg    1380
cccacgtaca ttcgcgtggc cgacagcgag ctgtacgcgg actggagctc ggacagcgag    1440
ggagaacgcg accaggtccc gtggctggcc ccccggaga gacccgactc tccctccacc    1500
aatggatccg gctttgagat cttatcacca acggctccgt ctgtataccc ccgtagcgat    1560
gggcatcaat ctcgccgcca gctcacaacc tttggatccg gaaggcccga tcgccgttac    1620
tcccaggcct ccgattcgtc cgtcttctgg taa                                1653
```

<210> SEQ ID NO 4
<211> LENGTH: 552
<212> TYPE: PRT
<213> ORGANISM: Herpes SImplex Virus

<400> SEQUENCE: 4

```
Met Asp Arg Gly Ala Val Val Gly Phe Leu Leu Gly Val Cys Val Val
1               5                   10                  15

Ser Cys Leu Ala Gly Thr Pro Lys Thr Ser Trp Arg Arg Val Ser Val
            20                  25                  30

Gly Glu Asp Val Ser Leu Leu Pro Ala Pro Gly Pro Thr Gly Arg Gly
        35                  40                  45

Pro Thr Gln Lys Leu Leu Trp Ala Val Glu Pro Leu Asp Gly Cys Gly
    50                  55                  60

Pro Leu His Pro Ser Trp Val Ser Leu Met Pro Pro Lys Gln Val Pro
65                  70                  75                  80

Glu Thr Val Val Asp Ala Ala Cys Met Arg Ala Pro Val Pro Leu Ala
                85                  90                  95

Met Ala Tyr Ala Pro Pro Ala Pro Ser Ala Thr Gly Gly Leu Arg Thr
            100                 105                 110

Asp Phe Val Trp Gln Glu Arg Ala Ala Val Val Asn Arg Ser Leu Val
        115                 120                 125

Ile Tyr Gly Val Arg Glu Thr Asp Ser Gly Leu Tyr Thr Leu Ser Val
    130                 135                 140

Gly Asp Ile Lys Asp Pro Ala Arg Gln Val Ala Ser Val Val Leu Val
145                 150                 155                 160

Val Gln Pro Ala Pro Val Pro Thr Pro Pro Thr Pro Ala Asp Tyr
                165                 170                 175

Asp Glu Asp Asp Asn Asp Glu Gly Glu Gly Glu Asp Glu Ser Leu Ala
            180                 185                 190

Gly Thr Pro Ala Ser Gly Thr Pro Arg Leu Pro Pro Ser Pro Ala Pro
        195                 200                 205

Pro Arg Ser Trp Pro Ser Ala Pro Glu Val Ser His Val Arg Gly Val
    210                 215                 220

Thr Val Arg Met Glu Thr Pro Glu Ala Ile Leu Phe Ser Pro Gly Glu
225                 230                 235                 240

Ala Phe Ser Thr Asn Val Ser Ile His Ala Ile Ala His Asp Asp Gln
                245                 250                 255

Thr Tyr Thr Met Asp Val Val Trp Leu Arg Phe Asp Val Pro Thr Ser
            260                 265                 270

Cys Ala Glu Met Arg Ile Tyr Glu Ser Cys Leu Tyr His Pro Gln Leu
        275                 280                 285
```

```
Pro Glu Cys Leu Ser Pro Ala Asp Ala Pro Cys Ala Ala Ser Thr Trp
    290                 295                 300
Thr Ser Arg Leu Ala Val Arg Ser Tyr Ala Gly Cys Ser Arg Thr Asn
305                 310                 315                 320
Pro Pro Pro Arg Cys Ser Ala Glu Ala His Met Glu Pro Phe Pro Gly
                325                 330                 335
Leu Ala Trp Gln Ala Ala Ser Val Asn Leu Glu Phe Arg Asp Ala Ser
            340                 345                 350
Pro Gln His Ser Gly Leu Tyr Leu Cys Val Val Tyr Val Asn Asp His
        355                 360                 365
Ile His Ala Trp Gly His Ile Thr Ile Asn Thr Ala Ala Gln Tyr Arg
370                 375                 380
Asn Ala Val Val Glu Gln Pro Leu Pro Gln Arg Gly Ala Asp Leu Ala
385                 390                 395                 400
Glu Pro Thr His Pro His Val Gly Ala Pro His Ala Pro Pro Thr
                405                 410                 415
His Gly Ala Leu Arg Leu Gly Ala Val Met Gly Ala Ala Leu Leu Leu
            420                 425                 430
Ser Ala Leu Gly Leu Ser Val Trp Ala Cys Met Thr Cys Trp Arg Arg
        435                 440                 445
Arg Ala Trp Arg Ala Val Lys Ser Arg Ala Ser Gly Lys Gly Pro Thr
    450                 455                 460
Tyr Ile Arg Val Ala Asp Ser Glu Leu Tyr Ala Asp Trp Ser Ser Asp
465                 470                 475                 480
Ser Glu Gly Glu Arg Asp Gln Val Pro Trp Leu Ala Pro Pro Glu Arg
                485                 490                 495
Pro Asp Ser Pro Ser Thr Asn Gly Ser Gly Phe Glu Ile Leu Ser Pro
            500                 505                 510
Thr Ala Pro Ser Val Tyr Pro Arg Ser Asp Gly His Gln Ser Arg Arg
        515                 520                 525
Gln Leu Thr Thr Phe Gly Ser Gly Arg Pro Asp Arg Arg Tyr Ser Gln
    530                 535                 540
Ala Ser Asp Ser Ser Val Phe Trp
545                 550

<210> SEQ ID NO 5
<211> LENGTH: 1659
<212> TYPE: DNA
<213> ORGANISM: Herpes Simplex Virus

<400> SEQUENCE: 5
atggatcgcg gggcggtggt gggggtttctt ctcggtgttt gtgttgtatc gtgcttggcg      60
ggaacgccca aaacgtcctg gagacgggtg agtgtcggcg aggacgtttc gttgctacca     120
gctccggggc ctacggggcg cggcccgacc cagaaactac tatgggccgt ggaaccctg      180 gatgggtgcg gccccttaca cccgtcgtgg gtctcgctga tgccccccaa gcaggtaccc     240
gagacggtcg tggatgcggc gtgcatgcgc gctccggtcc cgctggcgat ggcatacgcc     300 ccccggccc catctgcgac cggggggtcta cggacggact tcgtgtgca ggagcgcgcg      360 gccgtggtta accggagtct ggttatttac ggggtccgag agacggacag cggcctgtat     420
accctgtctg tgggcgacat aaaggacccg gctcgccaag tggcctcggt ggtcctggtg     480
gtgcaaccgg cccagttcc gactccaccc ccgaccccag ccgattacga cgaggatgac     540
aatgacgagg gcgagggcga ggacgaaagt ctagccggca ctcccgccag cgggaccccc     600
```

```
cggctcccgc cttccccgc cccccgagg tcttggccca gcgccccga agtctcacac    660 gtgcgtgggg tgaccgtgcg tatggagact ccggaagcta tcctgttttc ccccggggag    720
gcgtttagca cgaacgtctc catccatgcc atcgcccacg acgaccagac ctacaccatg    780
gacgtcgtct ggttgaggtt cgacgtgccg acctcgtgtg ccgagatgcg aatatacgaa    840
tcgtgtctgt atcatccgca gctcccagag tgtctgtccc cggccgacgc tccgtgcgcc    900
gcgagtacgt ggacgtctcg cctggccgtc cgcagctacg cggggtgttc cagaacaaac    960
cccccgccgc gctgttcggc cgaggctcac atggagccct cccgggggct ggcgtggcag   1020
gcggcctcag tcaatctgga gttccgggac gcgtccccac aacactccgg gctgtatctg   1080
tgcgtggtgt acgtcaacga ccatattcac gcatggggcc acattaccat caacaccgcg   1140
gcgcagtacc ggaacgcggt ggtggaacag cccctcccac agcgcggcgc ggatttggcc   1200
gagcccaccc acccgcacgt cggggcccct ccccacgcgc cccaaccca cggcgccctg   1260 cggttagggg cggtgatggg ggccgccctg ctgctgtctg cgctgggggtt gtcggtgtgg   1320 gcgtgtatga cctgttggcg caggcgtgcc tggcgggcgg ttaaaagcag ggcctcgggt   1380
aaggggccca cgtacattcg cgtggccgac agcgagctgt acgcggactg gagctcggac   1440
agcgagggag aacgcgacca ggtcccgtgg ctggccccc cggagagacc cgactctccc   1500
tccaccaatg gatccggctt tgagatctta tcaccaacgg ctccgtctgt ataccccgt   1560 agcgatgggc atcaatctcg ccgccagctc acaacctttg gatccggaag gcccgatcgc   1620
cgttactccc aggcctccga ttcgtccgtc ttctggtaa                          1659

<210> SEQ ID NO 6
<211> LENGTH: 545
<212> TYPE: PRT
<213> ORGANISM: Herpes Simplex Virus Type 2

<400> SEQUENCE: 6

Met Ala Arg Gly Ala Gly Leu Val Phe Phe Val Gly Val Trp Val Val
1               5                   10                  15

Ser Cys Leu Ala Ala Ala Pro Arg Thr Ser Trp Lys Arg Val Thr Ser
                20                  25                  30

Gly Glu Asp Val Val Leu Leu Pro Ala Pro Ala Glu Arg Thr Arg Ala
            35                  40                  45

His Lys Leu Leu Trp Ala Ala Glu Pro Leu Asp Ala Cys Gly Pro Leu
        50                  55                  60

Arg Pro Ser Trp Val Ala Leu Trp Pro Arg Arg Val Leu Glu Thr
65                  70                  75                  80

Val Val Asp Ala Ala Cys Met Arg Ala Pro Glu Pro Leu Ala Ile Ala
                85                  90                  95

Tyr Ser Pro Pro Phe Pro Ala Gly Asp Glu Gly Leu Tyr Ser Glu Leu
                100                 105                 110

Ala Trp Arg Asp Arg Val Ala Val Val Asn Glu Ser Leu Val Ile Tyr
            115                 120                 125

Gly Ala Leu Glu Thr Asp Ser Gly Leu Tyr Thr Leu Ser Val Val Gly
        130                 135                 140

Leu Ser Asp Glu Ala Arg Gln Val Ala Ser Val Leu Val Val Glu
145                 150                 155                 160

Pro Ala Pro Val Pro Thr Pro Thr Pro Asp Asp Tyr Asp Glu Glu Asp
                165                 170                 175

Asp Ala Gly Val Thr Asn Ala Arg Arg Ser Ala Phe Pro Pro Gln Pro
```

```
            180                 185                 190
Pro Pro Arg Arg Pro Val Ala Pro Pro Thr His Pro Arg Val Ile
            195                 200                 205
Pro Glu Val Ser His Val Arg Gly Val Thr Val His Met Glu Thr Leu
210                 215                 220
Glu Ala Ile Leu Phe Ala Pro Gly Glu Thr Phe Gly Thr Asn Val Ser
225                 230                 235                 240
Ile His Ala Ile Ala His Asp Asp Gly Pro Tyr Ala Met Asp Val Val
                    245                 250                 255
Trp Met Arg Phe Asp Val Pro Ser Ser Cys Ala Asp Met Arg Ile Tyr
                260                 265                 270
Glu Ala Cys Leu Tyr His Pro Gln Leu Pro Glu Cys Leu Ser Pro Ala
                275                 280                 285
Asp Ala Pro Cys Ala Val Ser Ser Trp Ala Tyr Arg Leu Ala Val Arg
                290                 295                 300
Ser Tyr Ala Gly Cys Ser Arg Thr Thr Pro Pro Arg Cys Phe Ala
305                 310                 315                 320
Glu Ala Arg Met Glu Pro Val Pro Gly Leu Ala Trp Leu Ala Ser Thr
                    325                 330                 335
Val Asn Leu Glu Phe Gln His Ala Ser Pro Gln His Ala Gly Leu Tyr
                340                 345                 350
Leu Cys Val Val Tyr Val Asp Asp His Ile His Ala Trp Gly His Met
                355                 360                 365
Thr Ile Ser Thr Ala Ala Gln Tyr Arg Asn Ala Val Val Glu Gln His
    370                 375                 380
Leu Pro Gln Arg Gln Pro Glu Pro Val Glu Pro Thr Arg Pro His Val
385                 390                 395                 400
Arg Ala Pro His Pro Ala Pro Ser Ala Arg Gly Pro Leu Arg Leu Gly
                    405                 410                 415
Ala Val Leu Gly Ala Ala Leu Leu Leu Ala Ala Leu Gly Leu Ser Ala
                420                 425                 430
Trp Ala Cys Met Thr Cys Trp Arg Arg Arg Ser Trp Arg Ala Val Lys
                435                 440                 445
Ser Arg Ala Ser Ala Thr Gly Pro Thr Tyr Ile Arg Val Ala Asp Ser
450                 455                 460
Glu Leu Tyr Ala Asp Trp Ser Ser Asp Ser Glu Gly Glu Arg Asp Gly
465                 470                 475                 480
Ser Leu Trp Gln Asp Pro Pro Glu Arg Pro Asp Ser Pro Ser Thr Asn
                    485                 490                 495
Gly Ser Gly Phe Glu Ile Leu Ser Pro Thr Ala Pro Ser Val Tyr Pro
                500                 505                 510
His Ser Glu Gly Arg Lys Ser Arg Arg Pro Leu Thr Thr Phe Gly Ser
                515                 520                 525
Gly Ser Pro Gly Arg Arg His Ser Gln Ala Ser Tyr Pro Ser Val Leu
                530                 535                 540
Trp
545

<210> SEQ ID NO 7
<211> LENGTH: 1638
<212> TYPE: DNA
<213> ORGANISM: Herpes Smplex Virus

<400> SEQUENCE: 7
```

```
atggctcgcg gggccgggtt ggtgtttttt gttggagttt gggtcgtatc gtgcctggcg    60
gcagcaccca gaacgtcctg gaaacgggta acctcgggcg aggacgtggt gttgcttccg   120
gcgcccgcgg aacgcacccg ggcccacaaa ctactgtggg ccgcggaacc cctggatgcc   180
tgcggtcccc tgcgcccgtc gtgggtggcg ctgtggcccc cccgacgggt gctcgagacg   240
gtcgtggatg cggcgtgcat gcgcgccccg gaaccgctcg ccatagcata cagtcccccg   300
ttccccgcgg gcgacgaggg actgtattcg gagttggcgt ggcgcgatcg cgtagccgtg   360
gtcaacgaga gtctggtcat ctacggggcc ctggagacgg acagcggtct gtacaccctg   420
tccgtggtcg gcctaagcga cgaggcgcgc caagtggcgt cggtggttct ggtcgtggag   480
cccgcccctg tgccgacccc gaccccgac gactacgacg aagaagacga cgcgggcgtg   540
acgaacgcac gccggtcagc gttcccccc caacccccc ccgtcgtcc cccgtcgcc     600
ccccgacgc accctcgtgt tatccccgag gtgtcccacg tgcgcggggt aacggtccat   660
atggagaccc tggaggccat tctgtttgcc cccggggaga cgtttgggac gaacgtctcc   720
atccacgcca ttgcccacga cgacggtccg tacgccatgg acgtcgtctg gatgcggttt   780
gacgtgccgt cctcgtgcgc cgatatgcgg atctacgaag cttgtctgta tcacccgcag   840
cttccagagt gtctatctcc ggccgacgcg ccgtgcgccg taagttcctg ggcgtaccgc   900
ctggcggtcc gcagctacgc cggctgttcc aggactacgc ccccgccgcg atgttttgcc   960
gaggctcgca tggaaccggt cccgggggttg gcgtggctgg cctccaccgt caatctggaa  1020
ttccagcacg cctccccca gcacgccggc ctctacctgt gcgtggtgta cgtggacgat  1080
catatccacg cctggggcca catgaccatc agcaccgcgg cgcagtaccg gaacgcggtg  1140
gtggaacagc acctccccca gcgccagccc gagcccgtcg agcccacccg cccgcacgtg  1200
agagccccc atcccgcgcc ctccgcgcgc ggcccgctgc gcctcgggc ggtgctgggg   1260
gcggccctgt tgctggccgc cctcgggctg tccgcgtggg cgtgcatgac ctgctggcgc  1320
aggcgctcct ggcgggcggt taaaagccgg gcctcggcga cgggcccac ttacattcgc   1380
gtggcggaca gcgagctgta cgcggactgg agttcggaca gcgaggggga gcgcgacggg  1440
tccctgtggc aggaccctcc ggagagaccc gactctccct ccacaaatgg atccggcttt   1500
gagatcttat caccaacggc tccgtctgta taccccata gcgaggggcg taaatctcgc   1560
cgcccgctca ccacctttgg ttcgggaagc ccgggccgtc gtcactccca ggcctcctat   1620
ccgtccgtcc tctggtaa                                                1638

<210> SEQ ID NO 8
<211> LENGTH: 22
<212> TYPE: DNA
<213> ORGANISM: Artificial sequence
<220> FEATURE:
<223> OTHER INFORMATION: primer

<400> SEQUENCE: 8
cgacgcctta ataccgactg tt                                            22

<210> SEQ ID NO 9
<211> LENGTH: 20
<212> TYPE: DNA
<213> ORGANISM: Artificial sequence
<220> FEATURE:
<223> OTHER INFORMATION: primer

<400> SEQUENCE: 9
acagcgcgat ccgacatgtc                                               20
```

```
<210> SEQ ID NO 10
<211> LENGTH: 23
<212> TYPE: DNA
<213> ORGANISM: Artificial sequence
<220> FEATURE:
<223> OTHER INFORMATION: primer

<400> SEQUENCE: 10
tcgttggccg cctcgtcttc gct                                           23

<210> SEQ ID NO 11
<211> LENGTH: 22
<212> TYPE: DNA
<213> ORGANISM: Artificial sequence
<220> FEATURE:
<223> OTHER INFORMATION: primer

<400> SEQUENCE: 11
gatgcagtcg aaggtgtggt ta                                            22

<210> SEQ ID NO 12
<211> LENGTH: 22
<212> TYPE: DNA
<213> ORGANISM: Artificial sequence
<220> FEATURE:
<223> OTHER INFORMATION: primer

<400> SEQUENCE: 12
cggtaggatg acactcgggt at                                            22

<210> SEQ ID NO 13
<211> LENGTH: 21
<212> TYPE: DNA
<213> ORGANISM: Artificial sequence
<220> FEATURE:
<223> OTHER INFORMATION: primer

<400> SEQUENCE: 13
tctcgcgtct gtggcaatgg c                                             21

<210> SEQ ID NO 14
<211> LENGTH: 392
<212> TYPE: PRT
<213> ORGANISM: Herpes Simplex Virus Type 1

<400> SEQUENCE: 14

Met Gly Gly Thr Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Thr Asp Pro Pro Gly Val Arg Arg Val Tyr His
    50                  55                  60

Ile Gln Ala Gly Leu Pro Asp Pro Phe Gln Pro Pro Ser Leu Pro Ile
65                  70                  75                  80

Thr Val Tyr Tyr Ala Val Leu Glu Arg Ala Cys Arg Ser Val Leu Leu
                85                  90                  95

Asn Ala Pro Ser Glu Ala Pro Gln Ile Val Arg Gly Ala Ser Glu Asp
            100                 105                 110

Val Arg Lys Gln Pro Tyr Asn Leu Thr Ile Ala Trp Phe Arg Met Gly
```

```
            115                 120                 125
Gly Asn Cys Ala Ile Pro Ile Thr Val Met Glu Tyr Thr Glu Cys Ser
            130                 135                 140

Tyr Asn Lys Ser Leu Gly Ala Cys Pro Ile Arg Thr Gln Pro Arg Trp
145                 150                 155                 160

Asn Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
            195                 200                 205

Arg Ala Lys Gly Ser Cys Lys Tyr Ala Leu Pro Leu Arg Ile Pro Pro
            210                 215                 220

Ser Ala Cys Leu Ser Pro Gln Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Val Tyr Ser Leu Lys Ile Ala Gly Trp His Gly Pro Lys Ala Pro
                260                 265                 270

Tyr Thr Ser Thr Leu Leu Pro Pro Glu Leu Ser Glu Thr Pro Asn Ala
            275                 280                 285

Thr Gln Pro Glu Leu Ala Pro Glu Asp Pro Glu Asp Ser Ala Leu Leu
            290                 295                 300

Glu Asp Pro Val Gly Thr Val Ala Pro Gln Ile Pro Pro Asn Trp His
305                 310                 315                 320

Ile Pro Ser Ile Gln Asp Ala Ala Thr Pro Tyr His Pro Pro Ala Thr
                325                 330                 335

Pro Asn Asn Met Gly Leu Ile Ala Gly Ala Val Gly Gly Ser Leu Leu
            340                 345                 350

Ala Ala Leu Val Ile Cys Gly Ile Val Tyr Trp Met His Arg Arg Thr
            355                 360                 365

Arg Lys Ala Pro Lys Arg Ile Arg Leu Pro His Ile Arg Glu Asp Asp
370                 375                 380

Gln Pro Ser Ser His Gln Pro Leu
385                 390
```

<210> SEQ ID NO 15
<211> LENGTH: 1608
<212> TYPE: DNA
<213> ORGANISM: Herpes Simplex Virus Type 1

<400> SEQUENCE: 15

```
gtggccccgg cccccaacaa aaatcacggt agcccggccg tgtgacacta tcgtccatac      60
cgaccacacc gacgaacccc taaggggag gggccatttt acgaggagga ggggtataac     120
aaagtctgtc tttaaaaagc agggttagg gagttgttcg gtcataagct tcagcgcgaa     180
cgaccaacta ccccgatcat cagttatcct taaggtctct tttgtgtggt gcgttccggt     240
atgggggga ctgccgccag gttgggggcc gtgattttgt ttgtcgtcat agtgggcctc     300
catgggtcc gcggcaaata tgccttggcg gatgcctctc tcaagatggc gaccccaat     360
cgctttcgcg gcaaagacct tccggtcctg accagctga ccgaccctcc gggggtccgg     420
cgcgtgtacc acatccaggc gggcctaccg gacccgttcc agccccccag cctcccgatc     480
acggtttact acgccgtgtt ggagcgcgcc tgccgcagcg tgctcctaaa cgcaccgtcg     540
```

-continued

```
gaggcccccc agattgtccg cggggcctcc gaagacgtcc ggaaacaacc ctacaacctg    600
accatcgctt ggtttcggat gggaggcaac tgtgctatcc ccatcacggt catggagtac    660
accgaatgct cctacaacaa gtctctgggg gcctgtccca tccgaacgca gccccgctgg    720
aactactatg acagcttcag cgccgtcagc gaggataacc tggggttcct gatgcacgcc    780
cccgcgtttg agaccgccgg cacgtacctg cggctcgtga agataaacga ctggacggag    840
attacacagt ttatcctgga gcaccgagcc aagggctcct gtaagtacgc cctcccgctg    900
cgcatccccc cgtcagcctg cctctccccc caggcctacc agcaggggt gacggtggac    960 agcatcggga tgctgccccg cttcatcccc gagaaccagc gcaccgtcgc cgtatacagc   1020
ttgaagatcg ccgggtggca cgggcccaag gccccataca cgagcaccct gctgccccg    1080 gagctgtccg agaccccaa cgccacgcag ccagaactcg ccccggaaga ccccgaggat   1140
tcggccctct tggaggaccc cgtggggacg gtggcgccgc aaatcccacc aaactggcac   1200
atcccgtcga tccaggacgc cgcgacgcct taccatcccc cggccacccc gaacaacatg   1260
ggcctgatcg ccggcgcggt gggcggcagt ctcctggcag ccctggtcat ttgcggaatt   1320
gtgtactgga tgcaccgccg cactcggaaa gccccaaagc gcatacgcct ccccacatc    1380 cgggaagacg accagccgtc ctcgcaccag cccttgtttt actagatacc ccccttaat    1440 gggtgcgggg gggtcaggtc tgcggggttg ggatgggacc ttaactccat ataaagcgag   1500
tctggaaggg gggaaaggcg gacagtcgat aagtcggtag cggggacgc gcacctgttc    1560 cgcctgtcgc acccacagct ttttcgcgaa ccgtcccgtt ttcgggat               1608
```

<210> SEQ ID NO 16
<211> LENGTH: 393
<212> TYPE: PRT
<213> ORGANISM: Herpes Simplex Virus Type 2

<400> SEQUENCE: 16

```
Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190
```

```
Val Lys Ile Asn Asp Trp Thr Glu Ile Thr Gln Phe Ile Leu Glu His
    195                 200                 205

Arg Ala Arg Ala Ser Cys Lys Tyr Ala Leu Pro Leu Arg Ile Pro Pro
210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
            340                 345                 350

Val Leu Val Ile Gly Gly Ile Ala Phe Trp Val Arg Arg Arg Ala Gln
        355                 360                 365

Met Ala Pro Lys Arg Leu Arg Leu Pro His Ile Arg Asp Asp Asp Ala
    370                 375                 380

Pro Pro Ser His Gln Pro Leu Phe Tyr
385                 390

<210> SEQ ID NO 17
<211> LENGTH: 1182
<212> TYPE: DNA
<213> ORGANISM: Herpes Simplex Virus Type 2

<400> SEQUENCE: 17
atggggcgtt tgacctccgg cgtcgggacg gcggccctgc tagttgtcgc ggtgggactc      60
cgcgtcgtct gcgccaaata cgccttagca dccccctcgc ttaagatggc cgatcccaat     120
cgatttcgcg ggaagaacct tccggttttg gaccagctga ccgacccccc cggggtgaag     180
cgtgtttacc acattcagcc gagcctggag gacccgttcc agccccccag catcccgatc     240
actgtgtact acgcagtgct ggaacgtgcc tgccgcagcg tgctcctaca tgccccatcg     300
gaggcccccc agatcgtgcg cggggcttcg gacgaggccc gaaagcacac gtacaacctg     360
accatcgcct ggtatcgcat gggagacaat tgcgctatcc ccatcacggt tatggaatac     420
accgagtgcc cctacaacaa gtcgttgggg gtctgcccca tccgaacgca gccccgctgg     480
agctactatg acagctttag cgccgtcagc gaggataacc tgggattcct gatgcacgcc     540
cccgccttcg agaccgcggg tacgtacctg cggctagtga agataaacga ctggacggag     600
atcacacaat ttatcctgga gcaccgggcc cgcgcctcct gcaagtacgc tctcccctg      660 cgcatccccc cggcagcgtg cctcacctcg aaggcctacc aacagggcgt gacggtcgac     720
agcatcggga tgctaccccg ctttatcccc gaaaaccagc gcaccgtcgc cctatacagc     780
ttaaaaatcg ccgggtggca cggccccaag ccccgtaca ccagcaccct gctgccgccg      840
gagctgtccg acaccaccaa cgccacgcaa cccgaactcg ttccggaaga ccccgaggac     900
tcggccctct tagaggatcc cgccgggacg gtgtcttcgc agatcccccc aaactggcac     960
```

-continued

```
atcccgtcga tccaggacgt cgcgccgcac cacgccccng ccgccccag caacccgggc    1020 ctgatcatcg gcgcgctggc cggcagtacc ctggcggtgc tggtcatcgg cggtattgcg    1080
ttttgggtac gccgccgcgc tcagatggcc cccaagcgcc tacgtctccc ccacatccgg    1140
gatgacgacg cgcccccctc gcaccagcca ttgttttact ag                      1182
```